US012655406B2

(12) United States Patent
Segovia Sanz et al.

(10) Patent No.: US 12,655,406 B2
(45) Date of Patent: Jun. 16, 2026

(54) PYRUVATE KINASE DEFICIENCY (PKD) GENE EDITING TREATMENT METHOD

(71) Applicants:CENTRO DE INVESTIGACIONES ENERGÉTICAS, MEDIOAMBIENTALES Y TECNOLÓGICAS, O.A., M.P., Madrid (ES); CONSORCIO CENTRO DE INVESTIGACIÓN BIOMÉDICA EN RED, Madrid (ES); FUNDACIÓN INSTITUTO DE INVESTIGACIÓN SANITARIA FUNDACIÓN JIMÉNEZ DÍAZ, Madrid (ES)

(72) Inventors: José Carlos Segovia Sanz, Madrid (ES); Óscar Quintana Bustamante, Madrid (ES); Sara Fañanas Baquero, Madrid (ES)

(73) Assignees: CENTRO DE INVESTIGACIONES ENERGÉTICAS, MEDIOAMBIENTALES Y TECNOLÓGICAS, O.A., M.P., Madrid (ES); CONSORCIO CENTRO DE INVESTIGACIÓN BIOMÉDICA EN RED, Madrid (ES); FUNDACIÓN INSTITUTO DE INVESTIGACIÓN SANITARIA FUNDACIÓN JIMÉNEZ DÍAZ, Madrid (ES)

( * ) Notice: Subject to any disclaimer, the term of this patent is extended or adjusted under 35 U.S.C. 154(b) by 732 days.

(21) Appl. No.: 18/012,894

(22) PCT Filed: Jun. 28, 2021

(86) PCT No.: PCT/EP2021/067719
§ 371 (c)(1),
(2) Date: Dec. 23, 2022

(87) PCT Pub. No.: WO2021/260227
PCT Pub. Date: Dec. 30, 2021

(65) Prior Publication Data
US 2023/0303990 A1 Sep. 28, 2023

(30) Foreign Application Priority Data

Jun. 26, 2020 (EP) .................................... 20382568

(51) Int. Cl.
*C12N 15/85* (2006.01)
*C12N 9/22* (2006.01)
*C12N 15/86* (2006.01)
(52) U.S. Cl.
CPC .............. *C12N 9/22* (2013.01); *C12N 15/86* (2013.01); *C12N 2310/20* (2017.05); *C12N 2750/14143* (2013.01)
(58) Field of Classification Search
None
See application file for complete search history.

(56) References Cited

U.S. PATENT DOCUMENTS

| | | | | |
|---|---|---|---|---|
| 11,254,933 | B2 * | 2/2022 | Gilbert | ............... C12N 15/1079 |
| 2017/0204407 | A1 * | 7/2017 | Gilbert | ............... C12N 15/1082 |

OTHER PUBLICATIONS

Bak et al., "CRISPR/Cas9 genome editing in human hematopoietic stem cells," *Nature Protocols* 13(2):358-376, Feb. 2018 (HHS Public Access Author Manuscript, available in PMC Feb. 26, 2018), 38 pages.
Charlesworth et al., "Priming Human Repopulating Hematopoietic Stem and Progenitor Cells for Cas9/sgRNA Gene Targeting," *Molecular Therapy: Nucleic Acids* 12:89-104, https://doi.org/10.1016/j.omtn.2018.04.017, Sep. 2018.
Dever et al., "CRISPR/Cas9 Beta-globin Gene Targeting in Human Hematopoietic Stem Cells," *Nature* 539:384-389, Nov. 2016 (Europe PMC Public Access Author Manuscript, available in PMC Apr. 13, 2018), 33 pages.
Ferrari et al., "Resistance to *Botrytis cinerea* Induced in *Arabidopsis* by Elicitors Is Independent of Salicylic Acid, Ethylene, or Jasmonate Signaling But Requires Phytoalexin Deficient3[1][W]," *Plant Physiology* 144:367-379, doi/10.1104/pp.107.095596, May 2007.
Garcia-Gomez et al., "Safe and Efficient Gene Therapy for Pyruvate Kinase Deficiency," *Molecular Therapy* 24(7):1187-1198, Jul. 2016.
Greaves et al., "Clonal Evolution in Cancer," *Nature* 481:306-313, Jan. 2012 (HHS Public Access Author Manuscript, available in PMC Jul. 19, 2012), 20 pages.
Khan, "Gene Expression in Mammalian Cells and its Applications," *Advanced Pharmaceutical Bulletin* 3(2):257-263, DOI: 10.5681/apb.2013.042, Aug. 2013.
Pavel-Dinu et al., "Gene correction for SCID-X1 in long-term hematopoietic stem cells," *Nature Communications* 10, https://doi.org/10.1038/s41467-019-09614-y, Apr. 2019, 15 pages.
Quintana-Bustamante et al., "Gene editing of *PKLR* gene in human hematopoietic progenitors through 5' and 3' UTR modified TALEN mRNA," *PLOS ONE* 14(10), DOI: 10.1371/journal.pone.0223775, Oct. 2019, 20 pages.
Quintana Bustamante et al.,"Efficient CRISPR/Cas9-Mediated Gene Editing of Pklr in Human Hematopoietic Progenitors and Stem Cells for the Gene Therapy of Pyruvate Kinase Deficiency," *Blood* 132, Supplement 1, DOI: 10.1182/blood-2018-99-111772, Nov. 2018, 2 pages.

(Continued)

*Primary Examiner* — Marcia S Noble
(74) *Attorney, Agent, or Firm* — Seed Intellectual Property Law Group LLP

(57) ABSTRACT

The present invention relates to the treatment of Pyruvate Kinase Deficiency (PKD) using the Clustered-Regularly Interspaced Short Palindromic Repeats (CRISPR) system. This technology offers the possibility to design an improved single guide RNA (sgRNA), in particular, an improved crRNA to be associated with tracrRNA, which is incorporated into a CRISPR-associated protein (Cas9) to recognize and induce DNA double-strand breaks at a specific target location. DNA double-strand breaks will be repaired by homologous recombination (HR) in the presence of a donor sequence for PKLR gene repair.

21 Claims, 15 Drawing Sheets
Specification includes a Sequence Listing.

(56) References Cited

OTHER PUBLICATIONS

Vakulskas et al., "A high-fidelity Cas9 mutant delivered as a ribonucleoprotein complex enables efficient gene editing in human haematopoietic stem and progenitor cells," *Nature Medicine* 24(8):1216-1224, Aug. 2018 (HHS Public Access Author Manuscript, available in PMC Feb. 6, 2019), 34 pages.

* cited by examiner

PYRUVATE KINASE DEFICIENCY (PKD) GENE EDITING TREATMENT METHOD

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200326_401USPC_SEQUENCE_LISTING. The text file is 61.4 KB, was created on Dec. 23, 2022, and is being submitted electronically via EFS-Web.

TECHNICAL FIELD OF THE INVENTION

The present invention relates to the treatment of Pyruvate kinase deficiency (PKD) using the Clustered-Regularly Interspaced Short Palindromic Repeats (CRISPR) system. This technology offers the possibility to design an improved single guide RNA (sgRNA), in particular, an improved crRNA to be associated with a tracrRNA or to a linker, which is incorporated into a CRISPR-associated protein (Cas9) to recognize and induce DNA double-strand breaks at a specific target location. DNA double-strand breaks will be repaired by homologous recombination (HR) in the presence of a donor sequence for PKLR gene repair.

BACKGROUND OF THE INVENTION

Pyruvate kinase deficiency (PKD) is the most common erythroid inherited enzymatic defect causing chronic non-spherocytic hemolytic anemia. The prevalence of PKD is estimated at 1-9 cases per 100,000 people in the Caucasian population. PKD is an autosomal recessive disorder caused by mutations in the PKLR gene. This gene encodes for two different transcript variants, RPK and LPK, expressed in Red blood cells and liver respectively. To date, more than 200 different mutations in the PKLR gene have been linked to PKD. Therapy options for PKD are palliative and include regular red blood cell transfusion, splenectomy and iron chelation therapy. So far, allogeneic hematopoietic stem cell transplant (HSCT) represents the only curative treatment for severely affected patients. Autologous HSCT of genetically corrected cells, also called hematopoietic stem and progenitor cell (HSPC) gene therapy, is being used to treat many blood cell genetic diseases. CIEMAT has recently developed a lentiviral vector to correct PKD which has been granted orphan drug designation (EU/3/14/1330; FDA #DRU-2016-5168). This lentiviral-mediated gene therapy approach would offer a durable and curative clinical benefit with a single treatment.

Over the last few years, gene editing has emerged as a promising gene therapy approach for blood-cell disorders, since genetic mutations can be accurately corrected. The generation of double strand breaks (DSB), by using engineered endonucleases that cut in a specific genome location that recruit the DNA repair cell machinery together with the introduction of the desired DNA sequences to be introduced in that specific site has increased the gene editing efficiency to percentages that can be considered clinically applicable. The CRISPR-Cas9 system is one of the engineered endonucleases described so far. The introduction into a cell of specific sgRNA that recognizes the unique and specific site in the genome plus the Cas9 protein, that generates the DSB at that position, as a complex, also called ribonucleoprotein complex (RNPs), together with the use of Adeno-associated virus (AAV) for the delivery of donor templates, has been demonstrated to be the most efficient system to approach the field of gene editing for the treatment of patients with inherited hematopoietic diseases (Dever, Bak et al. 2016, Bak, Dever et al. 2018, Charlesworth, Camarena et al. 2018, Pavel-Dinu, Wiebking et al. 2019). CIEMAT has set up this approach to correct PKD and found that up to 40% of human hematopoietic progenitors have been gene edited with a therapeutic RPK (R-type pyruvate kinase) locus through combining specific RNP and AAVs. The results obtained suggest that the clinical use of gene editing therapy to correct PKD is highly likely in the short term.

One of the current bottlenecks to use gene editing to treat inherited disorders is the generation of DSB in places different from the selected specific on-target site that can generate undesired genetic modifications with unexpected clinical effects. This side effect of the CRISPR-Cas9 system, produced by the generation of undesired DSB, is called off-target effect. The off-targets generated by a specific sgRNA can hamper its clinical application, since hematopoietic stem cell gene therapy implies the genetic modification of millions of HSPCs, and so the number cells carrying undesired alterations in their genome might be significant. A single undesired modification in one of the transplanted HSPCs might cause an uncontrolled clonal proliferation that could jeopardize the therapy and put in risk the health of the patient. As it has been previously described both in a natural context, as well as in a hematopoietic stem cell gene therapy context, the alteration in the genome of a single HSPC or the random integration of the viral vector in the host genome, is able to trigger a leukemic process (Greaves and Maley 2012). Consequently, an important challenge for the use of CRISPR system is the need to identify and minimize the potentially harmful off-target mutations induced by these nucleases. Although the use of high-fidelity Cas9 has reduced significantly off-target activity (Vakulskas, Dever et al. 2018), off-target effects of therapeutic RNP need to be analysed carefully before using gene editing to treat patients.

High sensitivity analyses of potential off-target effect are mandatory for any clinical application, since even low-frequency events could potentially lead to deleterious outcomes. Methods involving in silico prediction of potential off-targets are the most frequently used to predict off-target effects. However, these approaches do not consider the genomic locations of the potential off-targets, neither the cell type of interest. Consequently, their ability to identify off-target sites of a specific sgRNA are very limited. The ideal method to analyse side effects of gene editing technology should be one that would identify off-target sites in a genome-wide unbiased fashion and with high sensitivity; that is, the ability to detect even low-frequency mutations in a very large cell population. GUIDE-seq is based on the efficient integration of a double-stranded oligodeoxynucleotide (dsODN) tag, followed by tag specific amplification and high-throughput sequencing. GUIDE-seq is highly sensitive and can detect off-target sites that are mutagenized by the tested sgRNA in a population of cells. Some of the advantages of GUIDE-seq include its experimental simplicity, the high efficiency and precision, as well as the detection of repair outcomes of nuclease-induced DSBs in a physiologically relevant cellular context. CIEMAT has assessed the off-target effects of the relevant sgRNAs through GUIDE-seq in the HSPCs themselves, attending to the strictest criteria to select therapeutic tools based on gene editing. These types of genome-wide unbiased analyses of side effects of the gene editing platforms will guarantee the safety of the clinical use of the gene editing in HSPCs.

US 12,655,406 B2

DESCRIPTION OF THE INVENTION

Description of the Invention

Definitions

Figure 1:
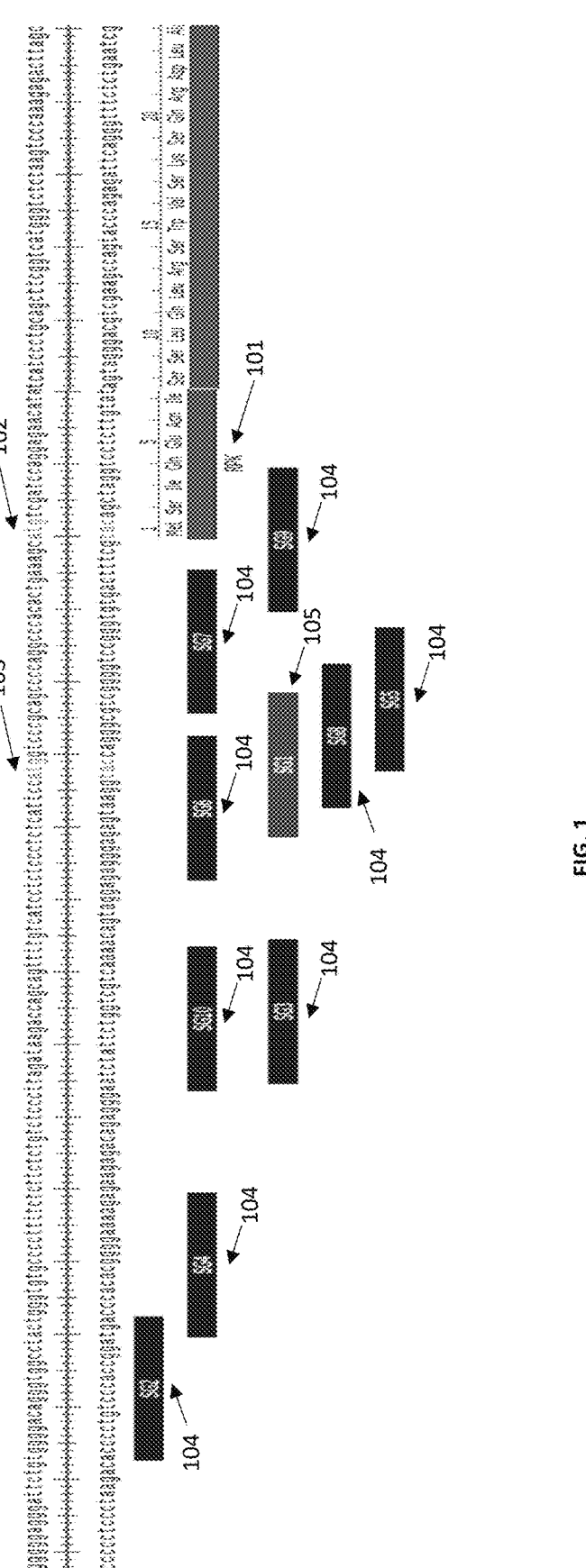
FIG. 1: Diagram showing the position of the different single guide RNAs with respect to the RPK start codon. Part of the RPK CDS is marked (101). ATG of RPK start codon is indicated (102). Cryptic ATG 30 bp upstream from RPK start codon is indicated (103). Additionally, single guide RNA targets in the genome are indicated (104), except SG1 target, which is indicated separately (105). SEQ ID NOS: 28, 34, 41.

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "gene" refers to a combination of polynucleotide elements, that when operatively linked in either a native or recombinant manner, provide some product or function. The term "gene" is to be interpreted broadly, and can encompass mRNA, cDNA, CRNA and genomic DNA forms of a gene.

The term "homology-directed repair" or "HDR" refers to a mechanism in cells to accurately and precisely repair double-strand DNA breaks using a homologous template to guide repair. The mechanism underlying HDR is homologous recombination (HR).

The term "homologous recombination" or "HR" refers to a genetic process in which nucleotide sequences are exchanged between two similar molecules of DNA. Homologous recombination (HR) is used by cells to accurately repair harmful breaks that occur on both strands of DNA, known as double-strand breaks or other breaks that generate overhanging sequences.

The term "single guide RNA" or "sgRNA" refer to a DNA-targeting RNA containing a guide sequence that targets the Cas nuclease to the target genomic DNA and a scaffold sequence that interacts with the Cas nuclease (e.g., tracrRNA). Preferably, said sgRNA comprises or consists of SEQ ID NO 1.

The term "Cas polypeptide" or "Cas nuclease" refers to a Clustered Regularly Interspaced Short Palindromic Repeats-associated polypeptide or nuclease that cleaves DNA to generate blunt ends at the double-strand break at sites specified by a 20-nucleotide guide sequence contained within the crRNA molecule. A Cas nuclease requires both a crRNA and a tracrRNA for site-specific DNA recognition and cleavage. The crRNA associates, through a region of partial complementarity, or through a linker, with the tracrRNA to guide the Cas nuclease to a region homologous to the crRNA in the target DNA called a "protospacer."

The term "HiFi-Cas9" is understood herein as a high-fidelity Cas9 mutant delivered as a ribonucleoprotein complex enables efficient gene editing with a similar On-target activity to wild type Cas9, but with a reduced Off-target activity. HiFi-Cas9 was described by Vakulskas et al. (Vakulskas, Dever et al. 2018).

The term "ribonucleoprotein complex" or "RNP complex" refers to a complex comprising an sgRNA and a Cas polypeptide.

The term "Adeno associated viral vector-delivered donor template" or "donor template-containing adeno-associated viral vector" refers to an adeno-associated viral particle that can deliver a recombinant donor template for CRISPR-based gene editing via homology-directed repair in a target cell, e.g., primary cell.

The term "recombinant donor template" refers to a nucleic acid strand, e.g., DNA strand that is the donor strand during homologous recombination strand invasion that is initiated by the damaged DNA repair mechanism, in some cases, resulting from a double-stranded break. The donor polynucleotide serves as template material to direct the repair of the damaged DNA region.

The terms "sequence identity" or "percent identity" in the context of two or more nucleic acids or polypeptides refer to two or more sequences or subsequences that are the same ("identical") or have a specified percentage of amino acid residues or nucleotides that are identical ("percent identity") when compared and aligned for maximum correspondence with a second molecule, as measured using a sequence comparison algorithm (e.g., by a BLAST alignment, or any other algorithm known to persons of skill), or alternatively, by visual inspection.

The term "homologous" refers to two or more amino acid sequences when they are derived, naturally or artificially, from a common ancestral protein or amino acid sequence. Similarly, nucleotide sequences are homologous when they are derived, naturally or artificially, from a common ancestral nucleic acid.

The term "primary cell" refers to a cell isolated directly from a multicellular organism. Primary cells typically have undergone very few population doublings and are therefore more representative of the main functional component of the tissue from which they are derived in comparison to continuous (tumor or artificially immortalized) cell lines. In some cases, primary cells are cells that have been isolated and then used immediately. In other cases, primary cells cannot divide indefinitely and thus cannot be cultured for long periods of time in vitro.

The term "gene modified primary cell" or "genome edited primary cell" refers to a primary cell into which a heterologous nucleic acid has been introduced in some cases, into its endogenous genomic DNA.

The term "pharmaceutical composition" refers to a composition that is physiologically acceptable and pharmacologically acceptable. In some instances, the composition includes an agent for buffering and preservation in storage, and can include buffers and carriers for appropriate delivery, depending on the route of administration.

The term "pharmaceutical acceptable carrier" refers to a substance that aids the administration of an agent (e.g., Cas nuclease, modified single guide RNA, gene modified primary cell, etc.) to a cell, an organism, or a subject. "Pharmaceutically acceptable carrier" refers to a carrier or excipient that can be included in a composition or formulation and that causes no significant adverse toxicological effect on the patient. Non-limiting examples of pharmaceutically acceptable carrier include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical carriers are useful in the present invention.

The term "administering or "administration" refers to the process by which agents, compositions, dosage forms and/or combinations disclosed herein are delivered to a subject for treatment or prophylactic purposes. Compositions, dosage forms and/or combinations disclosed herein are administered in accordance with good medical practices taking into account the subject's clinical condition, the site and method of administration, dosage, subject age, sex, body weight, and other factors known to the physician. For example, the terms "administering" or "administration" include providing, giving, dosing and/or prescribing agents, compositions, dosage forms and/or combinations disclosed herein by a clinician or other clinical professional.

The term "treating" refers to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The terms "subject," "patient," and "individual" are used herein interchangeably to include a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

Unless defined otherwise, all technical and scientific terms used herein have the same meanings as commonly understood by one of ordinary skill in the art to which this technology belongs. Although exemplary methods, devices and materials are described herein, any methods and materials similar or equivalent to those expressly described herein can be used in the practice or testing of the present technology. For example, the reagents described herein are merely exemplary and that equivalents of such are known in the art. The practice of the present technology can employ, unless otherwise indicated, conventional techniques of tissue culture, immunology, molecular biology, microbiology, cell biology, and recombinant DNA, which are within the skill of the art. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR I: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Miller and Calos eds. (1987) Gene Transfer Vectors for Mammalian Cells (Cold Spring Harbor Laboratory); and Makrides ed. (2003) Gene Transfer and Expression in Mammalian Cells (Cold Spring Harbor Laboratory).

DESCRIPTION

As already indicated in the background of the invention, over the last few years, gene editing has emerged as a promising gene therapy approach for blood-cell disorders, since genetic mutations can be accurately corrected. RNPs, together with the use of Adeno-associated virus (AAV) for the delivery of donor templates, are approaching the field of gene editing for the treatment of a variety of diseases (Dever, Bak et al. 2016, Bak, Dever et al. 2018, Charlesworth, Camarena et al. 2018, Pavel-Dinu, Wiebking et al. 2019). In this sense we have set up this approach to correct PKD and found that up to 40% of human hematopoietic progenitors have been gene edited with a therapeutic RPK (R-type pyruvate kinase) locus through combining specific RNP and AAVs. These results suggest that the clinical use of gene editing therapy to correct PKD is likely, however, the most concerning issue of this new gene editing technology to be applied to the clinic is the off-target effect caused by the RNP. Although the use of high-fidelity Cas9 has reduced the off-target activity, yet, there is still a need to significantly reduce the off-target effects prior to using gene editing to treat patients.

For this purpose, and to avoid off-target effects, the double-strand break (DSB) should be located as closely as possible to the place where the exogenous DNA is going to be integrated. The sgRNA determines this position, more particularly, the crRNA. In this sense, the sgRNA, more particularly the crRNA, needs to be carefully selected to maximize an on-target cut and minimize off-target effects. Homology Arms should be around the site of the DSB. They need to be designed in accordance with the sgRNA selected to maintain functions and avoid additional sequence changes.

In the present invention, the design of the different single guide RNAs to introduce DSBs in the genomic sites of interest was performed using the different web tools available for that purpose (see example 1). Efficacy to make DSBs of the different crRNAs (SEQ ID NO 1 to 10) obtained was tested, and these were evaluated by Surveyor assay, TIDE and/or GUIDE-Seq and rhAmp-Seq. The results indicated that only one of the selected crRNAs produced a very high frequency of indels at On-target site in K562 cells, a very high frequency of indels at On-target site in human CB-CD34+ cells, and although this specific crRNA showed several Off-targets when it was transfected in HEK293-Cas9 and Jurkat cells, these were almost negligent when HiFi-Cas9 RNP was used. Such crRNA corresponds to crRNA SG1 of SEQ ID NO 1 (as DNA) or SEQ ID NO 11 (as RNA). It is important to note that such crRNA (SG1) was due to an error at the time of selecting the proper ATG start codon of the RPK transcript variant as shown in example 1. In this sense, the fact that such crRNA SG1 showed a clear improved effect when compared to the different crRNAs tested was surprising. In fact, such crRNA SG1 showed a clear improved effect when compared to the different crR-NAs identified around a cryptic ATG located 30 bp upstream from the RPK start codon and also to those designed (SG5 to SG8), between the cryptic ATG and the proper ATG RPK start site in order to correct the previously mentioned designing lapse or error, since to avoid off-target effects, the double-strand break (DSB) should be located as closely as possible to the place where the exogenous DNA is going to be integrated. Based on these results, we proposed herein the use of the crRNA of SEQ ID NO 1 or SEQ ID NO 11 to provide a novel RNP complex for use in gene editing therapy to correct PKD in order to eliminate or reduce the off-target effects caused by the RNP.

In this sense, in contrast to other methods, the RNP complex presented herein significantly reduces the percent-age of off-target effects. On the whole, the present invention offers evidence of a RNP complex which, together with the use of Adeno-associated virus (AAV) for the delivery of the coRPK donor sequence of the present invention, is espe-cially suitable as an ex vivo effective genome editing tool able to achieve gene correction in many different cell types, providing a source to develop different cell therapies for Pyruvate Kinase Deficiency (PKD).

Consequently, in a first aspect of the invention, we herein provide a modified crRNA comprising or consisting of SEQ ID NO 1 or 11. In other instances, the modified crRNA of the present invention is a variant of SEQ ID NO 1 or SEQ ID NO 11 having at least 80%, 85%, 90% or 95% sequence identity to SEQ ID NO 1 or SEQ ID NO 11, e.g., 95%, 96%, 97%, 98%, 99%, or 100% sequence identity to SEQ ID NO 1 or SEQ ID NO 11. (From hereinafter SEQ ID NO 1, SEQ ID NO 11 as well as any variants thereof shall be referred to as the modified crRNA of the present invention).

Preferably, the modified crRNA of the present invention is associated or bound to a tracrRNA nucleotide sequence or to a linker that interacts with a CRISPR-associated protein (Cas) polypeptide (it is herein noted that the modified crRNA of the present invention associated with tracrRNA shall be referred to as the modified single guide RNA (sgRNA) of the present invention). Preferably, the modified sgRNA of the present invention comprises or consists of SEQ ID NO 12 or a variant of SEQ ID NO 12 having at least 80%, 85%, 90% or 95% sequence identity to SEQ ID NO 12, e.g., 95%, 96%, 97%, 98%, 99%, or 100% sequence identity to SEQ ID NO 12.

A second aspect of the invention refers to a ribonucleo-protein (RNP) comprising the modified crRNA or sgRNA of the present invention and a CRISPR-associated protein (Cas) polypeptide. For instance, the modified sgRNA and the Cas polypeptide can be mixed together in a vessel to form the RNP complex of the present invention, and then the RNP complex can be introduced into a primary cell.

In other embodiments, the invention refers to an "All RNA" CRISPR system comprising an mRNA encoding a Cas polypeptide and the modified sgRNA of the present invention.

A third aspect of the invention refers to a vector com-prising a coRPK cDNA sequence comprising homologous arms (LHA and RHA), a coRPK sequence and a specialized termination sequence for protein expression in eukaryotic cells such as the bGH poly(A) sequence; wherein, prefer-ably, LHA is SEQ ID NO 13, RHA is SEQ ID NO 14, the coRPK sequence is SEQ ID NO 16 and the bGH poly(A) sequence is SEQ ID NO 18. Preferably, the coRPK sequence of the present invention comprises or consists of SEQ ID NO 16 or a variant of SEQ ID NO 16 having at least 80%, 85%, 90% or 95% sequence identity to SEQ ID NO 16, e.g., 95%, 96%, 97%, 98%, 99%, or 100% sequence identity to SEQ ID NO 16. Preferably, the LHA sequence of the present inven-tion comprises or consists of SEQ ID NO 13 or a variant of SEQ ID NO 13 having at least 80%, 85%, 90% or 95% sequence identity to SEQ ID NO 13, e.g., 95%, 96%, 97%, 98%, 99%, or 100% sequence identity to SEQ ID NO 13. Preferably, the RHA sequence of the present invention comprises or consists of SEQ ID NO 14 or a variant of SEQ ID NO 14 having at least 80%, 85%, 90% or 95% sequence identity to SEQ ID NO 14, e.g., 95%, 96%, 97%, 98%, 99%, or 100% sequence identity to SEQ ID NO 14. Preferably, the bGH poly(A) sequence of the present invention comprises or consists of SEQ ID NO 18 or a variant of SEQ ID NO 18 having at least 80%, 85%, 90% or 95% sequence identity to SEQ ID NO 18, e.g., 95%, 96%, 97%, 98%, 99%, or 100% sequence identity to SEQ ID NO 18.

In some instances, the vector comprising a coRPK cDNA sequence of the present invention further comprises a 5'UTR sequence, wherein preferably such sequence is SEQ ID NO 15. More preferably, said vector comprising a coRPK cDNA sequence comprises SEQ ID NO 15 or a variant of SEQ ID NO 15 having at least 80%, 85%, 90% or 95% sequence identity to SEQ ID NO 15, e.g., 95%, 96%, 97%, 98%, 99%, or 100% sequence identity to SEQ ID NO 15.

In further instances, the vector comprising a coRPK cDNA comprises or consists of any of SEQ ID NO 19 to 22 or a variant of SEQ ID NO 19 to 22 having at least 95% sequence identity to any of SEQ ID NO 19 to 22, e.g., 95%, 96%, 97%, 98%, 99%, or 100% sequence identity to any of SEQ ID NO 19 to 22.

A fourth aspect of the invention refers to a system comprising the RNP complex of the present invention or the All RNA CRISPR system of the invention and an adeno-associated viral particle or homologous donor AAV that can deliver a recombinant donor template for CRISPR-based gene editing via homology-directed repair in a target cell, e.g., primary cell. In some instances, said adeno-associated viral or homologous donor AAV backbone, such as (AAV-6) or (AAV-1) or any other possible AAV serotypes or serotype chimeras, has at least about 90% sequence identity to an AAV backbone. It is noted that in the present invention AAV backbone is understood as the adeno-associated viral particle or homologous donor AAV without comprising the recombinant donor template of the present invention for CRISPR-based gene editing via homology-directed repair in a target cell. In other instances, the AAV backbone is a wild-type AAV6 or an AAV6 variant having at least 95% sequence identity to SEQ ID NO 23, e.g., 95%, 96%, 97%, 98%, 99%, or 100% sequence identity to SEQ ID NO 23. In some embodiments, polynucleotides encoding one or more of the various components of the AAV backbone, such as (AAV-6) or (AAV-1) or any other possible AAV serotypes or serotype chimeras, vector are operably linked to an inducible promoter, a repressible promoter, or a constitutive promoter. In addition, regulatory sequences operably linked to the components can include activator binding sequences, enhancers, introns, polyadenylation recognition sequences, promoters, repressor binding sequences, stem-loop structures, translational initiation sequences, translation leader sequences, transcription termination sequences, translation termination sequences, primer binding sites, and the like. Commonly used promoters are constitutive mammalian promoters CMV, EF1a, SV40, PGKI (mouse or human), Ubc, CAG, CaMKIIa, and beta-Act, and others known in the art (Khan, K. H. (2013) "Gene Expression in Mammalian Cells and its Applications," Advanced Pharmaceutical Bulletin 3 (2), 257-263). Further, mammalian RNA polymerase III promoters, including H1 and U6, can be used.

In some embodiments, said adeno-associated viral particle or homologous donor comprises an AAV backbone and a coRPK cDNA sequence of the present invention to be delivered to the primary cell. More preferably, the adeno-associated viral particle or homologous donor AAV comprises any of SEQ ID NO 19 to 22 or a variant of SEQ ID NO 19 to 22 having at least 95% sequence identity to any of SEQ ID NO 19 to 22, e.g., 95%, 96%, 97%, 98%, 99%, or 100% sequence identity to any of SEQ ID NO 19 to 22.

More preferably, the adeno-associated viral particle or homologous donor AAV comprising a vector which in turn comprises a coRPK cDNA sequence of the present invention is selected from any of SEQ ID NO 24 to 27 or a variant of SEQ ID NO 24 to 27 having at least 95% sequence identity to any of SEQ ID NO 24 to 27, e.g., 95%, 96%, 97%, 98%, 99%, or 100% sequence identity to any of SEQ ID NO 24 to 27.

Furthermore, in a fifth aspect of the invention, we herein provide a method for inducing a stable gene modification in a primary cell that comprises a target nucleic acid comprising a PKLR gene which in turn comprises one or more mutations in the PKLR gene and a nucleotide sequence that is complementary to SEQ ID NO 1 or 11, via homologous recombination in said primary cell, preferably in hematopoietic stem and progenitor cells (HSPC), or embryonic stem cells (ESC) or induced pluripotent stem cells (iPSC), or in any other cell type, which might be differentiated to HSPC or erythroid cells, wherein said method comprises:
  (a) introducing into the primary cell a composition that comprises the modified crRNA or sgRNA of the invention associated to a CRISPR-associated protein (Cas) polypeptide, or the "All RNA" CRISPR system of the invention; and simultaneously or sequentially
  (b) introducing into the primary cell an adeno-associated viral particle or homologous donor AAV comprising a coRPK cDNA sequence of the invention corresponding to the target nucleic acid to undergo homologous recombination;

wherein, the stable gene modification of the target nucleic acid comprises the compensation of disease-causing mutations of the PKLR gene (target nucleic acid), by introducing the homologous donor AAV, such as (AAV-6) or (AAV-1) or any other possible AAV serotypes or serotype chimeras, vector comprising the correction donor template.

The above-mentioned gene modification strategy in a primary cell, preferably in hematopoietic stem and progenitor cells (HSPC), or embryonic stem cells (ESC) or induced pluripotent stem cells (iPSC), or in any other cell type, which might be differentiated to HSPC or erythroid cells, is performed with the aim of treating a subject having or suffering from Pyruvate kinase deficiency (PKD). It is noted that Pyruvate kinase deficiency (PKD) is an inherited autosomal recessive disorder caused by mutations in the PKLR gene, which constitutes the main cause of chronic non-spherocytic hemolytic anemia. It is estimated that 1 in 20,000 people world-wide suffer from PKD, around 17% of whom have no curative treatment yet. PKLR gene encodes the erythroid pyruvate kinase protein (RPK) implicated in the last step of the anaerobic glycolysis in red blood cells. These PKD-causing mutations lead to a total or partial reduction in the RPK activity and the following reduction in the ATP levels, which favors RBC hemolysis and the consequent anemia. The disease becomes clinically relevant when the protein activity decreases below 25% of the normal activity in erythrocytes.

Therefore, in further embodiments of the fifth aspect of the invention, the homologous donor AAV comprises a coRPK cDNA sequence, such as SEQ ID NO 16, more preferably, said donor template comprises the coRPK cDNA sequence and two homologous portions of the target nucleic acid, such as SEQ ID NO 13 and 14.

In some embodiments, the primary cell is selected from the group consisting of a primary HSPCs, or embryonic stem cells (ESC) or induced pluripotent stem cells (iPSC), or in any other cell type, which might be differentiated to HSPC or erythroid cells, and any combination thereof. In some embodiments, the primary cell is isolated from a mammal prior to introducing the modified crRNA or sgRNA of the invention associated to a CRISPR-associated protein (Cas) polypeptide, or the "All RNA" CRISPR system of the invention, and the homologous donor AAV vector into the primary cell. For instance, the primary cell can be harvested from a human subject. In some instances, the primary cell or a progeny thereof is returned to the mammal after introducing the modified crRNA or sgRNA of the invention associated to a CRISPR-associated protein (Cas) polypeptide, or the "All RNA" CRISPR system of the invention, and the homologous donor AAV vector into the primary cell. In other words, the genetically modified primary cell undergoes autologous transplantation. In other instances, the genetically modified cell undergoes allogeneic transplantation. For example, a cell that has undergone not stable gene modification is isolated from a donor subject, and then the genetically modified donor cell is transplanted into a recipient subject who is different from the donor subject.

The primary cell can comprise a population of primary cells. In some cases, the population of primary cells comprises a heterogeneous population of primary cells. In other cases, the population of primary cells comprises a homogeneous population of primary cells.

In still other instances, the homologous donor AAV backbone, such as (AAV-6) or (AAV-1), has at least about 90% sequence identity to an AAV backbone. In other instances, the homologous donor AAV backbone is a wild-type AAV6 or an AAV6 backbone variant having at least 95% sequence identity to SEQ ID NO 23, e.g., 95%, 96%, 97%, 98%, 99%, or 100% sequence identity to SEQ ID NO 23. In some embodiments, polynucleotides encoding one or more of the various components of the AAV backbone, such as (AAV-6) or (AAV-1), vector are operably linked to an inducible promoter, a repressible promoter, or a constitutive promoter. In addition, regulatory sequences operably linked to the components can include activator binding sequences, enhancers, introns, polyadenylation recognition sequences, promoters, repressor binding sequences, stem-loop structures, translational initiation sequences, translation leader sequences, transcription termination sequences, translation termination sequences, primer binding sites, and the like. Commonly used promoters are constitutive mammalian promoters CMV, EF1a, SV40, PGKI (mouse or human), Ubc, CAG, CaMKIIa, and beta-Act, and others known in the art (Khan, K. H. (2013) "Gene Expression in Mammalian Cells and its Applications," Advanced Pharmaceutical Bulletin 3(2), 257-263). Further, mammalian RNA polymerase III promoters, including HI and U6, can be used.

In some embodiments, the homologous donor AAV backbone is capable of preferentially directing expression of the nucleic acid in a particular cell type (e.g., using tissue-specific regulatory elements to express a polynucleotide). Tissue-specific regulatory elements are known in the art and include, but are not limited to, the albumin promoter, lymphoid-specific promoters, neuron-specific promoters (e.g., the neurofilament promoter), pancreas-specific promoters, mammary gland-specific promoters (e.g., milk whey promoter), and in particular promoters of T cell receptors and immunoglobulins. Developmentally-regulated promoters are also encompassed, e.g., the murine hox promoters and the alpha-fetoprotein promoter.

Methods of introducing the AAV, such as (AAV-6) or (AAV-1), expression vector into host cells are known in the art and are typically selected based on the kind of host cell.

In some embodiments, the stable gene modification of the target nucleic acid is induced in greater than about 30% of the population of primary cells, e.g., about 35%, about 40%, about 50%, about 60%, about 70% about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% of the population of primary cells. In other embodiments, the stable gene modification of the target nucleic acid is induced in greater than about 80% of the population of primary cells, e.g., about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% of the population of primary cells. In yet other embodiments, the stable gene modification of the target nucleic acid is induced in greater than about 90% of the population of primary cells, e.g., about 90%, about 91%, about 92%, about 93%, about 94%, about 95%, about 96%, about 97%, about 98%, about 99%, or about 100% of the population of primary cells.

In some embodiments, the sequences of the fifth aspect of the invention may comprise modified nucleotides such as a modification in a ribose group, a phosphate group, a nucleobase, or a combination thereof. In some instances, the modification in the ribose group comprises a modification at the 2' position of the ribose group. In some cases, the modification at the 2' position of the ribose group is selected from the group consisting of 2'-O-methyl, 2'-fluoro, 2'-deoxy, 2'-O-(2-methoxyethyl), and a combination thereof. In other instances, the modification in the phosphate group comprises a phosphorothioate modification. In other embodiments, the modified nucleotides are selected from the group consisting of a 2'-O-methyl (M) nucleotide, a 2'-O-methyl 3'-phosphorothioate (MS) nucleotide, a 2'-O-methyl 3'-thioPACE (MSP) nucleotide, and a combination thereof.

Preferably, for all aspects and embodiments of the present invention, the Cas polypeptide is a Cas9 polypeptide or a high-fidelity or enhanced specificity Cas9 polypeptide variant. In certain embodiments, the modified sgRNA of the present invention and the Cas polypeptide are introduced into the primary cell concomitantly. In other embodiments, the modified sgRNA and the Cas polypeptide are introduced into the primary cell sequentially. In some cases, the modified sgRNA is introduced first, and the Cas polypeptide thereafter. In other cases, the Cas polypeptide is introduced first, and the modified sgRNA of the present invention thereafter.

In some embodiments, the Cas polypeptide described herein can be an mRNA encoding the Cas polypeptide, which Cas mRNA is introduced into the primary cell together with the modified gRNA of the present invention as an "All RNA" CRISPR system. In certain instances, the modified gRNA of the present invention and the Cas mRNA are introduced into the primary cell concomitantly. In other instances, the modified gRNA and the Cas mRNA are introduced into the primary cell sequentially. In some cases, the modified gRNA of the present invention is introduced first, and the Cas mRNA thereafter. In other cases, the Cas mRNA is introduced first, and the modified gRNA of the present invention thereafter.

In some embodiments, the RNP complex and the homologous donor AAV, such as (AAV-6) or (AAV-1), vector are concomitantly introduced into the primary cell. In other embodiments, the RNP complex and the homologous donor AAV vector are sequentially introduced into the primary cell. In some instances, the RNP complex is introduced into the primary cell before the homologous donor AAV vector. In other instances, the homologous donor AAV vector is introduced into the primary cell before the RNP complex. For example, the RNP complex can be introduced into the primary cell about 1, 2, 3, 4, 5, 6, 7, 8, 9, 10, 11, 12, 13, 14, 15, 16, 17, 18, 19, 20, 25, 30, 35, 40, 45, 50, 55, 60, 90, 120, 150, 180, 210, or 240 minutes or more before the homologous donor AAV vector, or vice versa. In particular embodiments, the RNP complex is introduced into the primary cell about 15 minutes (e.g., from about 10 to about 20 minutes) before the homologous donor AAV vector.

In some embodiments, the "All RNA" CRISPR system and the homologous donor AAV vector are concomitantly introduced into the primary cell. In other embodiments, the "All RNA" CRISPR system and the homologous donor AAV vector are sequentially introduced into the primary cell. In some instances, the "All RNA" CRISPR system is introduced into the primary cell before the homologous donor AAV vector. In other instances, the homologous donor AAV vector is introduced into the primary cell before the "All RNA" CRISPR system. For example, the "All RNA" CRISPR system can be introduced into the primary cell about 1, 2, 3, 4, 5, 6, 7, 8, 9, 10, 11, 12, 13, 14, 15, 16, 17, 18, 19, 20, 25, 30, 35, 40, 45, 50, 55, 60, 90, 120, 150, 180, 210, or 240 minutes or more before the homologous donor AAV vector, or vice versa. In particular embodiments, the "All RNA" CRISPR system is introduced into the primary cell about 15 minutes (e.g., from about 10 to about 20 minutes) before the homologous donor AAV vector.

In some embodiments, any of the methods described herein can also include purifying the primary cell having the stable gene modification of the target nucleic acid using the marker. In some cases, the composition isolated by the purifying step includes at least about 80% primary cells having the stable gene modification of the target nucleic acid, e.g., about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more primary cells having the stable gene modification of the target nucleic acid.

In some embodiments, the step of introducing the modified gRNA of the present invention and the Cas polypeptide into the primary cell comprises electroporating the modified gRNA and the Cas polypeptide into the primary cell. In some embodiments, the step of introducing the homologous donor AAV, such as (AAV-6) or (AAV-1), vector into the primary cell comprises transducing the primary cell.

In other aspects, provided herein is a genetically modified primary cell produced by any of the methods described herein. In some embodiments, the genetically modified primary cell is selected from the group consisting of HSPCs, or embryonic stem cells (ESC) or induced pluripotent stem cells (iPSC), or in any other cell type, which might be differentiated to HSPC or erythroid cells, or any combination thereof.

In yet other aspects, provided herein is a pharmaceutical composition comprising any of the genetically modified primary cells described herein, and a pharmaceutically acceptable carrier. In other embodiments, the pharmaceutical composition comprises one type of genetically modified primary cell. In other embodiments, the pharmaceutical composition comprises two or more different types of genetically modified primary cells, e.g., 2, 3, 4, 5, 6, 7, 8, 9, 10 or more different types of genetically modified primary cells.

In further aspects, provided herein is the in vitro use of a kit comprising (a) the modified crRNA or sgRNA of the invention associated to a CRISPR-associated protein (Cas) polypeptide, or the "All RNA" CRISPR system of the invention; and/or (b) an adeno-associated viral particle or homologous donor AAV comprising a coRPK cDNA sequence of the invention corresponding to a target nucleic acid to undergo homologous recombination.

In some instances, the kit also contains a reagent for harvesting or isolating a primary cell from a subject. The subject can be a mammalian subject, e.g., a human subject.

In yet further aspects, provided herein is method of preventing or treating PKD in a subject in need thereof, the method comprising administering to the subject any of the genetically modified primary cells described herein, or any of the pharmaceutical compositions described herein, to prevent the disease or ameliorate one or more symptoms of the disease.

In some embodiments, the step of administering comprises a delivery route selected from the group consisting of intravenous, intraperitoneal, intraosseous, or a combination thereof.

In particular embodiments, the genetically modified primary cells or pharmaceutical compositions of the present invention are administered to the subject in a sufficient amount to correct a mutation in the target nucleic acid that is associated with the disease. In some instances, the mutation is corrected by replacing a mutant allele in the target nucleic acid with the wild-type allele.

Other objects and advantages of the invention will become apparent to those skilled in the art from a review of the ensuing detailed description, which proceeds with reference to the following illustrative drawings, and the attendant claims.

Consequently, the applicants have herein shown the use of the CRISPR system to definitely repair the PKD mutation. Applicants target sites around the mutated site. DNA repair of PKD's disease mutation using the CRISPR/Cas9 system represents a new and original therapeutic approach. The present invention offers the possibility to act at the DNA level with engineered nucleases to inactivate or repair a disease-causing mutation.

The following examples are merely illustrative and do not limit the scope of the present invention.

EXAMPLES

The present examples are meant to exemplified the different elements that integrate a procedure that shall require the ex vivo expansion of HSPCs for 16, 24 or 48 hours in the presence of hematopoietic cytokines and the introduction of a i) system to generate the double strand breaks of the DNA (DSBs), such as the CRISPR/Cas9 system, upstream of the transcription start site of the RPK transcript variant of the PKLR gene, and ii) the introduction of a donor matrix that includes a coRPK cDNA flanked by homology arms (Left [LHA] and right [RHA]). LHA and RHA are identical to the genomic sequences where the exogenous sequences will be inserted. The coRPK cDNA used herein is preceded by part of 5'UTR RPK sequence to express the therapeutic cassette under the endogenous regulation. The CRISPR/Cas9 shall be introduced by electroporation to favor the access of DNA nucleases into the cell nucleus, and the donor matrix shall be introduced by means of and adenoassociated viral vector serotype 6 (AAV-coRPK). To assemble the ribonucleoproteins (RNP), Cas9 protein is combined with the sgRNA. For the nuclefection of RNP into the cell, an electroporator device is used. Cells are pre-stimulated then resuspended in electroporation solution. RNP complex is added into the cellular suspension and the cells are electroporated. After the electric pulse, HSPCs are incubated for 10 minutes at 37° C. Then, a pre-warmed medium is added, and cells are transferred to a culture plate. Nucleofected cells are immediately transduced with the corresponding AAV at different concentrations.

The cells, Hematopoietic Stem Cells (HSC) are therefore obtained from a patient, manipulated in vitro, freeze and once the product has been characterized and demonstrated that is correct, the cells shall be thawed and infused in the patient that has been previously conditioned with chemotherapy to allow the engraftment of the infused corrected cells.

Example 1. Design of the CRISPR/Cas9 System of the Present Invention sgRNA:
1. sgRNA Design:
Following the previous reports, sgRNAs to introduce DSBs and to promote knock-in integration at the beginning of the gene should be designed as close as possible to the start codon of RPK transcript variant of the gene. Designing of crRNAs was performed using the different web tools available for that purpose, such as Dr. Zhang's lab tool (zlab.bio/guide-design-resources), or IDT's tool (eu.idtdna-.com/site/order/designtool/index/CRISPR_SEQUENCE). Due to an error at the time of selecting the proper ATG start codon of the RPK transcript variant, different crRNAs were identified around a cryptic ATG located 30 bp upstream from the RPK start codon. Those first designed crRNAs were SG1 to SG4. Additionally, more crRNAs were designed (SG5 to SG8), between the cryptic ATG and the proper ATG RPK start site in order to correct the previously mentioned designing lapse or error, since to avoid off-target effects, the double-strand break (DSB) should be located as closely as possible to the place where the exogenous DNA is going to be integrated.

TABLE 1

| Different crRNAs (as DNA) designed and analyzed | | |
|---|---|---|
| Name | SEQ ID NO 1 to 10). | PAM |
| SG1 | CTGCGGGACCATGGAATGAG | AGG |
| SG2 | TGGGGACAGGGTGGCCTACT | GGG |
| SG3 | AAAACTGCTGGTCTTATCTA | AGG |
| SG4 | AGAAAAGGGGCACACCCAGT | AGG |
| SG5 | TGGTCCCGCAGCCCCAGGCC | TGG |
| SG6 | CTCCCTCTCATTCCATGGTC | AGG |
| SG7 | CAGCCCCAGGCCCACACTGA | CGG |
| SG8 | TTCCATGGTCCCGCAGCCCC | AGG |
| SG9 | CACTGAAAGCATGTCGATCC | AGG |
| SG10 | AAACTGCTGGTCTTATCTAA | GGG |

2. sgRNA Efficacy and Safety:

Efficacy to make DSBs of the different 10 sgRNAs (SEQ ID NO 1 to 10) of table 1 was evaluated by Surveyor assay, TIDE and/or GUIDE-Seq and rhAmp-Seq.

For Surveyor assay, genomic DNA was purified and a PCR was performed to amplify the region around the starting codon of RPK transcript variant. Then, the PCR products were digested with the Surveyor nuclease S according to the manufacturer's instructions, and the digested products were evaluated by separation on a 10% Novex TBE gel. Images from gels were analyzed in order to measure the cleavage by measuring the densitometry value of the different bands.

Additionally, Indel frequency of SG1, SG3, SG5, SG6 and SG8 were analyzed in human CB-CD34+ cells by TIDE assay. Genomic DNA was purified, and a PCR was performed to amplify the region around the starting codon of RPK transcript variant of the PKLR gene. Then, the PCR products were Sanger sequenced. Unedited cells were always used as a negative control for calculating Indel frequencies with TIDE. Finally, the activity of the designed guide was assessed through calculating the Indel frequencies using the TIDE software (tide.deskgen.com/).

Figure 4:
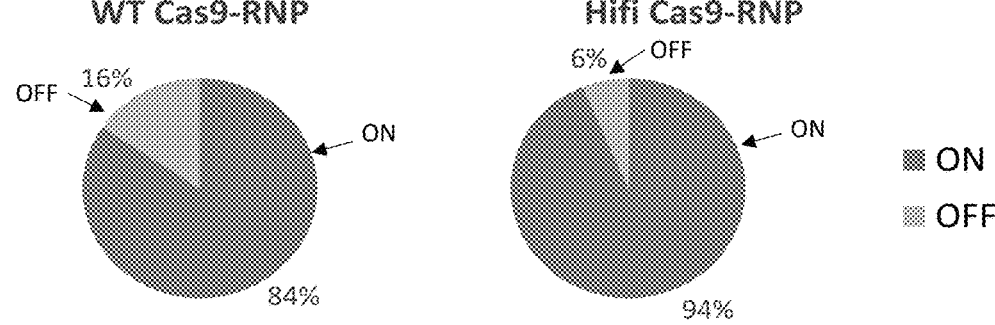
FIG. 4: Off-target analysis of selected single guideRNAs. GUIDE-seq analysis was performed in Jurkat cells electroporated with SG1 guide RNA in RNP format with either WT-Cas9 or HiFi-Cas9 proteins. Five days later, genomic DNA was isolated. Using IDT in-house guide analysis tool, 448 off-target sites were determined, whereof 147 of them appeared in >1% of the reads. 84% of the reads from the samples edited with WT-Cas9 RNP presented the specific on-target gene editing, and this percentage was increased when HiFi-Cas9 was used for the RNP formation (94% of Indels occurred in the on-target site), indicating that PKLR SG1 RNP was safe and efficient.
Figure 5:
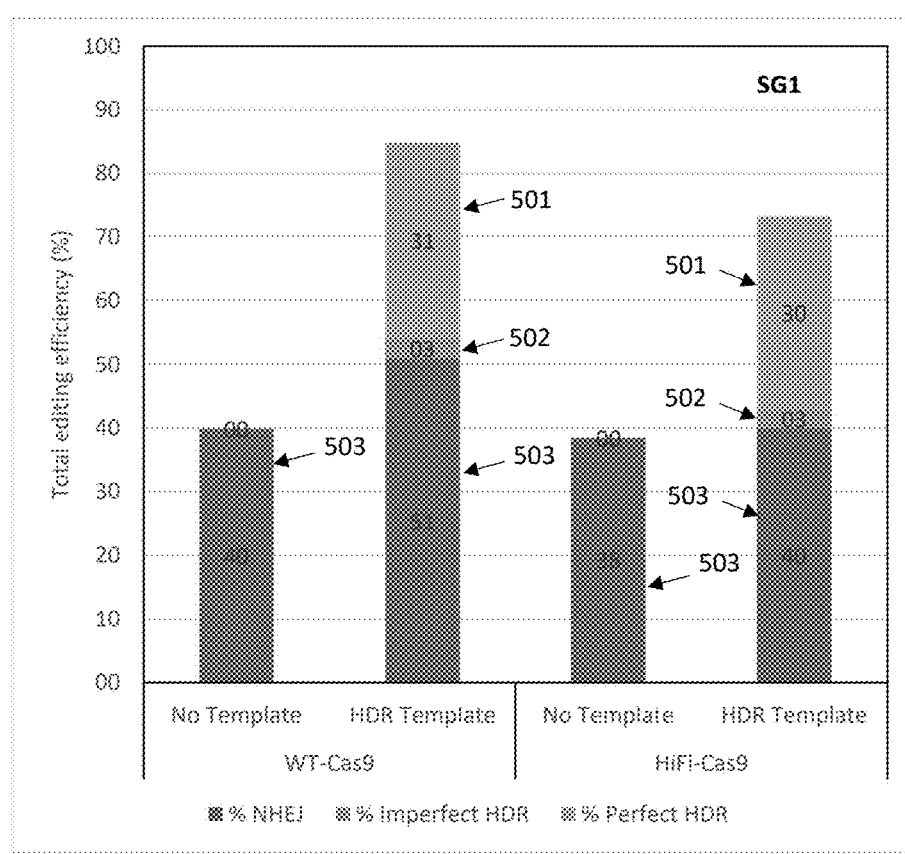
FIG. 5: Analyses of the HDR vs NHEJ at different on-target sites in hCD34⁺ cells edited with SG1, SG9 and SG10 RNPs (complexed with either WT-Cas9 or HiFi-Cas9). A rhAmpSeq assay was designed from FIG. 4. Briefly, top Hits (1 on-target site, ON, and 48 off-target site, OTs) from GUIDE-seq experiment using the PKLR SG1 were amplified with rhAmpSeq pool. Then, libraries were run on a MiSeq system and analyzed with the in-house analysis tool. Editing levels at the cutting site were calculated by adding the percentage of NHEJ, to the percentage of Imperfect HDR (homologous recombination of part of the HDR template) and the percentage of Perfect HDR (homologous recombination of the whole HDR template). SG1 RNP showed the highest gene editing activity at the on-target site. No differences were found in the levels of Perfect HDR when using WT- or HiFi-Cas9 (30.6% vs 30.4% respectively) although levels of NHEJ and imperfect HDR were reduced when HiFi-Cas9 was used. 501, percentage of perfect HDR; 502, percentage of imperfect HDR; 503, percentage of NHEJ.
Figure 5:
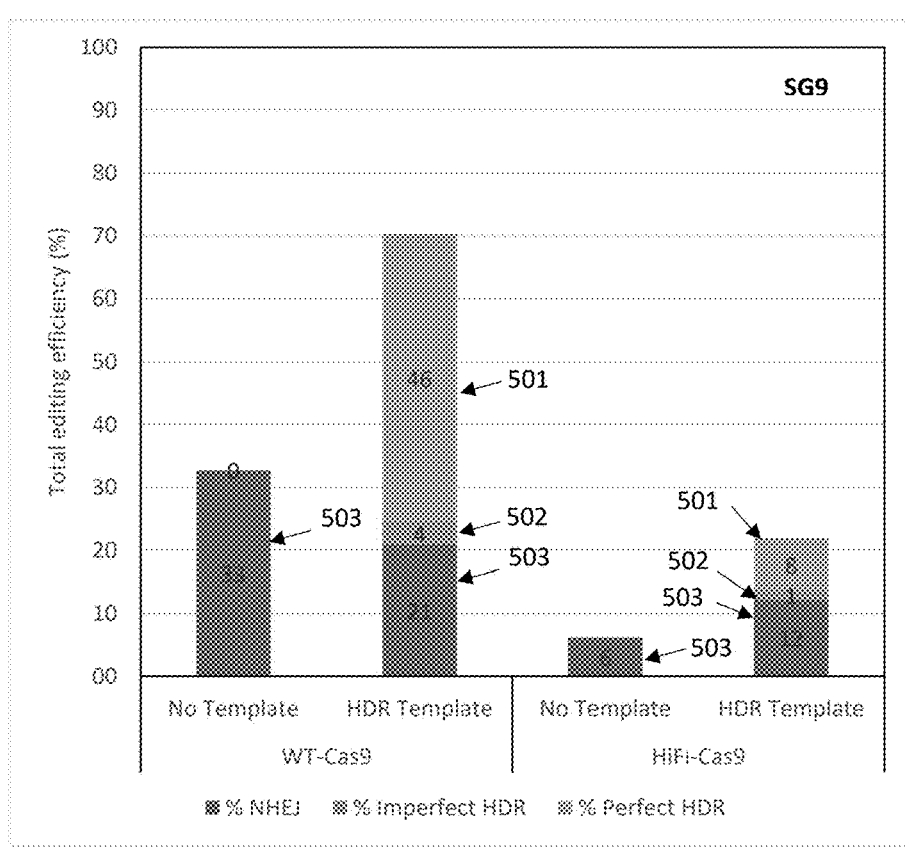
Figure 5:
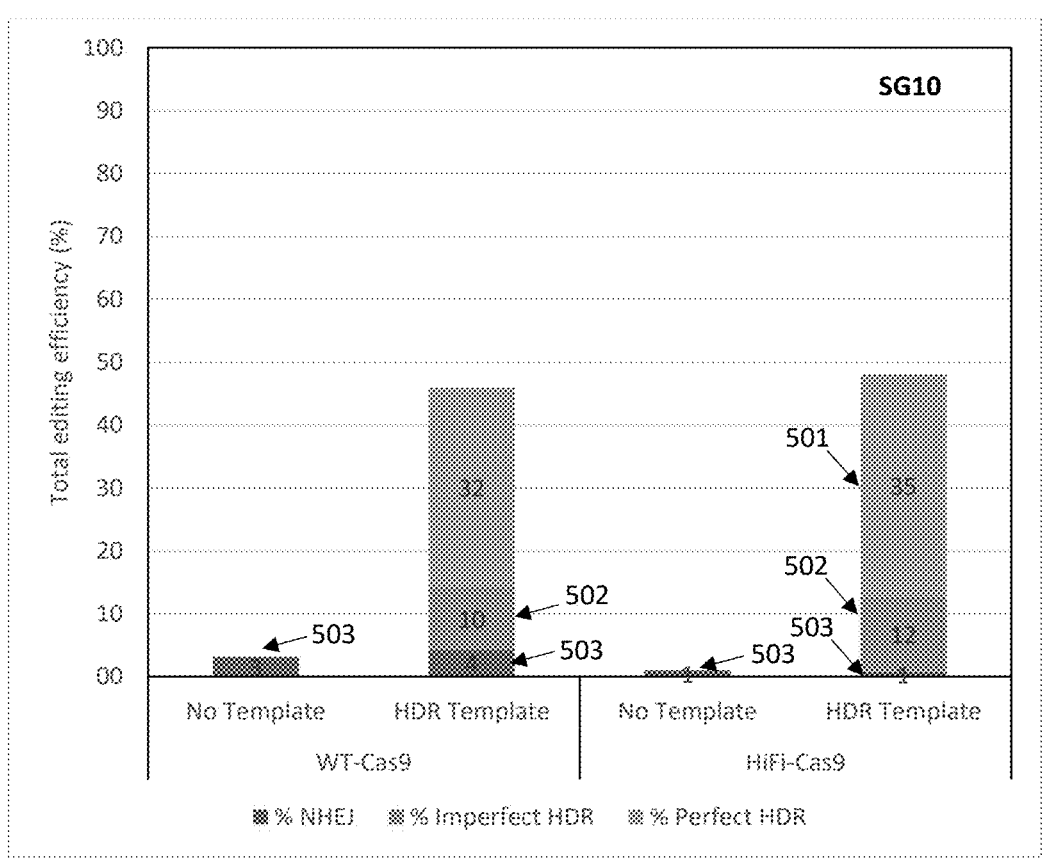
Figure 6:
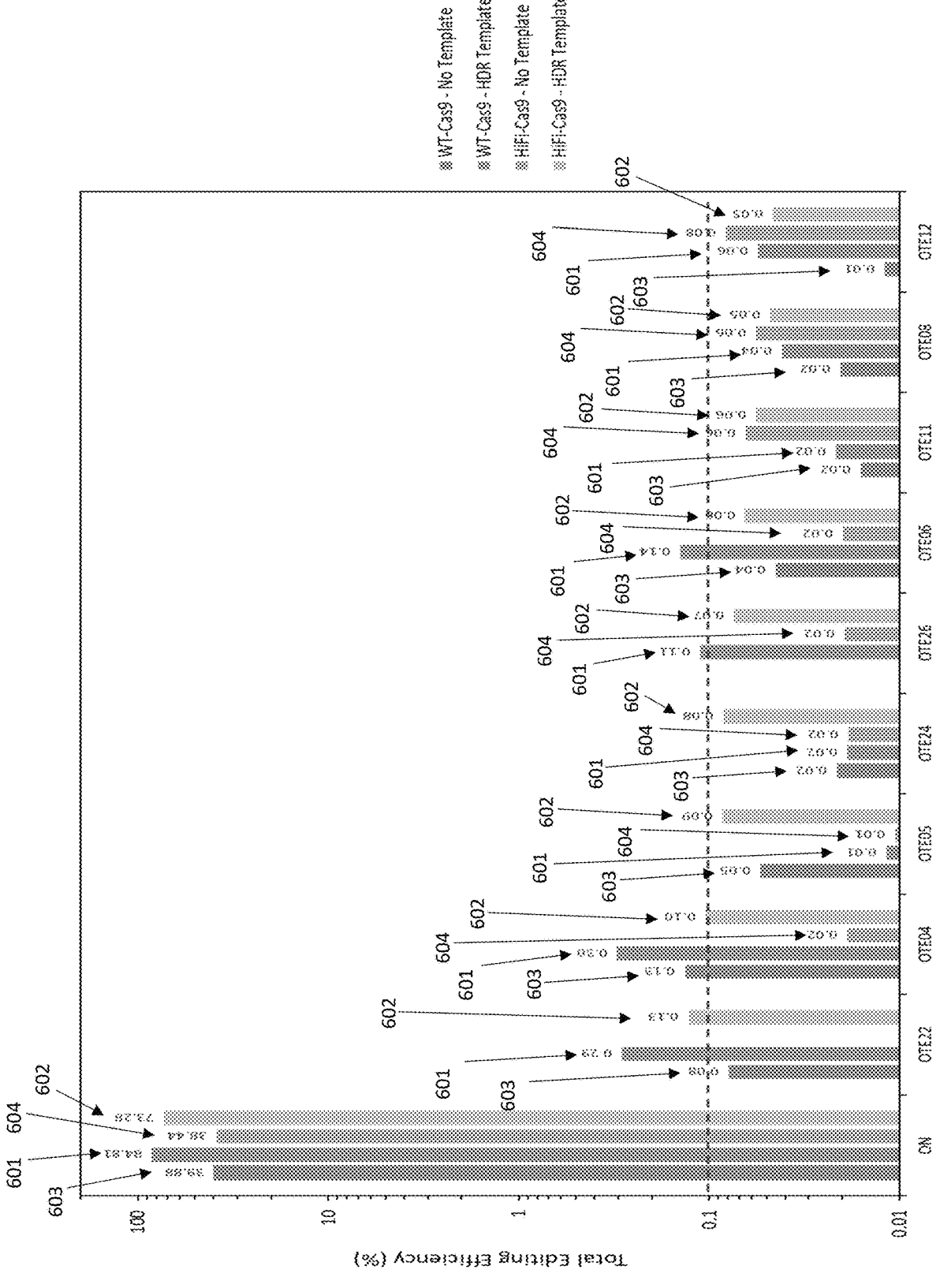
FIG. 6: Off-target analyses in CB-hCD34⁺ cells electroporated with SG1 RNP complex in the top ten sites ranked high-low. A rhAmpSeq assay was designed from FIG. 4. CB-hCD34⁺ cells were edited using SG1, single guide RNA complexed with either WT-Cas9 or HiFi-Cas9 (IDT) to form a RNP complex. Additionally, a specific HDR template was added in some of the samples. Top Hits (1 on-target site, ON and 48 off-target site, OTs) from GUIDE-seq experiment using the PKLR SG1 were amplified with rhAmpSeq pool. Then, libraries were run on a MiSeq system and analyzed with the in-house analysis tool. Total gene editing efficiency by RNP [WT- or HiFi-Cas9 HiFi+SG1 (PKLR SG1 ATG)] ±HDR-SG1 template in the top ten sites is represented. In 601 and 602, the gene editing caused by SG1 complexed with WT-Cas9 or HiFi-Cas9 respectively in the absence of the specific HDR template. In 603 and 604, the gene editing caused by SG1 complexed with WT-Cas9 or HiFi-Cas9 respectively in presence of the specific HDR template. The discontinuous line points the limits of detection (<0.1%). When HiFi-Cas9 was used, the number of off-target reads was considerably reduced (604 and 602) in comparison with the reads from WT-Cas9 editing (603 and 601 bars). In the absence of HDR template, all the reads corresponding to off-target sites were under the limits of detection (0.1%), and the highest off-target score achieved when cells were edited with SG1-Cas9 RNP and HDR template was 0.13%.

Furthermore, off-target activity of the three most promising sgRNAs (SG1, SG2 and SG3) together with newly designed sgRNAs (SG4, SG9 and SG10) was analyzed following the strictest criteria up to now, GUIDE-seq and rhAmpSeq, before the selection of one of them for its clinical use. Firstly, a GUIDE-seq Analysis was performed in a HEK293T cell line that constitutively expressed WT- Cas9 to extensively identify off-targets considering the genomic context in vivo. Cells were transfected with the different sgRNAs. Five days later, cells were collected, and genomic DNA was isolated. With IDT in-house guide analysis tool using a GUIDE-seq-tag, off-target sites were determined, whereof those appearing in >1% of the reads were also observed. The in vivo off-targets were identified for these sgRNAs and the representation of the modification of the on-target in the global gene editing was calculated (Table 3). However, when the same GUIDE-seq analysis was performed in Jurkat cells electroporated with SG1 in RNP format, the number of off-targets was reduced dramatically (FIG. 4). Moreover, the use of HiFi-Cas9 in the RNP complex shrank the off-target effect of SG1. In order to quantify on-target and off-target activity at the sites uncovered by the GUIDE-seq, on-target and off-target indel frequencies were measured by rhAmpSeq, this assay contributed to a more accurate quantitative analysis of gene editing of SG1 in a cell and genomic context. CB-CD34+ cells were edited using SG1 or SG9 or SG10, which showed a reduce off-target contribution (Table 3), complexed with either WT-Cas9 or HiFi-Cas9 to form a RNP complex. Additionally, a specific ssODN HDR template was added in some of the samples to determine the ability of each sgRNA to mediate in HDR. Top Hits (1 on-target site, ON, and 48 off-target site, OTs) from GUIDE-seq experiment were amplified with rhAmpSeq pool. Then, libraries were run on a MiSeq system and analyzed with an in-house analysis tool. Editing levels at the cut site were calculated by adding the percentage of NHEJ, to the percentage of Imperfect HDR and the percentage of Perfect HDR. As shown in FIG. 5, SG1 was confirmed to have the greatest gene editing activity at the on-target site. Moreover, the frequency of perfect HDR did not vary when HiFi-Cas9 was used to form the RNP complex. Therefore, the use of HiFi-Cas9 in the SG1 RNP complex did not hamper HDR at the target site. Additionally, the off-target effect of SG1 RNP in hCD34+ was analyzed (FIG. 6). The use of HiFi-Cas9 in the SG1 RNP reduced the modification of all the off-targets below 0.1, the limit of detection of the technique. Consequently, gene editing of hCD34+ cells with SG1 HiFi-Cas9 RNP complex maintained a high level of modification at the on-target site without altering HDR, and reduced the off-target effect to undetectable levels.

2.1. Surveyor Assay

Figure 2:
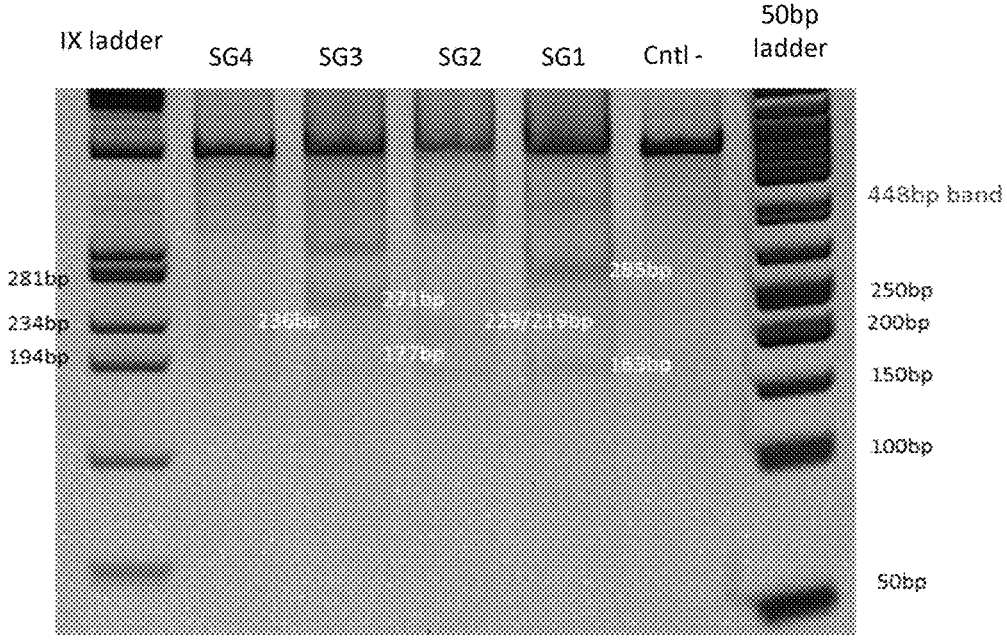
FIG. 2: Efficacy of different single guide RNAs recognizing the PKLR locus. Analysis of Indel (insertion/deletion) frequency of SG1, SG2, SG3 and SG4 guides in human cell line K562 by Surveyor assay. Genomic DNA was purified, and a PCR was performed to amplify the region around the starting codon of RPK gene. Then, the PCR products were digested with the Surveyor nuclease S according to manufacturer's instructions, and the digested products were evaluated by separation on a 10% Novex TBE gel. Images from gels were analyzed in order to measure the cleavage by measuring the densitometry value of the different bands.

The results provided by the Surveyor assay are shown in FIG. 2, in addition to table 2 below.

| | SG1 | SG2 | SG3 | SG4 |
|---|---|---|---|---|
| % Indels (Surveyor) | 23.12 | 11.12 | 12.99 | 0.67 |

Table 2: Indel quantification of SG1, SG2, SG3 and SG4 analyzed in human cell line K562 by Surveyor assay.

Results of the Surveyor Assay:

SG1 (SEQ ID NO 1) produced the highest frequency of indels at On-target site in K562 cells.

2.2. TIDE Assay

Figure 3:
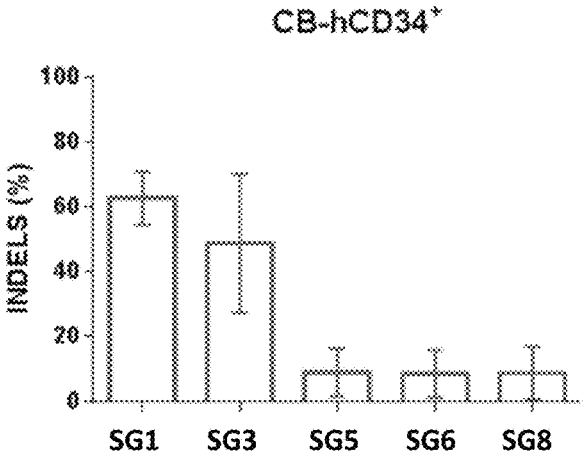
FIG. 3: Efficacy of Indel frequency of different single guide RNAs recognizing the PKLR locus. Analysis of Indel frequency of SG1, SG3, SG5, SG6 and SG8 analyzed in human CB-CD34⁺ cells by TIDE assay. Genomic DNA was purified, and a PCR was performed to amplify the region around the starting codon of RPK transcript variant of the PKLR gene. Then, the PCR products were Sanger sequenced. Unedited cells were always used as a negative control for calculating INDEL frequencies with TIDE. Finally, the activity of the designed guide was assessed through calculating the Indel frequencies using the TIDE software (tide.deskgen.com/).

The results provided by the TIDE assay are shown in FIG. 3.

Results of the TIDE Assay:

SG1 (SEQ ID NO 1) produced the highest frequency of indels at On-target site in human CB-CD34+ cells.

2.3. GUIDE-Seg and rhAmp-Seq:

Identification of in vivo Off-targets: GUIDE-seq Analyses in a HEK293 cell line that constitutively expressed WT-Cas9 (HEK293-Cas9) were performed to force the identification of in vivo off-targets.

variant, was cloned at 5' of coRPK cDNA without ATG and STOP codon in the coRPK-AAV. To note, there is a gap of

| Guide name | Sequence (5'-3') | Design tool | OTE sites detected | OTE sites >1% | On-target (%) |
|---|---|---|---|---|---|
| SG1 | CTGCGGGACCATGGAATGAG | MIT | 448 | 147 | 9.2 |
| SG2 | TGGGGACAGGGTGGCCTACT | MIT | 534 | 140 | 7.5 |
| SG3 | AAAACTGCTGGTCTTATCTA | MIT | 49 | 26 | 23.1 |
| SG9 | CACTGAAAGCATGTCGATCC | IDT | 7 | 0 | 100 |
| SG10 | AAACTGCTGGTCTTATCTAA | IDT | 28 | 9 | 73.3 |
| SG4 | AGAAAAGGGGCACACCCAGT | IDT | 554 | 116 | 11.3 |

Table 3: Number of Off-targets and percentage of On-target of SG1 (SEQ ID NO: 1), SG2 (SEQ ID NO: 2), SG3 (SEQ ID NO: 3), SG4 (SEQ ID NO: 4), SG9 (SEQ ID NO: 9) and SG10 (SEQ ID NO: 10) obtained in HEK293-Cas9 transfected with each sgRNA and analyzed with GUIDE-Seq.

Results:

SG1 (SEQ ID NO 1) showed several Off-targets when transfected in HEK293-Cas9. Results regarding the safety of PKLR SG1 ATG as Ribonucleoprotein (RNP) format, are shown in FIG. 4 and FIG. 6. Off-target effect derived of SG1 in hCD34+ was reduced below 0.1% when HiFi Cas9-RNP was used.

3. Quantitative On-Target Modification and Frequency of HDR by rhAmp-Seq

The results are shown in FIGS. 5, wherein the frequency of On-target was the highest in CB-CD34+ when SG1 was used. Additionally, high frequency of HDR of SG1 was not impaired when HiFi Cas9-RNP was used.

SEQ ID NO 1: protospacer SG1 sequence
CTGCGGGACCATGGAATGAG
SEQ ID NO 11: crRNA SG1 sequence (as RNA)
CUGCGGGACCAUGGAAUGAG
SEQ ID NO 12: sgRNA SG1 sequence (as RNA)
CUGCGGGACCAUGGAAUGAGGUUUUAGAGC-
UAGAAAUAGCAAGUUAAAUAAGGCUAGU-
CCG

Example 2. CoRPK-AAV's Design

Figure 7:
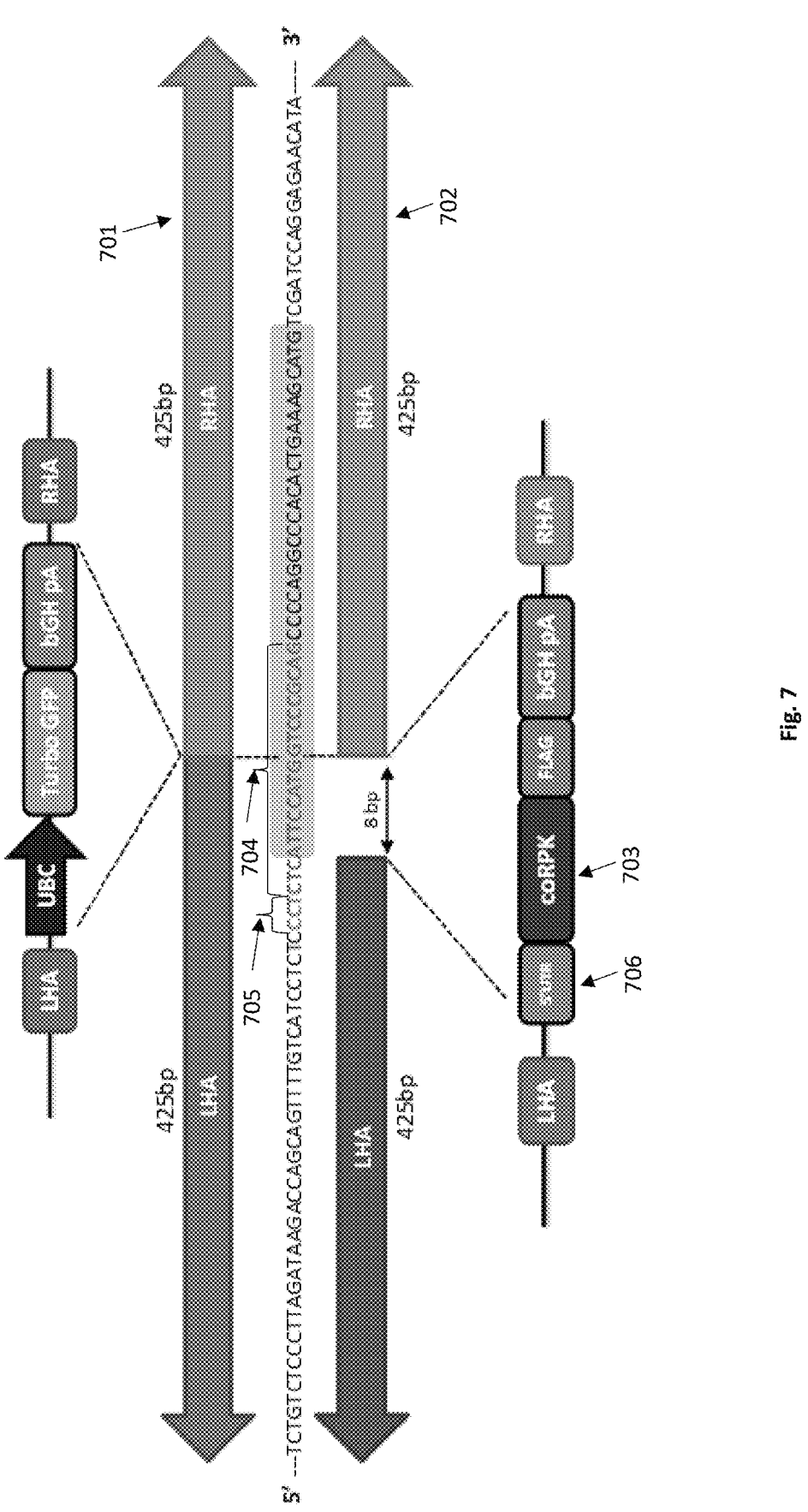
FIG. 7: Scheme of targeting reporter and therapeutic homologous donors to the PKLR locus. Two constructs were designed to perform knock-in of i) a reporter donor (upper part, 701) and ii) a therapeutic donor (lower part, 702), in the genomic starting site of RPK transcript variant (start codon of RPK [ATG], 703). The best guide RNA (704, SG1) resulted to cut 38 bp upstream the ATG site (PAM sequence, 705). In the case of reporter donor (upper part, 701), sequences of 425 bp in the cutting site vicinity were used as Homology Arms (HA), that were cloned into the AAV construct flanking the UBC promoter, turboGFP sequence and the polyadenylation signal of the bGH gene. In the case of the therapeutic donor (702), the sequence used as RHA was the same used in reporter donor to make the constructs as comparable as possible. In order to add part of the RPK 5'UTR sequence (706), the LHA was displaced 8 bp upstream, but the 425 bp size was maintained. LHA and RHA in the therapeutic donor flanked the construct containing the 5'UTR sequences, a codon optimized version of the RPK transcript variant (coRPK), a FLAG-Tag sequence and the polyadenylation signal of the bGH gene. SEQ ID NO: 29.
Figure 8:
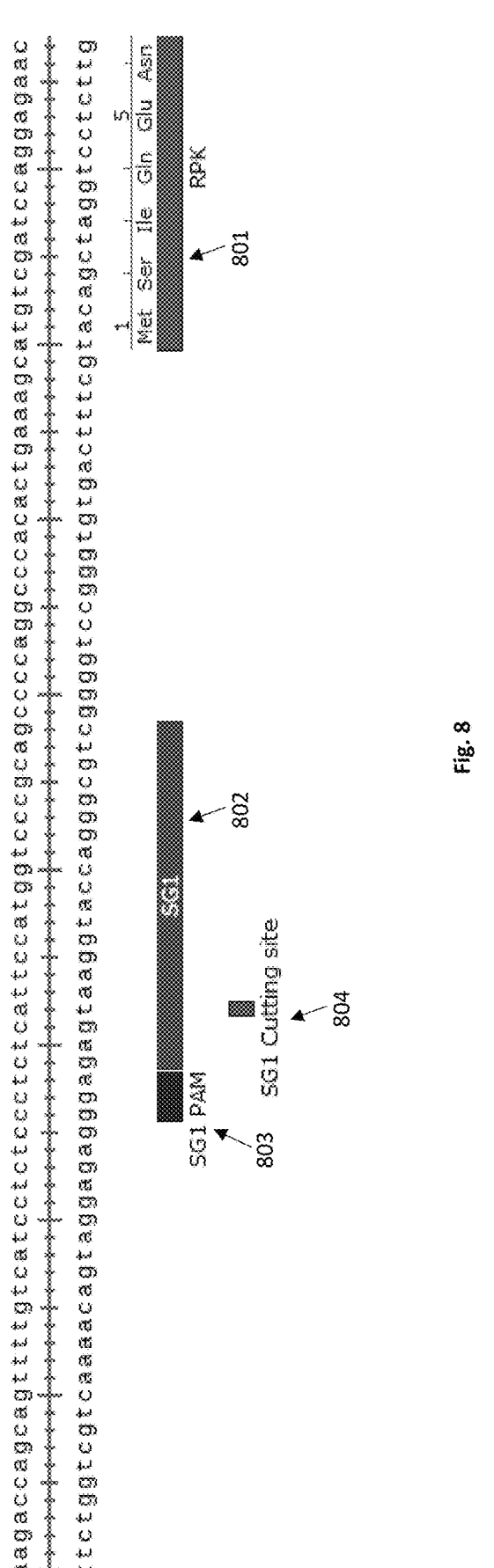
FIG. 8: SG1 (SEQ ID NO 1). On-target sequence. The figure represents the genomic region of the starting site of the RPK transcript variant, 801. The first 27 aminoacids of the protein are shown. The cutting site of SG1, 802, is at 38 bp upstream of RPK start codon. PAM sequence and cutting site of the SG1 is marked below, 803 and 804, respectively. The design of the different guide RNAs to introduce DSBs close to the transcription start site of the RPK transcript variant was performed using the different website tools available for that purpose, such as Dr. Zhang's lab tool (zlab.bio/guide-design-resources) or Integrated DNA Technologies (IDT) website (eu.idtdna.com/site/order/design-tool/index/CRISPR_SEQUENCE). SEQ ID NO 1: CTGCGGGACCATGGAATGAG. SEQ ID NOS: 30, 35, 42.

Once the most efficient and safest sgRNA was selected, which was notably the product of an experimental lapse or error, coRPK-AAV was designed. As explained in the sections below, coRPK-AAV is formed by two homologous arms (Left Homologous Arm or LHA, and Right Homologous Arm or RHA) around the SG1 On-target site, the sequence upstream of the ATG (5'UTR), coRPK cDNA, a FLAG-Tag and a bovine growth hormone polyadenylation (bgh-PolyA) signal, as it is shown in FIG. 7 and FIG. 8. The coRPK-AAV was designed taking into account the SG1 cutting site, which is at 38 bp upstream from the RPK start codon. The two homologous arms were selected from the sequence around SG1 cutting site. LHA covers the genomic region from 463 bp to 39 bp upstream from the RPK start codon (total size of 425 bp). RHA covers the region from 30 bp upstream of the RPK start codon to 395 bp downstream of the RPK start codon (total size of 425 bp). Between the genomic regions homologous with LHA and RHA, there is a region of 8 bp of the SG1 target sequence, including SG1 cutting site. This 8 bp gap between both homologous arms was considered to prevent re-cutting of SG1 once the homologous direct repair had occurred. On the other hand, the sequence covering from 37 bp upstream to the RPK start codon, part of which is Kozac sequence of RPK transcript 1 bp, corresponding to SG1 cutting site, between LHA and the 5'UTR to reduce the risk of the therapeutic cassette to be cut by SG1 once HDR had occurred.

Figure 9:
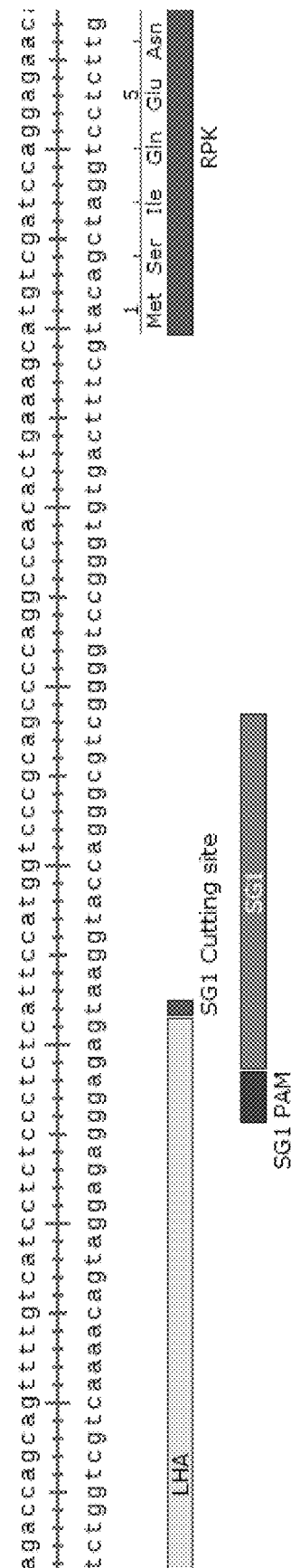
FIG. 9: Diagram showing LHA position with respect to SG1 On-target. SEQ ID NOS: 30, 35, 42.

1. LHA (Left Homologous Arm) (SEQ ID NO 13);

As shown in FIG. 9, LHA covers 425 bp upstream of the SG1 cutting site.

CAGAGTGGTGAAGGCACTCTGCATTTCTTGGTTGAGACAGAGAAAAAA

GTGGTCAGAACTGGGTAACCCTCCCCCCACCATATTATCACAGTGATCC

CTTTTGTCTTTCTTCAGGCTCCAGCCCCACCCTACAGCCCCTGCTCCCT

GGATTCACTAGAGCTAACTTCAGTAAAGTACAAAGAAAATGGGGCCATA

TGACTGGCCAAAAAAAAAATATCTATTCACGTGGATGACCAGATAGTAT

GAATGGATTGAAAATTTATCAGGAAAAAAGGATGAGAGGAAATGCCAGG

AGATGAGGGCAGAGAGCAGGCCGTTCTGGGGGAGGGATTCTGTGGGGAC

AGGGTGGCCTACTGGGTGTGCCCCTTTTCTCTTCTCTGTCTCCCTTAGA

TAAGACCAGCAGTTTTGTCATCCTCTCCCTCTC

Figure 10:
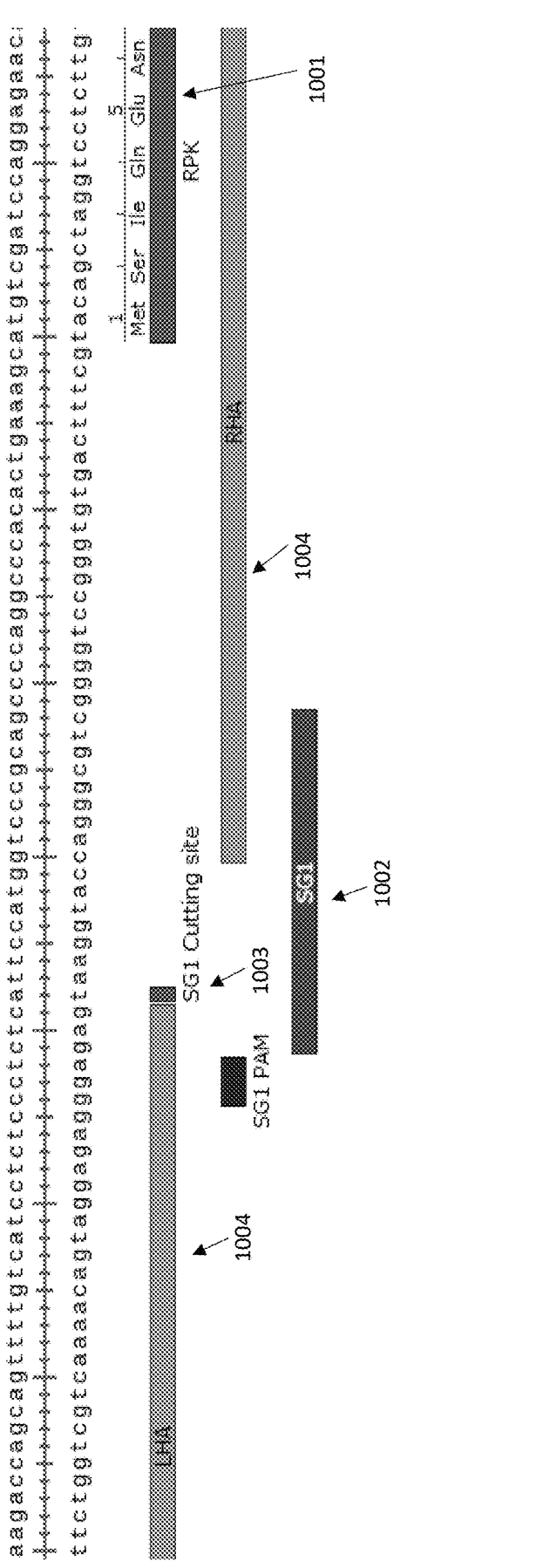
FIG. 10: Diagram showing LHA and RHA position with respect to SG1 On-target and RPK start codon. Diagram representing the sequence around the transcription start site of RPK transcript variant (CDS, 1001), showing the SG1 recognition site (1002), the cut site produced by that SG1 (1003) and the start of the homology regions of the right and left homology arms (1004), respectively. The target sequence of SG1 is divided between LHA and RHA to avoid recutting after gene editing. SEQ ID NOS: 30, 35, 42.
Figure 11:
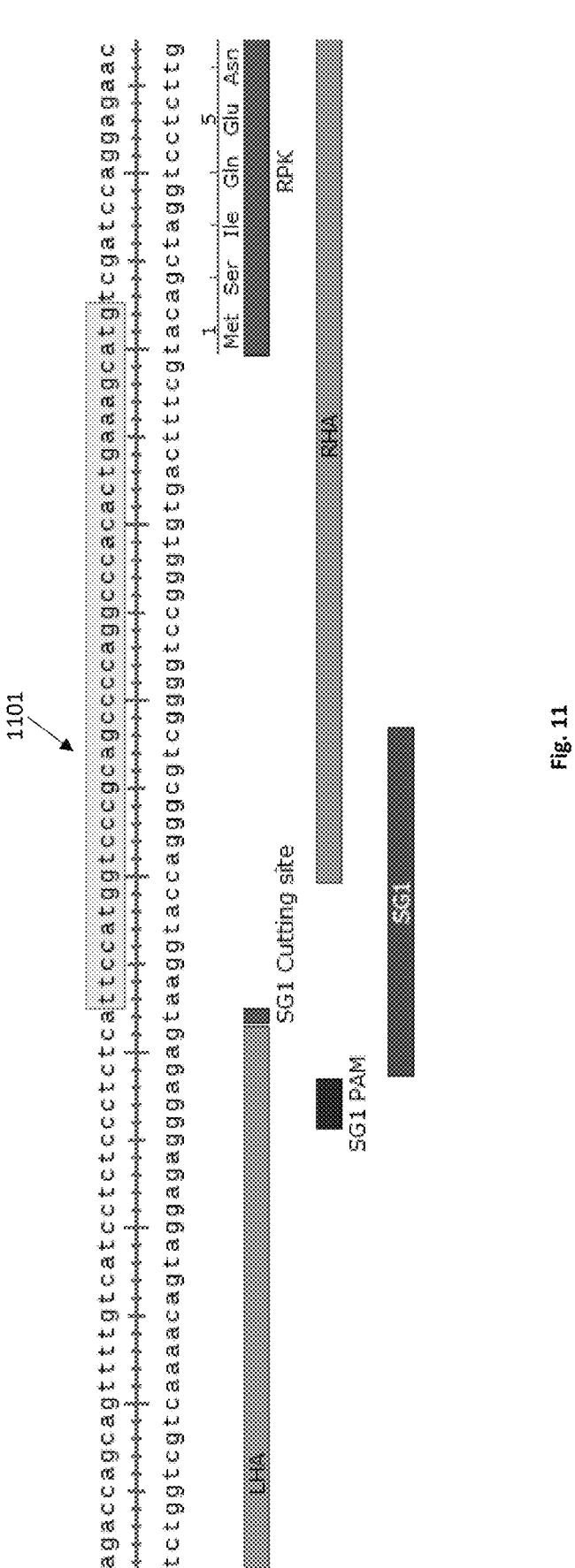
FIG. 11: Diagram showing 5'UTR position with respect to both homologous arms in PKLR locus. The indicated part of the 5'UTR region will be upstream of the DSB produced by SG1, consequently, the endogenous 5'UTR will be split after inserting of the therapeutic cassette. 1101, 5'UTR. SEQ ID NOS: 30, 35, 42.

2. RHA (Right Homology Arm) (SEQ ID NO 14):

As shown in FIG. 10, RHA covers 425 bp starting 11 bp far from SG1 PAM sequence.

GTCCCGCAGCCCCAGGCCCACACTGAAAGCATGTCGATCCAGGAGAACA

TATCATCCCTGCAGCTTCGGTCATGGGTCTCTAAGTCCCAAAGAGACTT

AGCAAAGTCCATCCTGATTGGGGCTCCAGGAGGTAAGAAGGGGAGACAG

AAGCCATGGAACATAGGAGGAAAATGAGGGTGAAAACTAGGAGCCAGGG

TGGAGGGCATAAATGATCCACATCAGCCACTGGCTAGGTGGGTTTTGGA

GAGGAACGTACGTTCTTCAGAGCCTCCCGTGTGTTAAATTATGGACCCT

GGCCTGGGTCTTTTCCAGGCCCTATAGGCAGGCCAGAGCCACAGCATGT

AAGCCACGGGGCACTCCCGTGGTTCCTGGACTCTGGCCCCTGGCATACA

GGGCTTCCAATGGAACAGGAGACAGTGGTGACA 3. 5'UTR Sequence (SEQ ID NO 15):

40 bp sequence containing from 4th nt of SG1 protospacer to RPK start codon was cloned downstream coRPK cDNA without start and STOP codons. This sequence provides apart from the start codon, the most suitable 5' UTR for a similar erythroid expression of coRPK to WT RPK, since Kozac sequence of RPK transcript variant is part of this sequence.

To note: There is a 1 bp gap between LHA and 5'UTR to prevent re-cutting by SG1 after gene editing correction, since SG1 protospacer is not completely rebuilt after gene editing.

```
TTCCATGGTCCCGCAGCCCCAGGCCCACACTGAAAGCATG
```

4. coRPK cDNA (SEQ ID NO 16):

coRPK cDNA sequence was a modified version from LV coRPK (Garcia-Gomez et al. Mol Ther. 2016), which was obtained after codon-optimization by GeneArt. Here we included the following changes, i) i) it was cloned WITH-OUT its start codon in order to use the PKLR endogenous one, with the aiming the expression of coRPK to be driven by the endogenous PKLR promoter and endogenous regulatory sequences; ii) it was cloned WITHOUT its STOP codon in order to fuse it with FLAG-Tag.

```
AGCATCCAGGAAAATATCAGCTCTCTGCAGCTGCGGTCCTGGGTGTCCA

AGAGCCAGAGAGACCTGGCCAAGAGCATCCTGATCGGAGCCCCTGGCGG

ACCAGCCGGATACCTGAGAAGGGCTAGCGTGGCCCAGCTGACCCAGGAA

CTGGGCACCGCCTTTTTCCAGCAGCAGCAGCTGCCAGCCGCCATGGCCG

ACACCTTTCTGGAACACCTGTGCCTGCTGGACATCGACTCTGAGCCCGT

GGCCGCCAGAAGCACCAGCATCATTGCCACCATCGGCCCTGCCAGCAGA

AGCGTGGAGCGGCTGAAAGAGATGATCAAGGCCGGCATGAATATCGCCC

GGCTGAACTTCTCCCACGGCAGCCACGAGTACCACGCAGAGAGCATTGC

CAACGTCCGGGAGGCCGTGGAGAGCTTTGCCGGCAGCCCCCTGAGCTAC

AGACCCGTGGCCATTGCCCTGGACACCAAGGGCCCCGAGATCAGAACAG

GAATTCTGCAGGGAGGGCCTGAGAGCGAGGTGGAGCTGGTGAAGGGCAG

CCAAGTGCTGGTGACCGTGGACCCCGCCTTCAGAACCAGAGGCAACGCC

AACACAGTGTGGGTGGACTACCCCAACATCGTGCGGGTGGTGCCTGTGG

GCGGCAGAATCTACATCGACGACGGCCTGATCAGCCTGGTGGTGCAGAA

GATCGGACCTGAGGGCCTGGTGACCCAGGTCGAGAATGGCGGCGTGCTG

GGCAGCAGAAAGGGCGTGAATCTGCCAGGCGCCCAGGTGGACCTGCCTG

GCCTGTCTGAGCAGGACGTGAGAGACCTGAGATTTGGCGTGGAGCACGG

CGTGGACATCGTGTTCGCCAGCTTCGTGCGGAAGGCCTCTGATGTGGCC

GCCGTGAGAGCCGCTCTGGGCCCTGAAGGCCACGGCATCAAGATCATCA

GCAAGATCGAGAACCACGAGGGCGTGAAGCGGTTCGACGAGATCCTGGA

AGTGTCCGACGGCATCATGGTGGCCAGAGGCGACCTGGGCATCGAGATC

CCCGCCGAGAAGGTGTTCCTGGCCCAGAAAATGATGATCGGACGGTGCA

ACCTGGCCGGCAAACCTGTGGTGTGCGCCACCCAGATGCTGGAAAGCAT

GATCACCAAGCCCAGACCCACCAGAGCCGAGACAAGCGACGTGGCCAAC

GCCGTGCTGGATGGCGCTGACTGCATCATGCTGTCCGGCGAGACAGCCA

AGGGCAACTTCCCCGTGGAGGCCGTGAAGATGCAGCACGCCATTGCCAG

AGAAGCCGAGGCCGCCGTGTACCACCGGCAGCTGTTCGAGGAACTGCGG

AGAGCCGCCCCTCTGAGCAGAGATCCCACCGAAGTGACCGCCATCGGAG

CCGTGGAAGCCGCCTTCAAGTGCTGCGCCGCTGCAATCATCGTGCTGAC
```

```
-continued
CACCACAGGCAGAAGCGCCCAGCTGCTGTCCAGATACAGACCCAGAGCC

GCCGTGATCGCCGTGACAAGATCCGCCCAGGCCGCTAGACAGGTCCACC

TGTGCAGAGGCGTGTTCCCCCTGCTGTACCGGGAGCCTCCCGAGGCCAT

CTGGGCCGACGACGTGGACAGACGGGTGCAGTTCGGCATCGAGAGCGGC

AAGCTGCGGGGCTTCCTGAGAGTGGGCGACCTGGTGATCGTGGTGACAG

GCTGGCGGCCTGGCAGCGGCTACACCAACATCATGAGGGTGCTGTCCAT

CAGC
```

5. FLAG-Tag (SEQ ID NO 17);

This sequence has been added in-frame with coRPK without STOP codon to produce a fusion protein in order to track therapeutic RPK protein after gene editing during the set-up of gene editing conditions with hCD34+ cells derived from healthy donors, but FLAG-Taq is not present in the proposed coRPK-AAV for its clinical use, since it does not have any functional contribution to correct PKD.

```
GACTACAAAGACGATGACGATAAATGA
```

6. bGH Poly(A) Signal (SEQ ID NO 18);

The bovine growth hormone polyadenylation (bGH-PolyA) signal is a specialized termination sequence for protein expression in eukaryotic cells.

```
CTGTGCCTTCTAGTTGCCAGCCATCTGTTGTTTGCCCCTCCCCCGTGCC

TTCCTTGACCCTGGAAGGTGCCACTCCCACTGTCCTTTCCTAATAAAAT

GAGGAAATTGCATCGCATTGTCTGAGTAGGTGTCATTCTATTCTGGGGG

GTGGGGGGGGCAGGACAGCAAGGGGGAGGATTGGGAAGACAATAGCAGG

CATGCTGGGGATGCGGTGGGCTCTATGG
```

7. LHA-5'UTR-coRPK-FLAG-bGH Poly(A)-RHA (SEQ ID NO 19)

This is the donor sequence designed to correct PKD through HDR at SG1 target site during set-up experiments. It comprises LHA (SEQ ID NO 13; bold), 5'UTR (SEQ ID NO 15, italic), coRPK without start and STOP codons (SEQ ID NO 16, underlined), FLAG-Taq (SEQ ID NO 17, bold and italic) and bGH poly(A) (SEQ ID NO 18, bold and underlined) RHA (SEQ ID NO 14, bold and italic), in the mentioned order. The function of these elements is described hereunder:

Homologous arms mediate in the insertion of coRPK cassette at SG1 target site

5'UTR ensures the proper regulation of the coRPK expression coRPK is a codon optimized version of RPK transcript, which codes for RPK protein to correct PKD phenotype in erythroid cells FLAG-Taq has been added to distinguish WT RPK protein from RPK coded by coRPK during the set-up of gene editing conditions with hCD34+ cells derived from healthy donors, but FLAG-Taq is not present in the proposed coRPK-AAV for its clinical use, since it does not have any functional contribution to PKD correction Finally, bGH poly(A) signal facilitates the translation of coRPK-FLAG into a protein

CAGAGTGGTGAAGGCACTCTGCATTTCTTGGTTGAGACAGAGAAAAAAAGTGGTCAGAACTGGGTAACCCTCCCCC

CACCATATTATCACAGTGATCCCTTTTGTCTTTCTTCAGGCTCCAGCCCCACCCTACAGCCCCTGCTCCCTGGATTCACT

AGAGCTAACTTCAGTAAAGTACAAAGAAAATGGGGCCATATGACTGGCCAAAAAAAAAATATCTATTCACGTGGA

TGACCAGATAGTATGAATGGATTGAAAATTTATCAGGAAAAAAGGATGAGAGGAAATGCCAGGAGATGAGGGCA

GAGAGCAGGCCGTTCTGGGGGAGGGATTCTGTGGGGACAGGGTGGCCTACTGGGTGTGCCCCTTTTCTCTTCTCTG

TCTCCCTTAGATAAGACCAGCAGTTTTGTCATCCTCTCCCTCTC*TTCCATGGTCCCGCAGCCCCAGGCCCACACTGAAA*

*GC*<u>ATGAGCATCCAGGAAAATATCAGCTCTCTGCAGCTGCGGTCCTGGGTGTCCAAGAGCCAGAGAGACCTGGCCAAG</u>

<u>AGCATCCTGATCGGAGCCCCTGGCGGACCAGCCGGATACCTGAGAAGGGCTAGCGTGGCCCAGCTGACCCAGGAAC</u>

<u>TGGGCACCGCCTTTTTCCAGCAGCAGCAGCTGCCAGCCGCCATGGCCGACACCTTTCTGGAACACCTGTGCCTGCTGG</u>

<u>ACATCGACTCTGAGCCCGTGGCCGCCAGAAGCACCAGCATCATTGCCACCATCGGCCCTGCCAGCAGAAGCGTGGAG</u>

<u>CGGCTGAAAGAGATGATCAAGGCCGGCATGAAATATCGCCCGGCTGAACTTCTTCCCACGGCCACGAGTACCACGC</u>

<u>AGAGAGCATTGCCAACGTCCGGGAGGCCGTGGAGAGCTTTGCCGGCAGCCCCCTGAGCTACAGACCCGTGGCCATTG</u>

<u>CCCTGGACACCAAGGGCCCCGAGATCAGAACAGGAATTCTGCAGGGAGGGCCTGAGAGCGAGGTGGAGCTGGTGA</u>

<u>AGGGCAGCCAAGTGCTGGTGACCGTGGACCCCGCCTTCAGAACCAGAGGCAACGCCAACACAGTGTGGGTGGACTA</u>

<u>CCCCAACATCGTGCGGGTGGTGCCTGTGGGCGGCAGAATCTACATCGACGACGGCCTGATCAGCCTGGTGGTGCAGA</u>

<u>AGATCGGACCTGAGGGCCTGGTGACCCAGGTCGAGAATGGCGGCGTGCTGGGCAGCAGAAAGGGCGTGAATCTGCC</u>

<u>AGGCGCCCAGGTGGACCTGCCTGGCCTGTCTGAGCAGGACGTGAGAGACCTGAGATTTGGCGTGGAGCACGGCGTG</u>

<u>GACATCGTGTTCGCCAGCTTCGTGCGGAAGGCCTCTGATGTGGCCGCCGTGAGAGCCGCTCTGGGCCCTGAAGGCCA</u>

<u>CGGCATCAAGATCATCAGCAAGATCGAGAACCACGAGGGCGTGAAGCGGTTCGACGAGATCCTGGAAGTGTCCGAC</u>

<u>GGCATCATGGTGGCCAGAGGCGACCTGGGCATCGAGATCCCCGCCGAGAAGGTGTTCCTGGCCCAGAAAATGATGA</u>

<u>TCGGACGGTGCAACCTGGCCGGCAAACCTGTGGTGTGCGCCACCCAGATGCTGGAAAGCATGATCACCAAGCCCAGA</u>

<u>CCCACCAGAGCCGAGACAAGCGACGTGGCCAACGCCGTGCTGGATGGCGCTGACTGCATCATGCTGTCCGGCGAGAC</u>

<u>AGCCAAGGGCAACTTCCCCGTGGAGGCCGTGAAGATGCAGCACGCCATTGCCAGAGAAGCCGAGGCCGCCGTGTAC</u>

<u>CACCGGCAGCTGTTCGAGGAACTGCGGAGAGCCGCCCCTCTGAGCAGAGATCCCACCGAAGTGACCGCCATCGGAGC</u>

<u>CGTGGAAGCCGCCTTCAAGTGCTGCGCCGCTGCAATCATCGTGCTGACCACCACAGGCAGAAGCGCCCAGCTGCTGT</u>

<u>CCAGATACAGACCCAGAGCCGCCGTGATCGCCGTGACAAGATCCGCCCAGGCCGCTAGACAGGTCCACCTGTGCAGA</u>

<u>GGCGTGTTCCCCCTGTACCGGGAGCCTCCCGAGGCCATCTGGGCCGACGACGTGGACAGACGGGTGCAGTTCGG</u>

<u>CATCGAGAGCGGCAAGCTGCGGGGCTTCCTGAGAGTGGGCGACCTGGTGATCGTGGTGACAGGCTGGCGGCCTGGC</u>

<u>AGCGGCTACACCAACATCATGAGGGTGCTGTCCATCAGC</u>*GACTACAAAGACGATGACGATAAATGA*ACGCGTGAGT

TACAAATAAAGCA<u>CTGTGCCTTCTAGTTGCCAGCCATCTGTTGTTTGCCCCTCCCCCGTGCCTTCCTTGACCCTGGAAG</u>

<u>GTGCCACTCCCACTGTCCTTTCCTAATAAAATGAGGAAATTGCATCGCATTGTCTGAGTAGGTGTCATTCTATTCTGG</u>

<u>GGGGTGGGGGGGCAGGACAGCAAGGGGGAGGATTGGGAAGACAATAGCAGGCATGCTGGGGATGCGGTGG</u>

<u>GCTCTATGGGT</u>*CCCGCAGCCCCAGGCCCACACTGAAAGCATGTCGATCCAGGAGAACATATCATCCCTGCAGCTTCG*

*GTCATGGGTCTCTAAGTCCCAAAGAGACTTAGCAAAGTCCATCCTGATTGGGGCTCCAGGAGGTAAGAAGGGGAG*

*ACAGAAGCCATGGAACATAGGAGGAAAATGAGGGTGAAAACTAGGAGCCAGGGTGGAGGGCATAAATGATCCAC*

*ATCAGCCACTGGCTAGGTGGGTTTTGGAGAGGAACGTACGTTCTTCAGAGCCTCCCGTGTGTTAAATTATGGACCCT*

*GGCCTGGGTCTTTTCCAGGCCCTATAGGCAGGCCAGAGCCACAGCATGTAAGCCACGGGGCACTCCCGTGGTTCCTG*

*GACTCTGGCCCCTGGCATACAGGGCTTCCAATGGAACAGGAGACAGTGGTGACA*

8. LHA-5'UTR-coRPK-bGH Poly(A)-RHA (SEQ ID NO 20)

SEQ ID NO 20 is the donor matrix (SEQ ID NO 19) where the FLAG-Tag sequences have been removed.

CAGAGTGGTGAAGGCACTCTGCATTTCTTGGTTGAGACAGAGAAAAAAAGTGGTCAGAACTGGGTAACCCTCCCCC

CACCATATTATCACAGTGATCCCTTTTGTCTTTCTTCAGGCTCCAGCCCCACCCTACAGCCCCTGCTCCCTGGATTCACT

AGAGCTAACTTCAGTAAAGTACAAAGAAAATGGGGCCATATGACTGGCCAAAAAAAAAAATATCTATTCACGTGGA

TGACCAGATAGTATGAATGGATTGAAAATTTATCAGGAAAAAAGGATGAGAGGAAATGCCAGGAGATGAGGGCA

GAGAGCAGGCCGTTCTGGGGGAGGGATTCTGTGGGGACAGGGTGGCCTACTGGGTGTGCCCCTTTTCTCTTCTCTG

TCTCCCTTAGATAAGACCAGCAGTTTTGTCATCCTCTCCCTCT*TTCCATGGTCCCGCAGCCCCAGGCCCACACTGAAA*

*GCATG*AGCATCCAGGAAAATATCAGCTCTCTGCAGCTGCGGTCCTGGGTGTCCAAGAGCCAGAGAGACCTGGCCAAG

AGCATCCTGATCGGAGCCCCTGGCGGACCAGCCGGATACCTGAGAAGGGCTAGCGTGGCCCAGCTGACCCAGGAAC

TGGGCACCGCCTTTTTCCAGCAGCAGCAGCTGCCAGCCGCCATGGCCGACACCTTTCTGGAACACCTGTGCCTGCTGG

ACATCGACTCTGAGCCCGTGGCCGCCAGAAGCACCAGCATCATTGCCACCATCGGCCCTGCCAGCAGAAGCGTGGAG

CGGCTGAAAGAGATGATCAAGGCCGGCATGAATATCGCCCGGCTGAACTTCTCCCACGGCAGCCACGAGTACCACGC

AGAGAGCATTGCCAACGTCCGGGAGGCCGTGGAGAGCTTTGCCGGCAGCCCCCTGAGCTACAGACCCGTGGCCATTG

CCCTGGACACCAAGGGCCCCGAGATCAGAACAGGAATTCTGCAGGGAGGGCCTGAGAGCGAGGTGGAGCTGGTGA

AGGGCAGCCAAGTGCTGGTGACCGTGGACCCCGCCTTCAGAACCAGAGGCAACGCCAACACAGTGTGGGTGGACTA

CCCCAACATCGTGCGGGTGGTGCCTGTGGGGGGCAGAATCTACATCGACGACGGCCTGATCAGCCTGGTGGTGCAGA

AGATCGGACCTGAGGGCCTGGTGACCCAGGTCGAGAATGGCGGCGTGCTGGGCAGCAGAAAGGGCGTGAATCTGCC

AGGCGCCCAGGTGGACCTGCCTGGCCTGTCTGAGCAGGACGTGAGAGACCTGAGATTTGGCGTGGAGCACGGCGTG

GACATCGTGTTCGCCAGCTTCGTGCGGAAGGCCTCTGATGTGGCCGCCGTGAGAGCCGCTCTGGGCCCTGAAGGCCA

GGCATCAAGATCATCAGCAAGATCGAGAACCACGAGGGCGTGAAGCGGTTCGACGAGATCCTGGAAGTGTCCGAC

GGCATCATGGTGGCCAGAGGCGACCTGGGCATCGAGATCCCCGCCGAGAAGGTGTTCCTGGCCCAGAAAATGATGA

TCGGACGGTGCAACCTGGCCGGCAAACCTGTGGTGTGCGCCACCCAGATGCTGGAAAGCATGATCACCAAGCCCAGA

CCCACCAGAGCCGAGACAAGCGACGTGGCCAACGCCGTGCTGGATGGCGCTGACTGCATCATGCTGTCCGGCGAGAC

AGCCAAGGGCAACTTCCCCGTGGAGGCCGTGAAGATGCAGCACGCCATTGCCAGAGAAGCCGAGGCCGCCGTGTAC

CACCGGCAGCTGTTCGAGGAACTGCGGAGAGCCGCCCCTCTGAGCAGAGATCCCACCGAAGTGACCGCCATCGGAGC

CGTGGAAGCCGCCTTCAAGTGCTGCGCCGCTGCAATCATCGTGCTGACCACCACAGGCAGAAGCGCCCAGCTGCTGT

CCAGATACAGACCCAGAGCCGCCGTGATCGCCGTGACAAGATCCGCCCAGGCCGCTAGACAGGTCCACCTGTGCAGA

GGCGTGTTCCCCCTGCTGTACCGGGAGCCTCCCGAGGCCATCTGGGCCGACGACGTGGACAGACGGGTGCAGTTCGG

CATCGAGAGCGGCAAGCTGCGGGGCTTCCTGAGAGTGGGCGACCTGGTGATCGTGGTGACAGGCTGGCGGCCTGGC

AGCGGCTACACCAACATCATGAGGGTGCTGTCCATCAGC*TGA*ACGCGTGAGTTACAAATAAAGCA<u>CTGTGCCTTCTAG</u>

<u>TTGCCAGCCATCTGTTGTTTGCCCCTCCCCCGTGCCTTCCTTGACCCTGGAAGGTGCCACTCCCACTGTCCTTTCCTAAT</u>

<u>AAAATGAGGAAATTGCATCGCATTGTCTGAGTAGGTGTCATTCTATTCTGGGGGGTGGGGGGGCAGGACAGCA</u>

<u>AGGGGGAGGATTGGGAAGACAATAGCAGGCATGCTGGGGATGCGGTGGGCTCTATGGGTCCCGCAGCCCCAGGC</u>

<u>CCACACTGAAAGCATGTCGATCCAGGAGAACATATCATCCCTGCAGCTTCGGTCATGGGTCTCTAAGTCCCAAAGAG</u>

<u>ACTTAGCAAAGTCCATCCTGATTGGGGCTCCAGGAGGTAAGAAGGGGAGACAGAAGCCATGGAACATAGGAGGA</u>

<u>AAATGAGGGTGAAAACTAGGAGCCAGGGTGGAGGGCATAAATGATCCACATCAGCCACTGGCTAGGTGGGTTTTG</u>

<u>GAGAGGAACGTACGTTCTTCAGAGCCTCCCGTGTGTTAAATTATGGACCCTGGCCTGGGTCTTTTCCAGGCCCTATA</u>

<u>GGCAGGCCAGAGCCACAGCATGTAAGCCACGGGGCACTCCCGTGGTTCCTGGACTCTGGCCCCTGGCATACAGGGC</u>

<u>TTCCAATGGAACAGGAGACAGTGGTGACA</u>

9. LHA-5'UTR-coRPK-bGH Poly(A)-RHA (SEQ ID NO 21)

SEQ ID NO 21 is the reverse sequence of the described SEQ ID NO 19.

The sequence of the coRPK therapeutic donor into the AAV from 5' to 3' is: right homology arm (bold), bGH poly(A), FLAG-Tag (bold and italic), coRPK without start codon (underlined), 5'UTR (italic) and left homology arm (bold).

```
TGTCACCACTGTCTCCTGTTCCATTGGAAGCCCTGTATGCCAGGGGCCAGAGTCCAGGAACCACGGGAGTGCCCCGT

GGCTTACATGCTGTGGCTCTGGCCTGCCTATAGGGCCTGGAAAAGACCCAGGCCAGGGTCCATAATTTAACACACG

GGAGGCTCTGAAGAACGTACGTTCCTCTCCAAAACCCACCTAGCCAGTGGCTGATGTGGATCATTTATGCCCTCCAC

CCTGGCTCCTAGTTTTCACCCTCATTTTCCTCCTATGTTCCATGGCTTCTGTCTCCCCTTCTTACCTCCTGGAGCCCCAAT

CAGGATGGACTTTGCTAAGTCTCTTTGGGACTTAGAGACCCATGACCGAAGCTGCAGGGATGATATGTTCTCCTGGA

TCGACATGCTTTCAGTGTGGGCCTGGGGCTGCGGGACCCATAGAGCCCACCGCATCCCCAGCATGCCTGCTATTGTC

TTCCCAATCCTCCCCCTTGCTGTCCTGCCCCCACCCCCCAGAATAGAATGACACCTACTCAGACAATGCGATGC

AATTTCCTCATTTTATTAGGAAAGGACAGTGGGAGTGGCACCTTCCAGGGTCAAGGAAGGCACGGGGGAGGGGCA

AACAACAGATGGCTGGCAACTAGAAGGCACAGTGCTTTATTTGTAACTCACGCGTTCATTTATCGTCATCGTCTTTGT

AGTCGCTGATGGACAGCACCCTCATGATGTTGGTGTAGCCGCTGCCAGGCCGCCAGCCTGTCACCACGATCACCAGGT

CGCCCACTCTCAGGAAGCCCCGCAGCTTGCCGCTCTCGATGCCGAACTGCACCCGTCTGTCCACGTCGTCGGCCCAGA

TGGCCTCGGGGAGGCTCCCGGTACAGCAGGGGGAACACGCCTCTGCACAGGTGGACCTGTCTAGCGGCCTGGGCGGA

TCTTGTCACGGCGATCACGGCGGCTCTGGGTCTGTATCTGGACAGCAGCTGGGCGCTTCTGCCTGTGGTGGTCAGCAC

GATGATTGCAGCGGCGCAGCACTTGAAGGCGGCTTCCACGGCTCCGATGGCGGTCACTTCGGTGGGATCTCTGCTCA

GAGGGGCGGCTCTCCGCAGTTCCTCGAACAGCTGCCGGTGGTACACGGCGGCCTCGGCTTCTCTGGCAATGGCGTGC

TGCATCTTCACGGCCTCCACGGGGAAGTTGCCCTTGGCTGTCTCGCCGGACAGCATGATGCAGTCAGCGCCATCCAGC

ACGGCGTTGGCCACGTCGCTTGTCTCGGCTCTGGTGGGTCTGGGCTTGGTGATCATGCTTTCCAGCATCTGGGTGGCG

CACACCACAGGTTTGCCGGCCAGGTTGCACCGTCCGATCATCATTTTCTGGGCCAGGAACACCTTCTCGGCGGGGATC

TCGATGCCCAGGTCGCCTCTGGCCACCATGATGCCGTCGGACACTTCCAGGATCTCGTCGAACCGCTTCACGCCCTCGT

GGTTCTCGATCTTGCTGATGATCTTGATGCCGTGGCCTTCAGGGCCCAGAGCGGCTCTCACGGCGGCCACATCAGAGG

CCTTCCGCACGAAGCTGGCGAACACGATGTCCACGCCGTGCTCCACGCCAAATCTCAGGTCTCTCACGTCCTGCTCAG

ACAGGCCAGGCAGGTCCACCTGGGCGCCTGGCAGATTCACGCCCTTTCTGCTGCCCAGCACGCCGCCATTCTCGACCT

GGTCACCAGGCCCTCAGGTCCGATCTTCTGCACCACCAGGCTGATCAGGCCGTCGTCGATGTAGATTCTGCCGCCCA

CGGTCACCAGCATTGGCTGCCCTTCACCAGCTCCACCTCGCTCTCAGGCCCTCCCTGCAGAATTCCTGTTCTGATCTCG

GGGCCCTTGGTGTCCAGGGCAATGGCCACGGGTCTGTAGCTCAGGGGGCTGCCGGCAAAGCTCTCCACGGCCTCCCG

GACGTTGGCAATGCTCTCTGCGTGGTACTCGTGGCTGCCGTGGGAGAAGTTCAGCCGGGCGATATTCATGCCGGCCT

TGATCATCTCTTTCAGCCGCTCCACGCTTCTGCTGGCAGGGCCGATGGTGGCAATGATGCTGGTGCTTCTGGCGGCCA

CGGGCTCAGAGTCGATGTCCAGCAGGCACAGGTGTTCCAGAAAGGTGTCGGCCATGGCGGCTGGCAGCTGCTGCTG

CTGGAAAAAGGCGGTGCCCAGTTCCTGGGTCAGCTGGGCCACGCTAGCCCTTCTAGGTATCCGGCTGGTCCGCCAG

GGGCTCCGATCAGGATGCTCTTGGCCAGGTCTCTCTGGCTCTTGGACACCCAGGACCGCAGCTGCAGAGAGCTGATAT

TTTCCTGGATGCTCATGCTTTCAGTGTGGGCCTGGGGCTGCGGGACCATGGAAGAGAGGGAGAGGATGACAAAACTG

CTGGTCTTATCTAAGGGAGACAGAGAAGAGAAAAGGGGCACACCCAGTAGGCCACCCTGTCCCCACAGAATCCCTCC

CCCAGAACGGCCTGCTCTCTGCCCTCATCTCCTGGCATTTCCTCTCATCCTTTTTTCCTGATAAATTTTCAATCCATTCAT

ACTATCTGGTCATCCACGTGAATAGATATTTTTTTTTTGGCCAGTCATATGGCCCCATTTTCTTTGTACTTTACTGAAGTT

AGCTCTAGTGAATCCAGGGAGCAGGGGCTGTAGGGTGGGGCTGGAGCCTGAAGAAAGACAAAAGGGATCACTGTG

ATAATATGGTGGGGGGAGGGTTACCCAGTTCTGACCACTTTTTTTCTGTCTCAACCAAGAAATGCAGAGTGCCTTCA

CCACTCTG
```

10. LHA-S'UTR-CORPK-bGH Poly(A)-RHA (SEO ID NO 22)

SEQ ID NO 22 is the reverse sequence of the described SEQ ID NO 20.

The sequence of the coRPK therapeutic donor into the AAV from S' to 3' is: right homology arm (bold), bGH poly(A), coRPK without start codon (underlined), 5'UTR (italic) and left homology arm (bold).

```
TGTCACCACTGTCTCCTGTTCCATTGGAAGCCCTGTATGCCAGGGGCCAGAGTCCAGGAACCACGGGAGTGCCCCGT

GGCTTACATGCTGTGGCTCTGGCCTGCCTATAGGGCCTGGAAAAGACCCAGGCCAGGGTCCATAATTTAACACACG

GGAGGCTCTGAAGAACGTACGTTCCTCTCCAAAACCCACCTAGCCAGTGGCTGATGTGGATCATTTATGCCCTCCAC

CCTGGCTCCTAGTTTTCACCCTCATTTTCCTCCTATGTTCCATGGCTTCTGTCTCCCCTTCTTACCTCCTGGAGCCCCAAT

CAGGATGGACTTTGCTAAGTCTCTTTGGGACTTAGAGACCCATGACCGAAGCTGCAGGGATGATATGTTCTCCTGGA

TCGACATGCTTTCAGTGTGGGCCTGGGGCTGCGGGACCCATAGAGCCCACCGCATCCCCAGCATGCCTGCTATTGTC

TTCCCAATCCTCCCCCTTGCTGTCCTGCCCCACCCCACCCCCCAGAATAGAATGACACCTACTCAGACAATGCGATGC

AATTTCCTCATTTTATTAGGAAAGGACAGTGGGAGTGGCACCTTCCAGGGTCAAGGAAGGCACGGGGGAGGGGCA

AACAACAGATGGCTGGCAACTAGAAGGCACAGTGCTTTATTTGTAACTCACGCGTTCAGCTGATGGACAGCACCCTC

ATGATGTTGGTGTAGCCGCTGCCAGGCCGCCAGCCTGTCACCACGATCACCAGGTCGCCCACTCTCAGGAAGCCCCGC

AGCTTGCCGCTCTCGATGCCGAACTGCACCCGTCTGTCCACGTCGTCGGCCCAGATGGCCTCGGGAGGCTCCCGGTAC

AGCAGGGGGAACACGCCTCTGCACAGGTGGACCTGTCTAGCGGCCTGGGCGGATCTTGTCACGGCGATCACGGCGG

CTCTGGGTCTGTATCTGGACAGCAGCTGGGCGCTTCTGCCTGTGGTGGTCAGCACGATGATTGCAGCGGCGCAGCAC

TTGAAGGCGGCTTCCACGGCTCCGATGGCGGTCACTTCGGTGGGATCTCTGCTCAGAGGGGCGGCTCTCCGCAGTTC

CTCGAACAGCTGCCGGTGGTACACGGCGGCCTCGGCTTCTCTGGCAATGGCGTGCTGCATCTTCACGGCCTCCACGGG

GAAGTTGCCCTTGGCTGTCTCGCCGGACAGCATGATGCAGTCAGCGCCATCCAGCACGGCGTTGGCCACGTCGCTTGT

CTCGGCTCTGGTGGGTCTGGGCTTGGTGATCATGCTTTCCAGCATCTGGGTGGCGCACACCACAGGTTTGCCGGCCAG

GTTGCACCGTCCGATCATCATTTTCTGGGCCAGGAACACCTTCTCGGCGGGGATCTCGATGCCCAGGTCGCCTCTGGC

CACCATGATGCCGTCGGACACTTCCAGGATCTCGTCGAACCGCTTCACGCCCTCGTGGTTCTCGATCTTGCTGATGATC

TTGATGCCGTGGCCTTCAGGGCCCAGAGCGGCTCTCACGGCGGCCACATCAGAGGCCTTCCGCACGAAGCTGGCGAA

CACGATGTCCACGCCGTGCTCCACGCCAAATCTCAGGTCTCTCACGTCCTGCTCAGACAGGCCAGGCAGGTCCACCTG

GGCGCCTGGCAGATTCACGCCCTTTCTGCTGCCCAGCACGCCGCCATTCTCGACCTGGGTCACCAGGCCCTCAGGTCC

GATCTTCTGCACCACCAGGCTGATCAGGCCGTCGTCGATGTAGATTCTGCCGCCCACAGGCACCACCCGCACGATGTT

GGGGTAGTCCACCCACACTGTGTTGGCGTTGCCTCTGGTTCTGAAGGCGGGGTCCACGGTCACCAGCACTTGGCTGCC

CTTCACCAGCTCCACCTCGCTCTCAGGCCCTCCCTGCAGAATTCCTGTTCTGATCTCGGGGCCCTTGGTGTCCAGGGCA

ATGGCCACGGGTCTGTAGCTCAGGGGGCTGCCGGCAAAGCTCTCCACGGCCTCCCGGACGTTGGCAATGCTCTCTGC

GTGGTACTCGTGGCTGCCGTGGGAGAAGTTCAGCCGGGCGATATTCATGCCGGCCTTGATCATCTCTTTCAGCCGCTC

CACGCTTCTGCTGGCAGGGCCGATGGTGGCAATGATGCTGGTGCTTCTGGCGGCCACGGGCTCAGAGTCGATGTCCA

GCAGGCACAGGTGTTCCAGAAAGGTGTCGGCCATGGCGGCTGGCAGCTGCTGCTGCTGGAAAAAGGCGGTGCCCAG

TCCTGGGTCAGCTGGGCCACGCTAGCCCTTCTCAGGTATCCGGCTGGTCCGCCAGGGGCTCCGATCAGGATGCTCTT

GGCCAGGTCTCTCTGGCTCTTGGACACCCAGGACCGCAGCTGCAGAGAGCTGATATTTTCCTGGATGCTCATGCTTTC

AGTGTGGGCCTGGGGCTGCGGGACCCATGGAAGAGAGGGAGAGGATGACAAAACTGCTGGTCTTATCTAAGGGAGAC

AGAGAAGAGAAAAGGGGCACACCCAGTAGGCCACCCTGTCCCCACAGAATCCCTCCCCCAGAACGGCCTGCTCTCTG

CCCTCATCTCCTGGCATTTCCTCTCATCCTTTTTTTCCTGATAAATTTTCAATCCATTCATACTATCTGGTCATCCACGTGAA

TAGATATTTTTTTTTTGGCCAGTCATATGGCCCCATTTTCTTTGTACTTTACTGAAGTTAGCTCTAGTGAATCCAGGGAG

CAGGGGCTGTAGGGTGGGGCTGGAGCCTGAAGAAAGACAAAAGGGATCACTGTGATAATATGGTGGGGGGAGGGT

TACCCAGTTCTGACCACTTTTTTTTCTCTGTCTCAACCAAGAAATGCAGAGTGCCTTCACCACTCTG
```

11. AAV Backbone (SEQ ID NO 23):

Transfer plasmid carrying ITRs from pAAV-MCS plasmid (Aglient Technologies) containing AAV2 ITRs (Internal Terminal Repeats) was used. LHA-5'UTR-coRPK-FLAG-bGH poly(A)-RHA in reverse orientation (SEQ ID NO 20) was cloned into an AAV backbone through Noti restriction site cloning.

```
CCTGCAGGCAGCTGCGCGCTCGCTCGCTCACTGAGGCCGCCCGGGCGTCGGGCGACCTTTGGTCGCCCGGCCTCAGT

GAGCGAGCGAGCGCGCAGAGAGGGAGTGGCCAACTCCATCACTAGGGGTTCCTGCGGCCGCAGGAACCCCTAGTGA

TGGAGTTGGCCACTCCCTCTCTGCGCGCTCGCTCGCTCACTGAGGCCGGGCGACCAAAGGTCGCCCGACGCCCGGGC

TTTGCCCGGGCGGCCTCAGTGAGCGAGCGAGCGCGCAGCTGCCTGCAGGGGCGCCTGATGCGGTATTTTCTCCTTAC

GCATCTGTGCGGTATTTCACACCGCATACGTCAAAGCAACCATAGTACGCGCCCTGTAGCGGCGCATTAAGCGCGGCG

GGTGTGGTGGTTACGCGCAGCGTGACCGCTACACTTGCCAGCGCCCTAGCGCCCGCTCCTTTCGCTTTCTTCCCTTCCT

TTCTCGCCACGTTCGCCGGCTTTCCCCGTCAAGCTCTAAATCGGGGGCTCCCTTTAGGGTTCCGATTTAGTGCTTTACG

GCACCTCGACCCCAAAAAACTTGATTTGGGTGATGGTTCACGTAGTGGGCCATCGCCCTGATAGACGGTTTTTCGCCC

TTTGACGTTGGAGTCCACGTTCTTTAATAGTGGACTCTTGTTCCAAACTGGAACAACACTCAACCCTATCTCGGGCTATT

CTTTTGATTTATAAGGGATTTTGCCGATTTCGGCCTATTGGTTAAAAAATGAGCTGATTTAACAAAAATTTAACGCGAA

TTTTAACAAAATATTAACGTTTACAATTTTATGGTGCACTCTCAGTACAATCTGCTCTGATGCCGCATAGTTAAGCCAGC

CCCGACACCCGCCAACACCCGCTGACGCGCCCTGACGGGCTTGTCTGCTCCCGGCATCCGCTTACAGACAAGCTGTGA

CCGTCTCCGGGAGCTGCATGTGTCAGAGGTTTTCACCGTCATCACCGAAACGCGCGAGACGAAAGGGCCTCGTGATA

CGCCTATTTTTATAGGTTAATGTCATGATAATAATGGTTTCTTAGACGTCAGGTGGCACTTTTCGGGGAAATGTGCGCG

GAACCCCTATTTGTTTATTTTTCTAAATACATTCAAATATGTATCCGCTCATGAGACAATAACCCTGATAAATGCTTCAA

TAATATTGAAAAAGGAAGAGTATGAGTATTCAACATTTCCGTGTCGCCCTTATTCCCTTTTTTGCGGCATTTTGCCTTCC

TGTTTTTGCTCACCCAGAAACGCTGGTGAAAGTAAAAGATGCTGAAGATCAGTTGGGTGCACGAGTGGGTTACATCG

AACTGGATCTCAACAGCGGTAAGATCCTTGAGAGTTTTCGCCCCGAAGAACGTTTTCCAATGATGAGCACTTTTAAAG

TTCTGCTATGTGGCGCGGTATTATCCCGTATTGACGCCGGGCAAGAGCAACTCGGTCGCCGCATACACTATTCTCAGA

ATGACTTGGTTGAGTACTCACCAGTCACAGAAAAGCATCTTACGGATGGCATGACAGTAAGAGAATTATGCAGTGCT

GCCATAACCATGAGTGATAACACTGCGGCCAACTTACTTCTGACAACGATCGGAGGACCGAAGGAGCTAACCGCTTTT

TTGCACAACATGGGGGATCATGTAACTCGCCTTGATCGTTGGGAACCGGAGCTGAATGAAGCCATACCAAACGACGA

GCGTGACACCACGATGCCTGTAGCAATGGCAACAACGTTGCGCAAACTATTAACTGGCGAACTACTTACTCTAGCTTC

CCGGCAACAATTAATAGACTGGATGGAGGCGGATAAAGTTGCAGGACCACTTCTGCGCTCGGCCCTTCCGGCTGGCT

GGTTTATTGCTGATAAATCTGGAGCCGGTGAGCGTGGGTCTCGCGGTATCATTGCAGCACTGGGGCCAGATGGTAAG

CCCTCCCGTATCGTAGTTATCTACACGACGGGGAGTCAGGCAACTATGGATGAACGAAATAGACAGATCGCTGAGAT

AGGTGCCTCACTGATTAAGCATTGGTAACTGTCAGACCAAGTTTACTCATATATACTTTAGATTGATTTAAAACTTCATT

TTTAATTTAAAAGGATCTAGGTGAAGATCCTTTTTGATAATCTCATGACCAAAATCCCTTAACGTGAGTTTTCGTTCCAC

TGAGCGTCAGACCCCGTAGAAAAGATCAAAGGATCTTCTTGAGATCCTTTTTTTCTGCGCGTAATCTGCTGCTTGCAAA

CAAAAAAACCACCGCTACCAGCGGTGGTTTGTTTGCCGGATCAAGAGCTACCAACTCTTTTTCCGAAGGTAACTGGCT

TCAGCAGAGCGCAGATACCAAATACTGTCCTTCTAGTGTAGCCGTAGTTAGGCCACCACTTCAAGAACTCTGTAGCAC

CGCCTACATACCTCGCTCTGCTAATCCTGTTACCAGTGGCTGCTGCCAGTGGCGATAAGTCGTGTCTTACCGGGTTGGA

CTCAAGACGATAGTTACCGGATAAGGCGCAGCGGTCGGGCTGAACGGGGGGTTCGTGCACACAGCCCAGCTTGGAG
```

```
                                     -continued
CGAACGACCTACACCGAACTGAGATACCTACAGCGTGAGCTATGAGAAAGCGCCACGCTTCCCGAAGGGAGAAAGG

CGGACAGGTATCCGGTAAGCGGCAGGGTCGGAACAGGAGAGCGCACGAGGGAGCTTCCAGGGGGAAACGCCTGGT

ATCTTTATAGTCCTGTCGGGTTTCGCCACCTCTGACTTGAGCGTCGATTTTTGTGATGCTCGTCAGGGGGGCGGAGCCT

ATGGAAAAACGCCAGCAACGCGGCCTTTTTACGGTTCCTGGCCTTTTGCTGGCCTTTTGCTCACATGT
```

12. coRPK AAV Used for Pre-Clinical Studies (SEQ ID NO 24):

Sequence that comprises coRPK therapeutic donor (SEQ ID NO 19) inserted in the AAV backbone (SEQ ID NO 23).

```
CCTGCAGGCAGCTGCGCGCTCGCTCGCTCACTGAGGCCGCCCGGGCGTCGGGCGACCTTTGGTCGCCCGGCCTCAGT

GAGCGAGCGAGCGCGCAGAGAGGGAGTGGCCAACTCCATCACTAGGGGTTCCTGCGGCCGC

CAGAGTGGTGAAGGCACTCTGCATTTCTTGGTTGAGACAGAGAAAAAAAGTGGTCAGAACTGGGTAACCCTCCCCC

CACCATATTATCACAGTGATCCCTTTTGTCTTTCTTCAGGCTCCAGCCCCACCCTACAGCCCCTGCTCCCTGGATTCACT

AGAGCTAACTTCAGTAAAGTACAAAGAAAATGGGGCCATATGACTGGCCAAAAAAAAAAATATCTATTCACGTGGA

TGACCAGATAGTATGAATGGATTGAAAATTTATCAGGAAAAAAGGATGAGAGGAAATGCCAGGAGATGAGGGCA

GAGAGCAGGCCGTTCTGGGGGAGGGATTCTGTGGGGACAGGGTGGCCTACTGGGTGTGCCCCTTTTCTCTTCTCTG

TCTCCCTTAGATAAGACCAGCAGTTTTGTCATCCTCTCCCTCTC*TTCCATGGTCCCGCAGCCCCAGGCCCACACTGAAA*

*GCATG*AGCATCCAGGAAAATATCAGCTCTCTGCAGCTGCGGTCCTGGGTGTCCAAGAGCCAGAGAGACCTGGCCAAG

AGCATCCTGATCGGAGCCCCTGGCGGACCAGCCGGATACCTGAGAAGGGCTAGCGTGGCCCAGCTGACCCAGGAAG

TGGGCACCGCCTTTTTCCAGCAGCAGCAGCTGCCAGCCGCCATGGCCGACACCTTTCTGGAACACCTGTGCCTGCTGG

ACATCGACTCTGAGCCCGTGGCCGCCAGAAGCACCAGCATCATTGCCACCATCGGCCCTGCCAGCAGAAGCGTGGAG

CGGCTGAAAGAGATGATCAAGGCCGGCATGAATATCGCCCGGCTGAACTTCTCCCACGGCAGCCACGAGTACCACGG

AGAGAGCATTGCCAACGTCCGGGAGGCCGTGGAGAGCTTTGCCGGCAGCCCCCTGAGCTACAGACCCGTGGCCATTG

CCCTGGACACCAAGGGCCCCGAGATCAGAACAGGAATTCTGCAGGGAGGGCCTGAGAGCGAGGTGGAGCTGGTGA

AGGGCAGCCAAGTGCTGGTGACCGTGGACCCCGCCTTCAGAACCAGAGGCAACGCCAACACAGTGTGGGTGGACTA

CCCCAACATCGTGCGGGTGGTGCCTGTGGGCGGCAGAATCTACATCGACGACGGCCTGATCAGCCTGGTGGTGCAGA

AGATCGGACCTGAGGGCCTGGTGACCCAGGTCGAGAATGGCGGCGTGCTGGGCAGCAGAAAGGGCGTGAATCTGCC

AGGCGCCCAGGTGGACCTGCCTGGCCTGTCTGAGCAGGACGTGAGAGACCTGAGATTTGGCGTGGAGCACGGCGTG

GACATCGTGTTCGCCAGCTTCGTGCGGAAGGCCTCTGATGTGGCCGCCGTGAGAGCCGCTCTGGGCCCTGAAGCCA

CGGCATCAAGATCATCAGCAAGATCGAGAACCACGAGGGCGTGAAGCGGTTCGACGAGATCCTGGAAGTGTCCGAC

GGCATCATGGTGGCCAGAGGCGACCTGGGCATCGAGATCCCCGCCGAGAAGGTGTTCCTGGCCCAGAAAATGATGA

TCGGACGGTGCAACCTGGCCGGCAAACCTGTGGTGTGCGCCACCCAGATGCTGGAAAGCATGATCACCAAGCCCAGA

CCCACCAGAGCCGAGACAAGCGACGTGGCCAACGCCGTGCTGGATGGCGCTGACTGCATCATGCTGTCCGGCGAGAC

AGCCAAGGGCAACTTCCCCGTGGAGGCCGTGAAGATGCAGCACGCCATTGCCAGAGAAGCCGAGGCCGCCGTGTAC

CACCGGCAGCTGTTCGAGGAACTGCGGAGAGCCGCCCCTCTGAGCAGAGATCCCACCGAAGTGACCGCCATCGGAGC

CGTGGAAGCCGCCTTAAGTGCTGCGCCGTGCAATCATCGTGCTGACCACCACAGGCAGAAGCGCCCAGCTCTGT

CCAGATACAGACCCAGAGCCGCCGTGATCGCCGTGACAAGATCCGCCCAGGCCGCTAGACAGGTCCACCTGTGCAGA

GGCGTGTTCCCCCTGCTGTACCGGGAGCCTCCCGAGGCCATCTGGGCCGACGACGTGGACAGACGGGTGCAGTTCGG

CATCGAGAGCGGCAAGCTGCGGGCTTCCTGAGAGTGGGCGACCTGGTGATCGTGGTGACAGGCTGGCGGCCTGGC

AGCGGCTACACCAACATCATGAGGGTGCTGTCCATCAGC*GACTACAAAGACGATGACGATAAATGA*ACGCGTGAGT

TACAAATAAAGCACTGTGCCTTCTAGTTGCCAGCCATCTGTTGTTTGCCCCTCCCCCGTGCCTTCCTTGACCCTGGAAG

GTGCCACTCCCACTGTCCTTTCCTAATAAAATGAGGAAATTGCATCGCATTGTCTGAGTAGGTGTCATTCTATTCTGG
```

-continued

GGGGTGGGGTGGGGCAGGACAGCAAGGGGGAGGATTGGGAAGACAATAGCAGGCATGCTGGGGATGCGGTGG

GCTCTATGGGTCCCGCAGCCCCAGGCCCACACTGAAAGCATGTCGATCCAGGAGAACATATCATCCCTGCAGCTTCG

GTCATGGGTCTCTAAGTCCCAAAGAGACTTAGCAAAGTCCATCCTGATTGGGGCTCCAGGAGGTAAGAAGGGGAG

ACAGAAGCCATGGAACATAGGAGGAAAATGAGGGTGAAAACTAGGAGCCAGGGTGGAGGGCATAAATGATCCAC

ATCAGCCACTGGCTAGGTGGGTTTTGGAGAGGAACGTACGTTCTTCAGAGCCTCCCGTGTGTTAAATTATGGACCCT

GGCCTGGGTCTTTTCCAGGCCCTATAGGCAGGCCAGAGCCACAGCATGTAAGCCACGGGGCACTCCCGTGGTTCCT

GGACTCTGGCCCCTGGCATACAGGGCTTCCAATGGAACAGGAGACAGTGGTGACAGCGGCCGCAGGAACCCCTAGT

GATGGAGTTGGCCACTCCCTCTCTGCGCGCTCGCTCGCTCACTGAGGCCGGGCGACCAAAGGTCGCCCGACGCCCGG

GCTTTGCCCGGGCGGCCTCAGTGAGCGAGCGAGCGCGCAGCTGCCTGCAGGGGCGCCTGATGCGGTATTTTCTCCTT

ACGCATCTGTGCGGTATTTCACACCGCATACGTCAAAGCAACCATAGTACGCGCCCTGTAGCGGCGCATTAAGCGCGG

CGGGTGTGGTGGTTACGCGCAGCGTGACCGCTACACTTGCCAGCGCCCTAGCGCCCGCTCCTTTCGCTTTCTTCCCTTC

CTTTCTCGCCACGTTCGCCGGCTTTCCCCGTCAAGCTCTAAATCGGGGGCTCCCTTTAGGGTTCCGATTTAGTGCTTTAC

GGCACCTCGACCCCAAAAAACTTGATTTGGGTGATGGTTCACGTAGTGGGCCATCGCCCTGATAGACGGTTTTTCGCC

CTTTGACGTTGGAGTCCACGTTCTTTAATAGTGGACTCTTGTTCCAAACTGGAACAACACTCAACCCTATCTCGGGCTA

TTCTTTTGATTTATAAGGGATTTTGCCGATTTCGGCCTATTGGTTAAAAAATGAGCTGATTTAACAAAAATTTAACGCG

AATTTTAACAAAATATTAACGTTTACAATTTTATGGTGCACTCTCAGTACAATCTGCTCTGATGCCGCATAGTTAAGCCA

GCCCCGACACCCGCCAACACCCGCTGACGCGCCCTGACGGGCTTGTCTGCTCCCGGCATCCGCTTACAGACAAGCTGT

GACCGTCTCCGGGAGCTGCATGTGTCAGAGGTTTTCACCGTCATCACCGAAACGCGCGAGACGAAAGGGCCTCGTGA

TACGCCTATTTTTATAGGTTAATGTCATGATAATAATGGTTTCTTAGACAAACCTAGATATTGATAGTCTGATCGGTCAA

CGTATAATCGAGTCCTAGCTTTTGCAAACATCTATCAAGAGACAGGATCAGCAGGAGGCTTTCGCATGATTGAACAAG

ATGGATTGCACGCAGGTTCTCCGGCGGCTTGGGTGGAGAGGCTATTCGGCTATGACTGGGCACAACAGACAATCGGC

TGCTCTGATGCCGCCGTGTTCCGGCTGTCAGCGCAGGGGCGTCCGGTTCTTTTTGTCAAGACCGACCTGTCCGGTGCC

CTGAATGAACTGCAAGACGAGGCAGCGCGGCTATCGTGGCTGGCGACGACGGGCGTTCCTTGCGCGGCTGTGCTCG

ACGTTGTCACTGAAGCGGGAAGGGACTGGCTGCTATTGGGCGAAGTGCCGGGGCAGGATCTCCTGTCATCTCACCTT

GCTCCTGCCGAGAAAGTATCCATCATGGCTGATGCAATGCGGCGGCTGCATACGCTTGATCCGGCTACCTGCCCATTC

GACCACCAAGCGAAACATCGCATCGAGCGAGCACGTACTCGGATGGAAGCCGGTCTTGTCGATCAGGATGATCTGGA

CGAAGAGCATCAGGGGCTCGCGCCAGCCGAACTGTTCGCCAGGCTCAAGGCGTCTATGCCCGACGGCGAGGATCTCG

TCGTGACCCACGGCGATGCCTGCTTGCCGAATATCATGGTGGAAAATGGCCGCTTTTCTGGATTCATCGACTGTGGCC

GTCTGGGTGTGGCGGACCGCTATCAGGACATAGCGTTGGCTACCCGTGATATTGCTGAAGAGCTTGGCGGCGAATGG

GCTGACCGCTTCCTTGTGCTTTACGGTATCGCCGCGCCCGATTCGCAGCGCATCGCCTTCTATCGCCTTCTTGACGAGT

TCTTCTGACCGATTCTAGGTGCATTGGCGCAGAAAAAAATGCCTGATGCGACGCTGCGCGTCTTATACTCCCACATATG

CCAGATTCAGCAACGGATACGGCTTCCCCAACTTGCCCACTTCCATACGTGTCCTCCTTACCAGAAATTTATCCTTAACG

ATCGGACGGGGAGTCAGGCAACTATGGATGAACGAAATAGACAGATCGCTGAGATAGGTGCCTCACTGATTAAGCAT

TGGTAACTGTCAGACCAAGTTTACTCATATATACTTTAGATTGATTTAAAACTTCATTTTTAATTTAAAAGGATCTAGGT

GAAGATCCTTTTTGATAATCTCATGACCAAAATCCCTTAACGTGAGTTTTCGTTCCACTGAGCGTCAGACCCCGTAGAA

AAGATCAAAGGATCTTCTTGAGATCCTTTTTTTCTGCGCGTAATCTGCTGCTTGCAAACAAAAAAACCACCGCTACCAG

CGGTGGTTTGTTTGCCGGATCAAGAGCTACCAACTCTTTTTCCGAAGGTAACTGGCTTCAGCAGAGCGCAGATACCAA

ATACTGTTCTTCTAGTGTAGCCGTAGTTAGGCCACCACTTCAAGAACTCTGTAGCACCGCCTACATACCTCGCTCTGCTA

ATCCTGTTACCAGTGGCTGCTGCCAGTGGCGATAAGTCGTGTCTTACCGGGTTGGACTCAAGACGATAGTTACCGGAT

AAGGCGCAGCGGTCGGGCTGAACGGGGGGTTCGTGCACACAGCCCAGCTTGGAGCGAACGACCTACACCGAACTGA

-continued

GATACCTACAGCGTGAGCTATGAGAAAGCGCCACGCTTCCCGAAGGGAGAAAGGCGGACAGGTATCCGGTAAGCGG

CAGGGTCGGAACAGGAGAGCGCACGAGGGGAGCTTCCAGGGGGAAACGCCTGGTATCTTTATAGTCCTGTCGGGTTTC

GCCACCTCTGACTTGAGCGTCGATTTTTGTGATGCTCGTCAGGGGGGCGGAGCCTATGGAAAAACGCCAGCAACGCG

GCCTTTTTACGGTTCCTGGCCTTTTGCTGGCCTTTTGCTCACATGT 13. coRPK AAV Used for Pre-Clinical Studies (SEQ ID NO 25): 10

Sequence that comprises coRPK therapeutic donor (SEQ ID NO 20) inserted in the AAV backbone (SEQ ID NO 23).

CCTGCAGGCAGCTGCGCGCTCGCTCGCTCACTGAGGCCGCCCGGGCGTCGGGCGACCTTTGGTCGCCCGGCCTCAGT

GAGCGAGCGAGCGCGCAGAGAGGGAGTGGCCAACTCCATCACTAGGGGTTCCTGCGGCCGC

CAGAGTGGTGAAGGCACTCTGCATTTCTTGGTTGAGACAGAGAAAAAAAGTGGTCAGAACTGGGTAACCCTCCCCC

CACCATATTATCACAGTGATCCCTTTTGTCTTTCTTCAGGCTCCAGCCCCACCCTACAGCCCCTGCTCCCTGGATTCACT

AGAGCTAACTTCAGTAAAGTACAAAGAAAATGGGGCCATATGACTGGCCAAAAAAAAAATATCTATTCACGTGGA

TGACCAGATAGTATGAATGGATTGAAAATTTATCAGGAAAAAAAGGATGAGAGGAAATGCCAGGAGATGAGGGCA

GAGAGCAGGCCGTTCTGGGGGAGGGATTCTGTGGGGACAGGGTGGCCTACTGGGTGTGCCCCTTTTCTCTTCTCTG

TCTCCCTTAGATAAGACCAGCAGTTTTGTCATCCTCTCCCTCTC_TTCCATGGTCCCGCAGCCCCAGGCCCACACTGAAA_

_GCATG_<u>AGCATCCAGGAAAATATCAGCTCTCTGCAGCTGCGGTCCTGGGTGTCCAAGAGCCAGAGAGACCTGGCCAAG</u>

<u>AGCATCCTGATCGGAGCCCCTGGCGGACCAGCCGGATACCTGAGAAGGCTAGCGTGGCCCAGCTGACCCAGGAAC</u>

<u>ACATCGACTCTGAGCCCGTGGCCGCCAGAAGCACCAGCATCATTGCCACCATCGGCCCTGCCAGCAGAAGCGTGGAG</u>

<u>CGGCTGAAAGAGATGATCAAGGCCGGCATGAATATCGCCCGGCTGAACTTCTCCCACGGCAGCCACGAGTACCACG</u>

<u>AGAGAGCATTGCCAACGTCCGGGAGGCCGTGGAGAGCTTTGCCGGCAGCCCCCTGAGCTACAGACCCGTGGCCATTG</u>

<u>CCCTGGACACCAAGGGCCCCGAGATCAGAACAGGAATTCTGCAGGGAGGGCCTGAGAGCGAGGTGGAGCTGGTGA</u>

<u>AGGCAGCCAAGTGCTGGTGACCGTGGACCCCGCCTTCAGAACCAGAGGCAACGCCAACACAGTGTGGGTGGACTA</u>

<u>CCCCAACATCGTGCGGGTGGTGCCTGTGGGCGGCAGAATCTACATCGACGACGGCCTGATCAGCCTGGTGGTGCAGA</u>

<u>AGATCGGACCTGAGGGCCTGGTGACCCAGGTCGAGAATGGCGGCGTGCTGGGCAGCAGAAAGGGCGTGAATCTGCC</u>

<u>AGGCGCCCAGGTGGACCTGCCTGGCCTGTCTGAGCAGGACGTGAGAGACCTGAGATTTGGCGTGGAGCACGGCGTG</u>

<u>GACATCGTGTTCGCCAGCTTCGTGCGGAAGGCCTCTGATGTGGCCGCCGTGAGAGCCGCTCTGGGCCCTGAAGGCCA</u>

<u>CGGCATCAAGATCATCAGCAAGATCGAGAACCACGAGGGCGTGAAGCGGTTCGACGAGATCCTGGAAGTGTCCGAC</u>

<u>GCATCATGGTGGCCAGAGGCGACCTGGGCATCGAGATCCCCGCCGAGAAGGTGTTCCTGGCCCAGAAAATGATGA</u>

<u>TCGGACGGTGCAACCTGGCCGGCAAACCTGTGGTGTGCGCCACCCAGATGCTGGAAAGCATGATCACCAAGCCCAGA</u>

<u>CCCACCAGAGCCGAGACAAGCGACGTGGCCAACGCCGTGCTGGATGGCGCTGACTGCATCATGCTGTCCGGCGAGAC</u>

<u>AGCCAAGGGCAACTTCCCCGTGGAGGCCGTGAAGATGCAGCACGCCATTGCCAGAGAAGCCGAGGCCGCCGTGTAC</u>

<u>CACCGGCAGCTGTTCGAGGAACTGCGCGAGAGCCGCCCCTCTGAGCAGAGATCCCACCGAAGTGACCGCCATCGGAGC</u>

<u>CGTGGAAGCCGCCTTCAAGTGCTGCGCCGCTGCAATCATCGTGCTACCACCACAGGCAGAAGCGCCCAGCTGCTGT</u>

<u>CCAGATACAGACCCAGAGCCGCCGTGATCGCCGTGACAAGATCCGCCCAGGCCGCTAGACAGGTCCACCTGTGCAGA</u>

<u>GGCGTGTTCCCCCTGCTGTACCGGGAGCCTCCCGAGGCCATCTGGGCCGACGACGTGGACAGACGGGTGCAGTTCGG</u>

<u>CATCGAGCGGCAAGCTGCGGGGCTTCCTGAGAGTGGGCGACCTGGTGATCGTGGTGACAGGCTGGCGGCCTGGC</u>

<u>AGCGGCTACACCAACATCATGAGGGTGCTGTCCATCAGC_TGA_ACGCGTGAGTTACAAATAAAGCA</u>CTGTGCCTTCTAG

TTGCCAGCCATCTGTTGTTTGCCCCTCCCCCGTGCCTTCCTTGACCCTGGAAGGTGCCACTCCCACTGTCCTTTCCTAAT

AAAATGAGGAAATTGCATCGCATTGTCTGAGTAGGTGTCATTCTATTCTGGGGGGTGGGGGGGGCAGGACAGCA

AGGGGGAGGATTGGGAAGACAATAGCAGGCATGCTGGGGATGCGGTGGGCTCTATGGGTCCCGCAGCCCCAGGC

-continued

CCACACTGAAAGCATGTCGATCCAGGAGAACATATCATCCCTGCAGCTTCGGTCATGGGTCTCTAAGTCCCAAAGAG

ACTTAGCAAAGTCCATCCTGATTGGGGCTCCAGGAGGTAAGAAGGGGAGACAGAAGCCATGGAACATAGGAGGA

AAATGAGGGTGAAAACTAGGAGCCAGGGTGGAGGGCATAAATGATCCACATCAGCCACTGGCTAGGTGGGTTTTG

GAGAGGAACGTACGTTCTTCAGAGCCTCCCGTGTGTTAAATTATGGACCCTGGCCTGGGTCTTTTCCAGGCCCTATA

GGCAGGCCAGAGCCACAGCATGTAAGCCACGGGGCACTCCCGTGGTTCCTGGACTCTGGCCCCTGGCATACAGGGC

TTCCAATGGAACAGGAGACAGTGGTGACAGCGGCCGCAGGAACCCCTAGTGATGGAGTTGGCCACTCCCTCTCTGC

GCGCTCGCTCGCTCACTGAGGCCGGGCGACCAAAGGTCGCCCGACGCCCGGGCTTTGCCCGGGCGGCCTCAGTGAGC

GAGCGAGCGCGCAGCTGCCTGCAGGGGCGCCTGATGCGGTATTTTCTCCTTACGCATCTGTGCGGTATTTCACACCGC

ATACGTCAAAGCAACCATAGTACGCGCCCTGTAGCGGCGCATTAAGCGCGGCGGGTGTGGTGGTTACGCGCAGCGTG

ACCGCTACACTTGCCAGCGCCCTAGCGCCCGCTCCTTTCGCTTTCTTCCCTTCCTTTCTCGCCACGTTCGCCGGCTTTCCC

CGTCAAGCTCTAAATCGGGGGCTCCCTTTAGGGTTCCGATTTAGTGCTTTACGGCACCTCGACCCCAAAAAACTTGATT

TGGGTGATGGTTCACGTAGTGGGCCATCGCCCTGATAGACGGTTTTTCGCCCTTTGACGTTGGAGTCCACGTTCTTTAA

TAGTGGACTCTTGTTCCAAACTGGAACAACACTCAACCCTATCTCGGGCTATTCTTTTGATTTATAAGGGATTTTGCCGA

TTTCGGCCTATTGGTTAAAAAATGAGCTGATTTAACAAAAATTTAACGCGAATTTTAACAAAATATTAACGTTTACAATT

TTATGGTGCACTCTCAGTACAATCTGCTCTGATGCCGCATAGTTAAGCCAGCCCCGACACCCGCCAACACCCGCTGACG

CGCCCTGACGGGCTTGTCTGCTCCCGGCATCCGCTTACAGACAAGCTGTGACCGTCTCCGGGAGCTGCATGTGTCAGA

GGTTTTCACCGTCATCACCGAAACGCGCGAGACGAAAGGGCCTCGTGATACGCCTATTTTTATAGGTTAATGTCATGA

TAATAATGGTTTCTTAGACAAACCTAGATATTGATAGTCTGATCGGTCAACGTATAATCGAGTCCTAGCTTTTGCAAAC

ATCTATCAAGAGACAGGATCAGCAGGAGGCTTTCGCATGATTGAACAAGATGGATTGCACGCAGGTTCTCCGGCGGC

TTGGGTGGAGAGGCTATTCGGCTATGACTGGGCACAACAGACAATCGGCTGCTCTGATGCCGCCGTGTTCCGGCTGT

CAGCGCAGGGGCGTCCGGTTCTTTTTGTCAAGACCGACCTGTCCGGTGCCCTGAATGAACTGCAAGACGAGGCAGCG

CGGCTATCGTGGCTGGCGACGACGGGCGTTCCTTGCGCGGCTGTGCTCGACGTTGTCACTGAAGCGGGAAGGGACTG

GCTGCTATTGGGCGAAGTGCCGGGGCAGGATCTCCTGTCATCTCACCTTGCTCCTGCCGAGAAAGTATCCATCATGGC

TGATGCAATGCGGCGGCTGCATACGCTTGATCCGGCTACCTGCCCATTCGACCACCAAGCGAAACATCGCATCGAGCG

AGCACGTACTCGGATGGAAGCCGGTCTTGTCGATCAGGATGATCTGGACGAAGAGCATCAGGGGCTCGCGCCAGCC

GAACTGTTCGCCAGGCTCAAGGCGTCTATGCCCGACGGCGAGGATCTCGTCGTGACCCACGGCGATGCCTGCTTGCC

GAATATCATGGTGGAAAATGGCCGCTTTTCTGGATTCATCGACTGTGGCCGTCTGGGTGTGGCGGACCGCTATCAGG

ACATAGCGTTGGCTACCCGTGATATTGCTGAAGAGCTTGGCGGCGAATGGGCTGACCGCTTCCTTGTGCTTTACGGTA

TCGCCGCGCCCGATTCGCAGCGCATCGCCTTCTATCGCCTTCTTGACGAGTTCTTCTGACCGATTCTAGGTGCATTGGC

GCAGAAAAAAATGCCTGATGCGACGCTGCGCGTCTTATACTCCCACATATGCCAGATTCAGCAACGGATACGGCTTCC

CCAACTTGCCCACTTCCATACGTGTCCTCCTTACCAGAAATTTATCCTTAACGATCGGACGGGGAGTCAGGCAACTATG

GATGAACGAAATAGACAGATCGCTGAGATAGGTGCCTCACTGATTAAGCATTGGTAACTGTCAGACCAAGTTTACTCA

TATATACTTTAGATTGATTTAAAACTTCATTTTTAATTTAAAAGGATCTAGGTGAAGATCCTTTTTGATAATCTCATGAC

CAAAATCCCTTAACGTGAGTTTTCGTTCCACTGAGCGTCAGACCCCGTAGAAAAGATCAAAGGATCTTCTTGAGATCCT

TTTTTTCTGCGCGTAATCTGCTGCTTGCAAACAAAAAAACCACCGCTACCAGCGGTGGTTTGTTTGCCGGATCAAGAGC

TACCAACTCTTTTTCCGAAGGTAACTGGCTTCAGCAGAGCGCAGATACCAAATACTGTTCTTCTAGTGTAGCCGTAGTT

AGGCCACCACTTCAAGAACTCTGTAGCACCGCCTACATACCTCGCTCTGCTAATCCTGTTACCAGTGGCTGCTGCCAGT

GGCGATAAGTCGTGTCTTACCGGGTTGGACTCAAGACGATAGTTACCGGATAAGGCGCAGCGGTCGGGCTGAACGG

GGGGTTCGTGCACACAGCCCAGCTTGGAGCGAACGACCTACACCGAACTGAGATACCTACAGCGTGAGCTATGAGAA

AGCGCCACGCTTCCCGAAGGGAGAAAGGCGGACAGGTATCCGGTAAGCGGCAGGGTCGGAACAGGAGAGCGCACG

-continued

```
AGGGAGCTTCCAGGGGGAAACGCCTGGTATCTTTATAGTCCTGTCGGGTTTCGCCACCTCTGACTTGAGCGTCGATTT

TTGTGATGCTCGTCAGGGGGGCGGAGCCTATGGAAAAACGCCAGCAACGCGGCCTTTTTACGGTTCCTGGCCTTTTGC

TGGCCTTTTGCTCACATGT
```

14. coRPK AAV Used for Pre-Clinical Studies (SEQ ID NO 26):

Sequence that comprises coRPK therapeutic donor (SEQ ID NO 21) inserted in the AAV backbone (SEQ ID NO 23).

```
CCTGCAGGCAGCTGCGCGCTCGCTCGCTCACTGAGGCCGCCCGGGCGTCGGGCGACCTTTGGTCGCCCGGCCTCAGT

GAGCGAGCGAGCGCGCAGAGAGGGAGTGGCCAACTCCATCACTAGGGGTTCCTGCGGCCGCTGTCACCACTGTCTCC

TGTTCCATTGGAAGCCCTGTATGCCAGGGGCCAGAGTCCAGGAACCACGGGAGTGCCCCGTGGCTTACATGCTGTG

GCTCTGGCCTGCCTATAGGGCCTGGAAAAGACCCAGGCCAGGGTCCATAATTTAACACACGGGAGGCTCTGAAGAA

CGTACGTTCCTCTCCAAAACCCACCTAGCCAGTGGCTGATGTGGATCATTTATGCCCTCCACCCTGGCTCCTAGTTTTC

ACCCTCATTTTCCTCCTATGTTCCATGGCTTCTGTCTCCCCTTCTTACCTCCTGGAGCCCCAATCAGGATGGACTTTGCT

AAGTCTCTTTGGGACTTAGAGACCCATGACCGAAGCTGCAGGGATGATATGTTCTCCTGGATCGACATGCTTTCAGT

GTGGGCCTGGGGCTGCGGGACCCATAGAGCCCACCGCATCCCCAGCATGCCTGCTATTGTCTTCCCAATCCTCCCCCT

TGCTGTCCTGCCCCACCCCACCCCCCAGAATAGAATGACACCTACTCAGACAATGCGATGCAATTTCCTCATTTTATT

AGGAAAGGACAGTGGGAGTGGCACCTTCCAGGGTCAAGGAAGGCACGGGGGAGGGGCAAACAACAGATGGCTG

GCAACTAGAAGGCACAGTGCTTTATTTGTAACTCACGCGT*TCATTTATCGTCATCGTCTTTGTAGTC*GCTGATGGACA

GCACCCTCATGATGTTGGTGTAGCCGCTGCCAGGCCGCCAGCCTGTCACCACGATCACCAGGTCGCCCACTCTCAGGA

AGCCCCGCAGCTTGCCGCTCTCGATGCCGAACTGCACCCGTCTGTCCACGTCGTCGGCCCAGATGGCCTCGGGAGGCT

CCCGGTACAGCAGGGGGAACACGCCTCTGCACAGGTGGACCTGTCTAGCGGCCTGGGCGGATCTTGTCACGGCGATC

ACGGCGGCTCTGGGTCTGTATCTGGACAGCAGCTGGGCGCTTCTGCCTGTGGTGGTCAGCACGATGATTGCAGCGGC

GCAGCACTTGAAGGCGGCTTCCACGGCTCCGATGGCGGTCACTTCGGTGGGATCTCTGCTCAGAGGGGCGGCTCTCC

GCAGTTCCTCGAACAGCTGCCGGTGGTACACGGCGGCCTCGGCTTCTCTGGCAATGGCGTGCTGCATCTTCACGGCCT

CCACGGGGAAGTTGCCCTTGGCTGTCTCGCCGGACAGCATGATGCAGTCAGCGCCATCCAGCACGGCGTTGGCCACG

TCGCTTGTCTCGGCTCTGGTGGGTCTGGGCTTGGTGATCATGCTTTCCAGCATCTGGGTGGCGCACACCACAGGT]TTG

CCGGCCAGGTTGCACCGTCCGATCATCATTTTCTGGGCCAGGAACACCTTCTCGGGGGGATCTCGATGCCCAGGTCG

CCTCTGGCCACCATGAT]GCCGTCGGACACTTCCAGGATCTCGTCGAACCGCTTCACGCCCTCGTGGTTCTCGATCTTGC

TGATGATCTTGATGCCGTGGCCTTCAGGGCCCAGAGCGGCTCTCACGGCGGCCACATCAGAGGCCTTCCGCACGAAG

CTGGCGAACACGATGTCCACGCCGTGCTCCACGCCAAATCTCAGGTCTCTCACGTCCTGCTCAGACAGGCCAGGCAGG

TCCACCTGGGCGCCTGGCAGATTCACGCCCTTTCTGCTGCCCAGCACGCCGCCATTCTCGACCTGGGTCACCAGGCCCT

CAGGTCCGATCTTCTGCACCACCAGGCTGATCAGGCCGTCGTCGATGTAGATTCTGCCGCCCACAGGCACCACCCGCA

CGATGTTGGGGTAGTCCACCCACACTGTGTTGGCGTTGCCTCTGGTTCTGAAGGCGGGGTCCACGGTCACCAGCACTT

GGCTGCCCTTCACCAGCTCCACCTCGCTCTCAGGCCCTCCCTGCAGAATTCCTGTTCTGATCTCGGGGCCCTTGGTGTC

CAGGGCAATGGCCACGGGTCTGTAGCTCAGGGGGCTGCCGGCAAAGCTCTCCACGGCCTCCCGGACGTTGGCAATGC

TCTGCGTGGTACTCGTGGCTGCCGTGGGAAGTTCAGCCGGGCGATATTCATGCCGGCCTTGATCATCTCTTTCA

GCCGCTCCACGCTTCTGCTGGCAGGGCCGATGGTGGCAATGATGCTGGTGCTTCTGGCGGCCACGGGCTCAGAGTCG

ATGTCCAGCAGGCACAGGTGTTCCAGAAAGGGTGTCGGCCATGGCGGCTGGCAGCTGCTGCTGCTGGAAAAAGGCGG

TGCCCAGTTCCTGGGTCAGCTGGGCCACGCTAGCCCTTCTCAGGTATCCGGCTGGTCCGCCAGGGGCTCCGATCAGGA

TGCCCAGTTCCTGGGTCAGCTGGGCCACGCTAGCCCTTCTCAGGTATCCGGCTGGTCCGCCAGGGGCTCCGATCAGGA

TGCTCTTGGCCAGGTCTCTCTGGCTCTTGGACACCCAGGACCGCAGCTGCAGAGAGCTGATATTTTCCTGGATGCTCAT
```

-continued

*GCTTTCAGTGTGGGCCTGGGGCTGCGGGACC*ATGGAAGAGAGGGAGAGGATGACAAAACTGCTGGTCTTATCTAAG

GGAGACAGAGAAGAGAAAAGGGGCACACCCAGTAGGCCACCCTGTCCCCACAGAATCCCTCCCCCAGAACGGCCTGC

TCTCTGCCCTCATCTCCTGGCATTTCCTCTCATCCTTTTTTCCTGATAAATTTTCAATCCATTCATACTATCTGGTCATCCA

CGTGAATAGATATTTTTTTTTTGGCCAGTCATATGGCCCCATTTTCTTTGTACTTTACTGAAGTTAGCTCTAGTGAATCC

AGGGAGCAGGGGCTGTAGGGTGGGGCTGGAGCCTGAAGAAAGACAAAAGGGATCACTGTGATAATATGGTGGGGG

GAGGGTTACCCAGTTCTGACCACTTTTTTTCTCTGTCTCAACCAAGAAATGCAGAGTGCCTTCACCACTCTGGCGGCCG

CAGGAACCCCTAGTGATGGAGTTGGCCACTCCCTCTCTGCGCGCTCGCTCGCTCACTGAGGCCGGGCGACCAAAGGTC

GCCCGACGCCCGGGCTTTGCCCGGGCGGCCTCAGTGAGCGAGCGAGCGCGCAGCTGCCTGCAGGGGCGCCTGATGC

GGTATTTTCTCCTTACGCATCTGTGCGGTATTTCACACCGCATACGTCAAAGCAACCATAGTACGCGCCCTGTAGCGGC

GCATTAAGCGCGGCGGGTGTGGTGGTTACGCGCAGCGTGACCGCTACACTTGCCAGCGCCCTAGCGCCCGCTCCTTTC

GCTTTCTTCCCTTCCTTTCTCGCCACGTTCGCCGGCTTTCCCCGTCAAGCTCTAAATCGGGGGCTCCCTTTAGGGTTCCG

ATTTAGTGCTTTACGGCACCTCGACCCCAAAAAACTTGATTTGGGTGATGGTTCACGTAGTGGGCCATCGCCCTGATA

GACGGTTTTTCGCCCTTTGACGTTGGAGTCCACGTTCTTTAATAGTGGACTCTTGTTCCAAACTGGAACAACACTCAAC

CCTATCTCGGGCTATTCTTTTGATTTATAAGGGATTTTGCCGATTTCGGCCTATTGGTTAAAAAATGAGCTGATTTAACA

AAAATTTAACGCGAATTTTAACAAAATATTAACGTTTACAATTTTATGGTGCACTCTCAGTACAATCTGCTCTGATGCCG

CATAGTTAAGCCAGCCCCGACACCCGCCAACACCCGCTGACGCGCCCTGACGGGCTTGTCTGCTCCCGGCATCCGCTT

ACAGACAAGCTGTGACCGTCTCCGGGAGCTGCATGTGTCAGAGGTTTTCACCGTCATCACCGAAACGCGCGAGACGA

AAGGGCCTCGTGATACGCCTATTTTTATAGGTTAATGTCATGATAATAATGGTTTCTTAGACAAACCTAGATATTGATA

GTCTGATCGGTCAACGTATAATCGAGTCCTAGCTTTTGCAAACATCTATCAAGAGACAGGATCAGCAGGAGGCTTTCG

CATGATTGAACAAGATGGATTGCACGCAGGTTCTCCGGCCGGCTTGGGTGGAGAGGCTATTCGGCTATGACTGGGCAC

AACAGACAATCGGCTGCTCTGATGCCGCCGTGTTCCGGCTGTCAGCGCAGGGGCGTCCGGTTCTTTTTGTCAAGACCG

ACCTGTCCGGTGCCCTGAATGAACTGCAAGACGAGGCAGCGCGGCTATCGTGGCTGGCGACGACGGGCGTTCCTTGC

GCGGCTGTGCTCGACGTTGTCACTGAAGCGGGAAGGGACTGGCTGCTATTGGGCGAAGTGCCGGGGCAGGATCTCC

TGTCATCTCACCTTGCTCCTGCCGAGAAAGTATCCATCATGGCTGATGCAATGCGGCGGCTGCATACGCTTGATCCGG

CTACCTGCCCATTCGACCACCAAGCGAAACATCGCATCGAGCGAGCACGTACTCGGATGGAAGCCGGTCTTGTCGATC

AGGATGATCTGGACGAAGAGCATCAGGGGCTCGCGCCAGCCGAACTGTTCGCCAGGCTCAAGGCGTCTATGCCCGAC

GGCGAGGATCTCGTCGTGACCCACGGCGATGCCTGCTTGCCGAATATCATGGTGGAAAATGGCCGCTTTTCTGGATTC

ATCGACTGTGGCCGTCTGGGTGTGGCGGACCGCTATCAGGACATAGCGTTGGCTACCCGTGATATTGCTGAAGAGCT

TGGCGGCGAATGGGCTGACCGCTTCCTTGTGCTTTACGGTATCGCCGCGCCCGATTCGCAGCGCATCGCCTTCTATCG

CCTTCTTGACGAGTTCTTCTGACCGATTCTAGGTGCATTGGCGCAGAAAAAAATGCCTGATGCGACGCTGCGCGTCTT

ATACTCCCACATATGCCAGATTCAGCAACGGATACGGCTTCCCCAACTTGCCCACTTCCATACGTGTCCTCCTTACCAGA

AATTTATCCTTAACGATCGGACGGGGAGTCAGGCAACTATGGATGAACGAAATAGACAGATCGCTGAGATAGGTGCC

TCACTGATTAAGCATTGGTAACTGTCAGACCAAGTTTACTCATATATACTTTAGATTGATTTAAAACTTCATTTTTAATTT

AAAAGGATCTAGGTGAAGATCCTTTTTGATAATCTCATGACCAAAATCCCTTAACGTGAGTTTTCGTTCCACTGAGCGT

CAGACCCCGTAGAAAAGATCAAAGGATCTTCTTGAGATCCTTTTTTTTCTGCGCGTAATCTGCTGCTTGCAAACAAAAAA

ACCACCGCTACCAGCGGTGGTTTGTTTGCCGGATCAAGAGCTACCAACTCTTTTTCCGAAGGTAACTGGCTTCAGCAG

AGCGCAGATACCAAATACTGTTCTTCTAGTGTAGCCGTAGTTAGGCCACCACTTCAAGAACTCTGTAGCACCGCCTACA

TACCTCGCTCTGCTAATCCTGTTACCAGTGGCTGCTGCCAGTGGCGATAAGTCGTGTCTTACCGGGTTGGACTCAAGAC

GATAGTTACCGGATAAGGCGCAGCGGTCGGGCTGAACGGGGGGTTCGTGCACACAGCCCAGCTTGGAGCGAACGAC

CTACACCGAACTGAGATACCTACAGCGTGAGCTATGAGAAAGCGCCACGCTTCCCGAAGGGAGAAAGGCGGACAGG

-continued

TATCCGGTAAGCGGCAGGGTCGGAACAGGAGAGCGCACGAGGGAGCTTCCAGGGGGAAACGCCTGGTATCTTTATA

GTCCTGTCGGGTTTCGCCACCTCTGACTTGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTTGCTCACATGT 15. coRPK AAV for Clinical Use (SEQ ID NO 27):
    Sequence that comprises coRPK therapeutic donor (SEQ
ID NO 22) inserted in the AAV backbone (SEQ ID NO 23).

CCTGCAGGCAGCTGCGCGCTCGCTCGCTCACTGAGGCCGCCCGGGCGTCGGGCGACCTTTGGTCGCCCGGCCTCAGT

GAGCGAGCGAGCGCGCAGAGAGGGAGTGGCCAACTCCATCACTAGGGGTTCCTGCGGCCGCTGTCACCACTGTCTCC

TGTTCCATTGGAAGCCCTGTATGCCAGGGGCCAGAGTCCAGGAACCACGGGAGTGCCCCGTGGCTTACATGCTGTG

GCTCTGGCCTGCCTATAGGGCCTGGAAAAGACCCAGGCCAGGGTCCATAATTTAACACACGGGAGGCTCTGAAGAA

CGTACGTTCCTCTCCAAAACCCACCTAGCCAGTGGCTGATGTGGATCATTTATGCCCTCCACCCTGGCTCCTAGTTTTC

ACCCTCATTTTCCTCCTATGTTCCATGGCTTCTGTCTCCCCTTCTTACCTCCTGGAGCCCCAATCAGGATGGACTTTGCT

AAGTCTCTTTGGGACTTAGAGACCCATGACCGAAGCTGCAGGGATGATATGTTCTCCTGGATCGACATGCTTTCAGT

GTGGGCCTGGGGCTGCGGGACCCATAGAGCCCACCGCATCCCCAGCATGCCTGCTATTGTCTTCCCAATCCTCCCCCT

TGCTGTCCTGCCCCACCCCACCCCCCAGAATAGAATGACACCTACTCAGACAATGCGATGCAATTTCCTCATTTTATT

AGGAAAGGACAGTGGGAGTGGCACCTTCCAGGGTCAAGGAAGGCACGGGGGAGGGGCAAACAACAGATGGCTG

GCAACTAGAAGGCACAGTGCTTTATTTGTAACTCACGCGT*TCA*GCTGATGGACAGCACCCTCATGATGTTGGTGTAGC

CGCTGCCAGGCCGCCAGCCTGTCACCACGATCACCAGGTCGCCCACTCTCAGGAAGCCCCGCAGCTTGCCGCTCTCGA

TGCCGAACTGCACCCGTCTGTCCACGTCGTCGGCCCAGATGGCCTCGGGAGGCTCCCGGTACAGCAGGGGGAACACG

CCTCTGCACAGGTGGACCTGTCTAGCGGCCTGGGCGGATCTTGTCACGGCGATCACGGCGGCTCTGGGTCTGTATCTG

GACAGCAGCTGGGCGCTTCTGCCTGTGGTGGTCAGCACGATGATTGCAGCGGCGCAGCACTTGAAGGCGGCTTCCAC

GGCTCCGATGGCGGTCACTTCGGTGGGATCTCTGCTCAGAGGGGCGGCTCTCCGCAGTTCCTCGAACAGCTGCCGGT

GGTACACGGCGGCCTCGGCTTCTCTGGCAATGGCGTGCTGCATCTTCACGGCCTCCACGGGGAAGTTGCCCTTGGCTG

TCTCGCCGGACAGCATGATGCAGTCAGCGCCATCCAGCACGGCGTTGGCCACGTCGCTTGTCTCGGCTCGGTGGGTC

TGGGCTTGGTGATCATGCTTTCCAGCATCTGGGTGGCGCACACCACAGGTTTGCCGGCCAGGTTGCACCGTCCGATCA

TCATTTTCTGGGCCAGGAACACCTTCTCGGCGGGGATCTCGATGCCCAGGTCGCCTCTGGCCACCATGATGCCGTCGG

ACACTTCCAGGATCTCGTCGAACCGCTTCACGCCCTCGTGGTTCTCGATCTTGCTGATGATCTTGATGCCGTGGCCTTC

AGGGCCCAGAGCGGCTCTCACGGCGGCCACATCAGAGGCCTTCCGCACGAAGCTGGCGAACACGATGTCCACGCCGT

GCTCCACGCCAAATCTCAGGTCTCTCACGTCCTGCTCAGACAGGCCAGGCAGGTCCACCTGGGCGCCTGGCAGATTCA

CGCCCTTTCTGCTGCCCAGCACGCCGCCATTCTCGACCTGGGTCACCAGGCCCTCAGGTCCGATCTTCTGCACCACCAG

GCTGATCAGGCCGTCGTCGATGTAGATTCTGCCGCCCACAGGCACCACCCGCACGATGTTGGGGTAGTCCACCCACAC

TGTGTTGGCGTTGCCTCTGGTTCTGAAGGCGGGGTCCACGGTCACCAGCACTTGGCTGCCCTTCACCAGCTCCACCTC

GCTCTCAGGCCCTCCCTGCAGAATTCCTGTTCTGATCTCGGGGCCCTTGGTGTCCAGGGCAATGGCCACGGGTCTGTA

GCTCAGGGGGCTGCCGGCAAAGCTCTCCACGGCCTCCCGGACGTTGGCAATGCTCTCTGCGTGGTACTCGTGGCTGCC

GTGGGAGAAGTTCAGCCGGGCGATATTCATGCCGGCCTTGATCATCTCTTTCAGCCGCTCCACGCTTCTGCTGGCAGG

GCCGATGGTGGCAATGATGCTGGTGCTTCTGGCGGCCACGGGCTCAGAGTCGATGTCCAGCAGGCACAGGTGTTCCA

CACGCTAGCCCTTCTCAGGTATCCGGCTGGTCCGCCAGGGGCTCCGATCAGGATGCTCTTGGCCAGGTCTCTCTGGCT

CTTGGACACCCAGGACCGCAGCTGCAGAGAGCTGATATTTTCCTGGATGCT*CATGCTTTCAGTGTGGGCCTGGGGCTG*

*CGGGACCATGGAAGAGAGGGAGAGGATGACAAAACTGCTGGTCTTATCTAAGGGAGACAGAGAAGAGAAAAGGGG*

CACACCCAGTAGGCCACCCTGTCCCCACAGAATCCCTCCCCCAGAACGGCCTGCTCTCTGCCCTCATCTCCTGGCAT

-continued

```
CTCTCATCCTTTTTTCCTGATAAATTTTCAATCCATTCATACTATCTGGTCATCCACGTGAATAGATATTTTTTTTTTGGCC

AGTCATATGGCCCCATTTTCTTTGTACTTTACTGAAGTTAGCTCTAGTGAATCCAGGGAGCAGGGGCTGTAGGGTGGG

GCTGGAGCCTGAAGAAAGACAAAAGGGATCACTGTGATAATATGGTGGGGGGAGGGTTACCCAGTTCTGACCACTTT

TTTTCTCTGTCTCAACCAAGAAATGCAGAGTGCCTTCACCACTCTGGCGGCCGCAGGAACCCCTAGTGATGGAGTTGG

CCACTCCCTCTCTGCGCGCTCGCTCGCTCACTGAGGCCGGGCGACCAAAGGTCGCCCGACGCCCGGGCTTTGCCCGGG

CGGCCTCAGTGAGCGAGCGAGCGCGCAGCTGCCTGCAGGGGCGCCTGATGCGGTATTTTCTCCTTACGCATCTGTGC

GGTATTTCACACCGCATACGTCAAAGCAACCATAGTACGCGCCCTGTAGCGGCGCATTAAGCGCGGCGGGTGTGGTG

GTTACGCGCAGCGTGACCGCTACACTTGCCAGCGCCCTAGCGCCCGCTCCTTTCGCTTTCTTCCCTTCCTTTCTCGCCAC

GTTCGCCGGCTTTCCCCGTCAAGCTCTAAATCGGGGGCTCCCTTTAGGGTTCCGATTTAGTGCTTTACGGCACCTCGAC

CCCAAAAAACTTGATTTGGGTGATGGTTCACGTAGTGGGCCATCGCCCTGATAGACGGTTTTTCGCCCTTTGACGTTG

GAGTCCACGTTCTTTAATAGTGGACTCTTGTTCCAAACTGGAACAACACTCAACCCTATCTCGGGCTATTCTTTTGATTT

ATAAGGGATTTTGCCGATTTCGGCCTATTGGTTAAAAAATGAGCTGATTTAACAAAAATTTAACGCGAATTTTAACAAA

ATATTAACGTTTACAATTTTATGGTGCACTCTCAGTACAATCTGCTCTGATGCCGCATAGTTAAGCCAGCCCCGACACC

CGCCAACACCCGCTGACGCGCCCTGACGGGCTTGTCTGCTCCCGGCATCCGCTTACAGACAAGCTGTGACCGTCTCCG

GGAGCTGCATGTGTCAGAGGTTTTCACCGTCATCACCGAAACGCGCGAGACGAAAGGGCCTCGTGATACGCCTATTTT

TATAGGTTAATGTCATGATAATAATGGTTTCTTAGACAAACCTAGATATTGATAGTCTGATCGGTCAACGTATAATCGA

GTCCTAGCTTTTGCAAACATCTATCAAGAGACAGGATCAGCAGGAGGCTTTCGCATGATTGAACAAGATGGATTGCAC

GCAGGTTCTCCGGCGGCTTGGGTGGAGAGGCTATTCGGCTATGACTGGGCACAACAGACAATCGGCTGCTCTGATGC

CGCCGTGTTCCGGCTGTCAGCGCAGGGGCGTCCGGTTCTTTTTGTCAAGACCGACCTGTCCGGTGCCCTGAATGAACT

GCAAGACGAGGCAGCGCGGCTATCGTGGCTGGCGACGACGGGCGTTCCTTGCGCGGCTGTGCTCGACGTTGTCACTG

AAGCGGGAAGGGACTGGCTGCTATTGGGCGAAGTGCCGGGGCAGGATCTCCTGTCATCTCACCTTGCTCCTGCCGAG

AAAGTATCCATCATGGCTGATGCAATGCGGCGGCTGCATACGCTTGATCCGGCTACCTGCCCATTCGACCACCAAGCG

AAACATCGCATCGAGCGAGCACGTACTCGGATGGAAGCCGGTCTTGTCGATCAGGATGATCTGGACGAAGAGCATCA

GGGGCTCGCGCCAGCCGAACTGTTCGCCAGGCTCAAGGCGTCTATGCCCGACGGCGAGGATCTCGTCGTGACCCACG

GCGATGCCTGCTTGCCGAATATCATGGTGGAAAATGGCCGCTTTTCTGGATTCATCGACTGTGGCCGTCTGGGTGTGG

CGGACCGCTATCAGGACATAGCGTTGGCTACCCGTGATATTGCTGAAGAGCTTGGCGGCGAATGGGCTGACCGCTTC

CTTGTGCTTTACGGTATCGCCGCGCCCGATTCGCAGCGCATCGCCTTCTATCGCCTTCTTGACGAGTTCTTCTGACCGAT

TCTAGGTGCATTGGCGCAGAAAAAAATGCCTGATGCGACGCTGCGCGTCTTATACTCCCACATATGCCAGATTCAGCA

ACGGATACGGCTTCCCCAACTTGCCCACTTCCATACGTGTCCTCCTTACCAGAAATTTATCCTTAACGATCGGACGGGG

AGTCAGGCAACTATGGATGAACGAAATAGACAGATCGCTGAGATAGGTGCCTCACTGATTAAGCATTGGTAACTGTC

AGACCAAGTTTACTCATATATACTTTAGATTGATTTAAAACTTCATTTTTAATTTAAAAGGATCTAGGTGAAGATCCTTT

TTGATAATCTCATGACCAAAATCCCTTAACGTGAGTTTTCGTTCCACTGAGCGTCAGACCCCGTAGAAAAGATCAAAG

GATCTTCTTGAGATCCTTTTTTTCTGCGCGTAATCTGCTGCTTGCAAACAAAAAAACCACCGCTACCAGCGGTGGTTTG

TTTGCCGGATCAAGAGCTACCAACTCTTTTTCCGAAGGTAACTGGCTTCAGCAGAGCGCAGATACCAAATACTGTTCTT

CTAGTGTAGCCGTAGTTAGGCCACCACTTCAAGAACTCTGTAGCACCGCCTACATACCTCGCTCTGCTAATCCTGTTAC

CAGTGGCTGCTGCCAGTGGCGATAAGTCGTGTCTTACCGGGTTGGACTCAAGACGATAGTTACCGGATAAGGCGCAG

CGGTCGGGCTGAACGGGGGGTTCGTGCACACAGCCCAGCTTGGAGCGAACGACCTACACCGAACTGAGATACCTACA

GCGTGAGCTATGAGAAAGCGCCACGCTTCCCGAAGGGAGAAAGGCGGACAGGTATCCGGTAAGCGGCAGGGTCGG

AACAGGAGAGCGCACGAGGGAGCTTCCAGGGGGAAACGCCTGGTATCTTTATAGTCCTGTCGGGTTTCGCCACCTCT

GACTTGAGCGTCGATTTTTGTGATGCTCGTCAGGGGGGCGGAGCCTATGGAAAAACGCCAGCAACGCGGCCTTTTTA

CGGTTCCTGGCCTTTTGCTGGCCTTTTGCTCACATGT
```

Example 3. PKLR Correction in PKD-HSPCs

Figure 15:
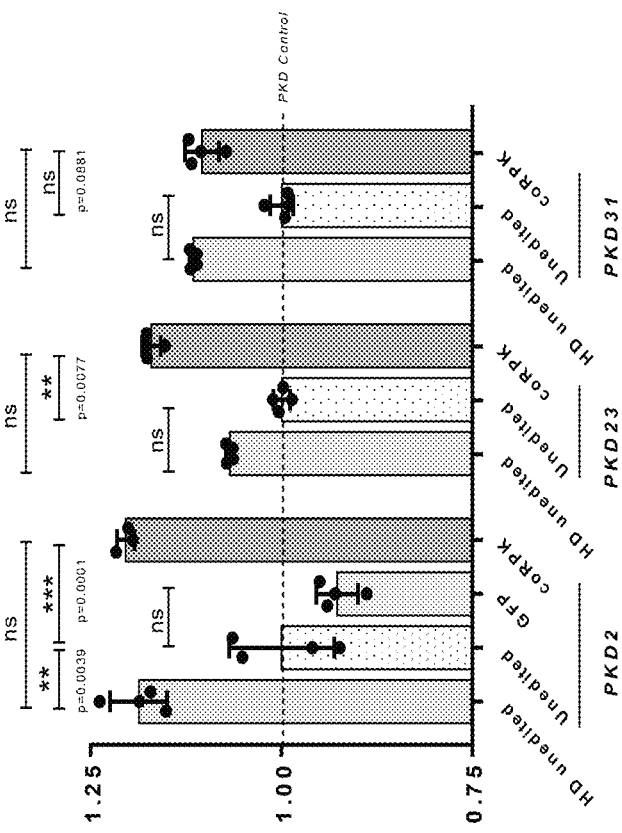
FIG. 15. Gene editing in HSPCs from a PKD patients with erythroid differentiation capacity. A) Specific in-out PCR verified the correct integration of therapeutic donor (coRPK-AAV+RNP) at both 5' (LHA) and 3' (RHA) junctions. B) ATP quantification of the erythroid cells derived from edited HSPCs of three PKD patients relativized to the erythroid cells derived from unedited PKD-HSPCs. HD unedited: HSPCs from a healthy donor that had undergone erythroid differentiation in vitro; PKD unedited: HSPCs from a PKD patient that had undergone erythroid differentiation in vitro; PKD GFP/coRPK: HSPCs from a PKD patient that had undergone gene editing with GFP-AAV or coRPK-AAV and subsequent erythroid differentiation in vitro. Kruskal-Wallis multiple comparison test was performed; P value is indicated in the figure. ns=not significant.
Figure 15:
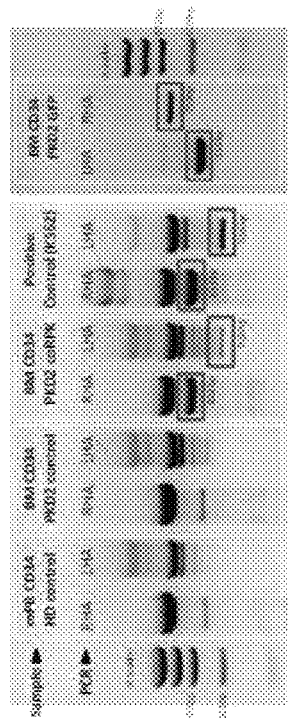
Figure 16:
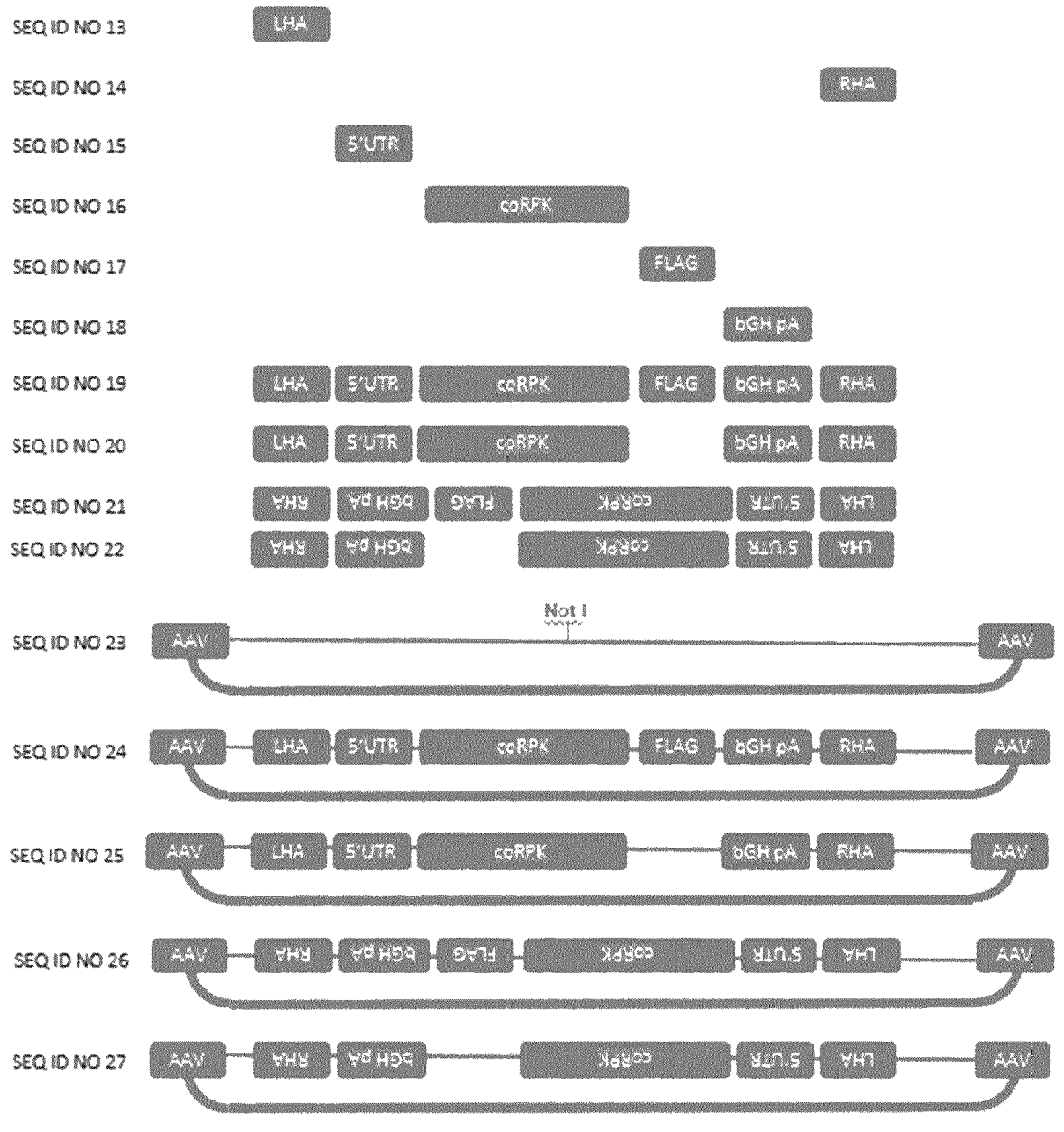
FIG. 16. Schematic view of sequences 13 to 27.

In order to assess the therapeutic potential of our gene editing system, human HSPCs from four PKD patients carrying mutations in PKLR gene and HD-CD34$^+$ cells were pre-stimulated for 48 hours. Then, the cells were nucleofected and transduced with rAAVs. 24 hours after gene editing procedure, cells were collected and transferred to an erythroid differentiation medium. Erythroid differentiation process was evaluated during all the experiment by FACS, observing no differences in the maturation profile between healthy and genetically edited donor samples. On day 14, cells were collected and genomic and functional analyses were performed. Firstly, in the samples from one patient (PKD2), vector integration was assessed by specific PCR of the 3' and 5' junctions. As observed in FIG. 15C, we could detect the specific bands in the patient's samples. Furthermore, functional analysis based in the quantification of the ATP of erythroid cells was performed. PKD cells unedited or edited with GFP-AAV produced low levels of ATP. However, erythroid cells that arise from PKD-HSPCs that had undergone gene editing with the RNP and coRPK-AAV were able to restore the ATP levels close to HD cells (FIG. 15D). Altogether, our data indicated that gene editing at PKLR gene can restore the in vitro functionality of patient's erythroid cells.

SEQUENCE LISTING

```
<160> NUMBER OF SEQ ID NOS: 45

<210> SEQ ID NO 1
<211> LENGTH: 20
<212> TYPE: DNA
<213> ORGANISM: Artificial Sequence
<220> FEATURE:
<223> OTHER INFORMATION: SG1

<400> SEQUENCE: 1
ctgcgggacc atggaatgag                                      20

<210> SEQ ID NO 2
<211> LENGTH: 20
<212> TYPE: DNA
<213> ORGANISM: Artificial Sequence
<220> FEATURE:
<223> OTHER INFORMATION: SG2

<400> SEQUENCE: 2
tggggacagg gtggcctact                                      20

<210> SEQ ID NO 3
<211> LENGTH: 20
<212> TYPE: DNA
<213> ORGANISM: Artificial Sequence
<220> FEATURE:
<223> OTHER INFORMATION: SG3

<400> SEQUENCE: 3
aaaactgctg gtcttatcta                                      20

<210> SEQ ID NO 4
<211> LENGTH: 20
<212> TYPE: DNA
<213> ORGANISM: Artificial Sequence
<220> FEATURE:
<223> OTHER INFORMATION: SG4

<400> SEQUENCE: 4
agaaaagggg cacacccagt                                      20

<210> SEQ ID NO 5
<211> LENGTH: 20
<212> TYPE: DNA
<213> ORGANISM: Artificial Sequence
<220> FEATURE:
<223> OTHER INFORMATION: SG5

<400> SEQUENCE: 5
tggtcccgca gccccaggcc                                      20
```

-continued

```
<210> SEQ ID NO 6
<211> LENGTH: 20
<212> TYPE: DNA
<213> ORGANISM: Artificial Sequence
<220> FEATURE:
<223> OTHER INFORMATION: SG6

<400> SEQUENCE: 6
ctccctctca ttccatggtc                                             20

<210> SEQ ID NO 7
<211> LENGTH: 20
<212> TYPE: DNA
<213> ORGANISM: Artificial Sequence
<220> FEATURE:
<223> OTHER INFORMATION: SG7

<400> SEQUENCE: 7
cagccccagg cccacactga                                             20

<210> SEQ ID NO 8
<211> LENGTH: 20
<212> TYPE: DNA
<213> ORGANISM: Artificial Sequence
<220> FEATURE:
<223> OTHER INFORMATION: SG8

<400> SEQUENCE: 8
ttccatggtc ccgcagcccc                                             20

<210> SEQ ID NO 9
<211> LENGTH: 20
<212> TYPE: DNA
<213> ORGANISM: Artificial Sequence
<220> FEATURE:
<223> OTHER INFORMATION: SG9

<400> SEQUENCE: 9
cactgaaagc atgtcgatcc                                             20

<210> SEQ ID NO 10
<211> LENGTH: 20
<212> TYPE: DNA
<213> ORGANISM: Artificial Sequence
<220> FEATURE:
<223> OTHER INFORMATION: SG10

<400> SEQUENCE: 10
aaactgctgg tcttatctaa                                             20

<210> SEQ ID NO 11
<211> LENGTH: 20
<212> TYPE: RNA
<213> ORGANISM: Artificial Sequence
<220> FEATURE:
<223> OTHER INFORMATION: crRNA SG1 sequence (as RNA)

<400> SEQUENCE: 11
cugcgggacc auggaaugag                                             20

<210> SEQ ID NO 12
<211> LENGTH: 61
<212> TYPE: RNA
<213> ORGANISM: Artificial Sequence
<220> FEATURE:
<223> OTHER INFORMATION: sgRNA SG1 sequence (as RNA)
```

-continued

<400> SEQUENCE: 12

```
cugcgggacc auggaaugag guuuuagagc uagaaauagc aaguuaaaua aggcuagucc      60
g                                                                      61
```

<210> SEQ ID NO 13
<211> LENGTH: 425
<212> TYPE: DNA
<213> ORGANISM: Artificial Sequence
<220> FEATURE:
<223> OTHER INFORMATION: LHA (left homologous arm)

<400> SEQUENCE: 13

```
cagagtggtg aaggcactct gcatttcttg gttgagacag agaaaaaaag tggtcagaac     60
tgggtaaccc tcccccacc atattatcac agtgatccct tttgtctttc ttcaggctcc     120
agccccaccc tacagccct gctccctgga ttcactagag ctaacttcag taaagtacaa     180
agaaaatggg gccatatgac tggccaaaaa aaaaatatct attcacgtgg atgaccagat    240
agtatgaatg gattgaaaat ttatcaggaa aaaaggatga gaggaaatgc caggagatga    300
gggcagagag caggccgttc tgggggaggg attctgtggg gacagggtgg cctactgggt    360
gtgccccttt tctcttctct gtctccctta gataagacca gcagttttgt catcctctcc    420
ctctc                                                                 425
```

<210> SEQ ID NO 14
<211> LENGTH: 425
<212> TYPE: DNA
<213> ORGANISM: Artificial Sequence
<220> FEATURE:
<223> OTHER INFORMATION: RHA (right homology arm)

<400> SEQUENCE: 14

```
gtcccgcagc cccaggccca cactgaaagc atgtcgatcc aggagaacat atcatccctg     60
cagcttcggt catgggtctc taagtcccaa agagacttag caaagtccat cctgattggg    120
gctccaggag gtaagaaggg gagacagaag ccatggaaca taggaggaaa atgagggtga    180
aaactaggag ccagggtgga gggcataaat gatccacatc agccactggc taggtgggtt    240
ttggagagga acgtacgttc ttcagagcct cccgtgtgtt aaattatgga ccctggcctg    300 ggtctttttcc aggccctata ggcaggccag agccacagca tgtaagccac ggggcactcc    360
cgtggttcct ggactctggc ccctggcata cagggcttcc aatggaacag gagacagtgg    420
tgaca                                                                 425
```

<210> SEQ ID NO 15
<211> LENGTH: 40
<212> TYPE: DNA
<213> ORGANISM: Artificial Sequence
<220> FEATURE:
<223> OTHER INFORMATION: 5'UTR sequence

<400> SEQUENCE: 15

```
ttccatggtc ccgcagcccc aggcccacac tgaaagcatg                            40
```

<210> SEQ ID NO 16
<211> LENGTH: 1719
<212> TYPE: DNA
<213> ORGANISM: Artificial Sequence
<220> FEATURE:
<223> OTHER INFORMATION: coRPK cDNA -continued

<400> SEQUENCE: 16
agcatccagg aaaatatcag ctctctgcag ctgcggtcct gggtgtccaa gagccagaga      60
gacctggcca agagcatcct gatcggagcc cctggcggac cagccggata cctgagaagg     120
gctagcgtgg cccagctgac ccaggaactg ggcaccgcct ttttccagca gcagcagctg     180
ccagccgcca tggccgacac ctttctggaa cacctgtgcc tgctggacat cgactctgag     240
cccgtggccg ccagaagcac cagcatcatt gccaccatcg ccctgccag cagaagcgtg      300 gagcggctga aagagatgat caaggccggc atgaatatcg cccggctgaa cttctcccac     360
ggcagccacg agtaccacgc agagagcatt gccaacgtcc gggaggccgt ggagagcttt     420
gccggcagcc ccctgagcta cagacccgtg gccattgccc tggacaccaa gggccccgag     480
atcagaacag gaattctgca gggagggcct gagagcgagg tggagctggt gaagggcagc     540
caagtgctgg tgaccgtgga ccccgccttc agaaccagag gcaacgccaa cacagtgtgg     600
gtggactacc ccaacatcgt gcgggtggtg cctgtgggcg gcagaatcta catcgacgac     660
ggcctgatca gctggtggt gcagaagatc ggacctgagg gcctggtgac ccaggtcgag      720
aatggcggcg tgctgggcag cagaaagggc gtgaatctgc caggcgccca ggtggacctg     780
cctggcctgt ctgagcagga cgtgagagac ctgagatttg gcgtggagca cggcgtggac     840
atcgtgttcg ccagcttcgt gcggaaggcc tctgatgtgg ccgccgtgag agccgctctg     900
ggccctgaag gccacggcat caagatcatc agcaagatcg agaaccacga gggcgtgaag     960
cggttcgacg agatcctgga agtgtccgac ggcatcatgg tggccagagg cgacctgggc    1020
atcgagatcc ccgccgagaa ggtgttcctg gcccagaaaa tgatgatcgg acggtgcaac    1080
ctggccggca aacctgtggt gtgcgccacc cagatgctgg aaagcatgat caccaagccc    1140
agacccacca gagccgagac aagcgacgtg gccaacgccg tgctggatgg cgctgactgc    1200
atcatgctgt ccggcgagac agccaagggc aacttccccg tggaggccgt gaagatgcag    1260
cacgccattg ccagagaagc cgaggccgcc gtgtaccacc ggcagctgtt cgaggaactg    1320
cggagagccg cccctctgag cagagatccc accgaagtga ccgccatcgg agccgtggaa    1380
gccgccttca gtgctgcgc cgctgcaatc atcgtgctga ccaccacagg cagaagcgcc     1440
cagctgctgt ccagatacag acccagagcc gccgtgatcg ccgtgacaag atccgcccag    1500
gccgctagac aggtccacct gtgcagaggc gtgttccccc tgctgtaccg ggagcctccc    1560
gaggccatct gggccgacga cgtggacaga cgggtgcagt tcggcatcga gagcggcaag    1620
ctgcggggct tcctgagagt gggcgacctg gtgatcgtgg tgacaggctg gcggcctggc    1680
agcggctaca ccaacatcat gagggtgctg tccatcagc                           1719

<210> SEQ ID NO 17
<211> LENGTH: 27
<212> TYPE: DNA
<213> ORGANISM: Artificial Sequence
<220> FEATURE:
<223> OTHER INFORMATION: FLAG-Tag

<400> SEQUENCE: 17
gactacaaag acgatgacga taaatga                                           27

<210> SEQ ID NO 18
<211> LENGTH: 225
<212> TYPE: DNA
<213> ORGANISM: Artificial Sequence
<220> FEATURE:
<223> OTHER INFORMATION: bGH poly(A) signal -continued

<400> SEQUENCE: 18

```
ctgtgccttc tagttgccag ccatctgttg tttgcccctc ccccgtgcct tccttgaccc      60
tggaaggtgc cactcccact gtcctttcct aataaaatga ggaaattgca tcgcattgtc     120
tgagtaggtg tcattctatt ctgggggtg gggtgggca ggacagcaag ggggaggatt       180
gggaagacaa tagcaggcat gctggggatg cggtgggctc tatgg                     225
```

```
<210> SEQ ID NO 19
<211> LENGTH: 2884
<212> TYPE: DNA
<213> ORGANISM: Artificial Sequence
<220> FEATURE:
<223> OTHER INFORMATION: LHA-5'UTR-coRPK-FLAG-bGH poly(A)-RHA
```

<400> SEQUENCE: 19

```
cagagtggtg aaggcactct gcatttcttg gttgagacag agaaaaaaag tggtcagaac      60
tgggtaaccc tccccccacc atattatcac agtgatccct tttgtctttc ttcaggctcc     120
agccccaccc tacagcccct gctccctgga ttcactagag ctaacttcag taaagtacaa     180
agaaaatggg gccatatgac tggccaaaaa aaaaatatct attcacgtgg atgaccagat     240
agtatgaatg gattgaaaat ttatcaggaa aaaaggatga gaggaaatgc caggagatga     300
gggcagagag caggccgttc tgggggaggg attctgtggg gacagggtgg cctactgggt     360
gtgccccttt tctcttctct gtctcccttta gataagacca gcagttttgt catcctctcc     420
ctctcttcca tggtcccgca gccccaggcc cacactgaaa gcatgagcat ccaggaaaat     480
atcagctctc tgcagctgcg gtcctgggtg tccaagagcc agagagacct ggccaagagc     540
atcctgatcg gagcccctgg cggaccagcc ggatacctga aagggctag cgtggcccag      600 ctgacccagg aactgggcac cgccttttc cagcagcagc agctgccagc cgccatggcc      660
gacacctttc tggaacacct gtgcctgctg gacatcgact ctgagcccgt ggccgccaga     720
agcaccagca tcattgccac catcggccct gccagcagaa gcgtggagcg gctgaaagag     780
atgatcaagg ccggcatgaa tatcgcccgg ctgaacttct cccacggcag ccacgagtac     840
cacgcagaga gcattgccaa cgtccgggag gccgtggaga gctttgccgg cagcccctg      900 agctacagac ccgtggccat tgccctggac accaagggcc ccgagatcag aacaggaatt     960
ctgcagggag ggcctgagag cgaggtggag ctggtgaagg cagccaagt gctggtgacc     1020 gtggaccccg ccttcagaac cagaggcaac gccaacacag tgtgggtgga ctaccccaac    1080
atcgtgcggg tggtgcctgt gggcggcaga atctacatcg acgacggcct gatcagcctg    1140
gtggtgcaga agatcggacc tgagggcctg gtgacccagg tcgagaatgg cggcgtgctg    1200
ggcagcagaa agggcgtgaa tctgccaggc gcccaggtgg acctgcctgg cctgtctgag    1260
caggacgtga gagacctgag atttggcgtg agcacggcg tggacatcgt gttcgccagc    1320
ttcgtgcgga aggcctctga tgtggccgcc gtgagagccg ctctgggccc tgaaggccac    1380
ggcatcaaga tcatcagcaa gatcgagaac cacgagggcg tgaagcggtt cgacgagatc    1440
ctggaagtgt ccgacggcat catggtggcc agaggcgacc tgggcatcga gatccccgcc    1500
gagaaggtgt tcctggccca gaaaatgatg atcggacggt gcaacctggc cggcaaacct    1560
gtggtgtgcg ccacccagat gctggaaagc atgatcacca gcccagacc caccagagcc    1620 gagacaagcg acgtggccaa cgccgtgctg atggcgctg actgcatcat gctgtccggc    1680
gagacagcca agggcaactt ccccgtggag gccgtgaaga tgcagcacgc cattgccaga    1740
```

-continued

```
gaagccgagg ccgccgtgta ccaccggcag ctgttcgagg aactgcggag agccgcccct    1800
ctgagcagag atcccaccga agtgaccgcc atcggagccg tggaagccgc cttcaagtgc    1860
tgcgccgctg caatcatcgt gctgaccacc acaggcagaa gcgcccagct gctgtccaga    1920
tacagaccca gagccgccgt gatcgccgtg acaagatccg cccaggccgc tagacaggtc    1980
cacctgtgca gaggcgtgtt ccccctgctg taccgggagc ctcccgaggc catctgggcc    2040
gacgacgtgg acagacgggt gcagttcggc atcgagagcg gcaagctgcg gggcttcctg    2100
agagtgggcg acctggtgat cgtggtgaca ggctggcggc ctggcagcgg ctacaccaac    2160
atcatgaggg tgctgtccat cagcgactac aaagacgatg acgataaatg aacgcgtgag    2220
ttacaaataa agcactgtgc cttctagttg ccagccatct gttgtttgcc cctcccccgt    2280
gccttccttg accctggaag gtgccactcc cactgtcctt tcctaataaa atgaggaaat    2340
tgcatcgcat tgtctgagta ggtgtcattc tattctgggg ggtggggtgg ggcaggacag    2400
caagggggag gattgggaag acaatagcag gcatgctggg gatgcggtgg gctctatggg    2460
tcccgcagcc ccaggcccac actgaaagca tgtcgatcca ggagaacata tcatccctgc    2520
agcttcggtc atgggtctct aagtcccaaa gagacttagc aaagtccatc ctgattgggg    2580
ctccaggagg taagaagggg agacagaagc catggaacat aggaggaaaa tgagggtgaa    2640
aactaggagc cagggtggag ggcataaatg atccacatca gccactggct aggtgggttt    2700
tggagaggaa cgtacgttct tcagagcctc ccgtgtgtta aattatggac cctggcctgg    2760
gtcttttcca ggccctatag gcaggccaga gccacagcat gtaagccacg gggcactccc    2820
gtggttcctg gactctggcc cctggcatac agggcttcca atggaacagg agacagtggt    2880
gaca                                                                 2884

<210> SEQ ID NO 20
<211> LENGTH: 2860
<212> TYPE: DNA
<213> ORGANISM: Artificial Sequence
<220> FEATURE:
<223> OTHER INFORMATION: LHA-5'UTR-coRPK-bGH poly(A)-RHA

<400> SEQUENCE: 20
cagagtggtg aaggcactct gcatttcttg gttgagacag agaaaaaaag tggtcagaac     60
tgggtaaccc tcccccacc atattatcac agtgatccct tttgtctttc ttcaggctcc    120
agccccaccc tacagcccct gctccctgga ttcactagag ctaacttcag taaagtacaa    180
agaaaatggg gccatatgac tggccaaaaa aaaaatatct attcacgtgg atgaccagat    240
agtatgaatg gattgaaaat ttatcaggaa aaaaggatga gaggaaatgc caggagatga    300
gggcagagag caggccgttc tggggggaggg attctgtggg gacagggtgg cctactgggt    360
gtgccccttt tctcttctct gtctccctta gataagacca gcagttttgt catcctctcc    420
ctctcttcca tggtcccgca gccccaggcc cacactgaaa gcatgagcat ccaggaaaat    480
atcagctctc tgcagctgcg gtcctgggtg tccaagagcc agagagacct ggccaagagc    540
atcctgatcg gagccctgg cggaccagcc ggatacctga aagggctag cgtggcccag    600 ctgacccagg aactgggcac cgcctttttc cagcagcagc agctgccagc cgccatggcc    660
gacacctttc tggaacacct gtgcctgctg gacatcgact ctgagcccgt ggccgccaga    720
agcaccagca tcattgccac catcggccct gccagcagaa gcgtggagcg gctgaaagag    780
atgatcaagg ccggcatgaa tatcgcccgg ctgaacttct cccacggcag ccacgagtac    840
cacgcagaga gcattgccaa cgtccgggag gccgtggaga gctttgccgg cagccccctg    900
```

```
agctacagac ccgtggccat tgccctggac accaagggcc ccgagatcag aacaggaatt      960
ctgcagggag ggcctgagag cgaggtggag ctggtgaagg gcagccaagt gctggtgacc     1020
gtggaccccg ccttcagaac cagaggcaac gccaacacag tgtgggtgga ctaccccaac     1080
atcgtgcggg tggtgcctgt gggcggcaga atctacatcg acgacggcct gatcagcctg     1140
gtggtgcaga agatcggacc tgagggcctg gtgacccagg tcgagaatgg cggcgtgctg     1200
ggcagcagaa agggcgtgaa tctgccaggc gcccaggtgg acctgcctgg cctgtctgag     1260
caggacgtga gagacctgag atttggcgtg gagcacggcg tggacatcgt gttcgccagc     1320
ttcgtgcgga aggcctctga tgtggccgcc gtgagagccg ctctgggccc tgaaggccac     1380
ggcatcaaga tcatcagcaa gatcgagaac cacgagggcg tgaagcggtt cgacgagatc     1440
ctggaagtgt ccgacggcat catggtggcc agaggcgacc tgggcatcga gatccccgcc     1500
gagaaggtgt cctggcccca gaaaatgatg atcggacggt gcaacctggc cggcaaacct     1560
gtggtgtgcg ccacccagat gctggaaagc atgatcacca gcccagacc caccagagcc      1620 gagacaagcg acgtggccaa cgccgtgctg gatggcgctg actgcatcat gctgtccggc     1680
gagacagcca agggcaactt ccccgtggag gccgtgaaga tgcagcacgc cattgccaga     1740
gaagccgagg ccgccgtgta ccaccggcag ctgttcgagg aactgcggag agccgcccct     1800
ctgagcagag atcccaccga agtgaccgcc atcggagccg tggaagccgc cttcaagtgc     1860
tgcgccgctg caatcatcgt gctgaccacc acaggcagaa gcgcccagct gctgtccaga     1920
tacagaccca gagccgccgt gatcgccgtg acaagatccg cccaggccgc tagacaggtc     1980
cacctgtgca gaggcgtgtt ccccctgctg taccgggagc ctcccgaggc catctgggcc     2040
gacgacgtgg acagacgggt gcagttcggc atcgagagcg gcaagctgcg gggcttcctg     2100
agagtgggcg acctggtgat cgtggtgaca ggctggcggc ctggcagcgg ctacaccaac     2160
atcatgaggg tgctgtccat cagctgaacg cgtgagttac aaataaagca ctgtgccttc     2220
tagttgccag ccatctgttg tttgcccctc ccccgtgcct tccttgaccc tggaaggtgc     2280
cactcccact gtcctttcct aataaaatga ggaaattgca tcgcattgtc tgagtaggtg     2340
tcattctatt ctggggggtg gggtggggca ggacagcaag ggggaggatt gggaagacaa     2400
tagcaggcat gctggggatg cggtgggctc tatgggtccc gcagcccag gcccacactg      2460 aaagcatgtc gatccaggag aacatatcat ccctgcagct tcggtcatgg gtctctaagt     2520
cccaaagaga cttagcaaag tccatcctga ttggggctcc aggaggtaag aaggggagac     2580
agaagccatg gaacatagga ggaaaatgag ggtgaaaact aggagccagg gtggagggca     2640
taaatgatcc acatcagcca ctggctaggt gggttttgga gaggaacgta cgttcttcag     2700
agcctcccgt gtgttaaatt atggaccctg gcctgggtct tttccaggcc ctataggcag     2760
gccagagcca cagcatgtaa gccacggggc actcccgtgg ttcctggact ctggccctg      2820 gcatacaggg cttccaatgg aacaggagac agtggtgaca                           2860
```

```
<210> SEQ ID NO 21
<211> LENGTH: 2884
<212> TYPE: DNA
<213> ORGANISM: Artificial Sequence
<220> FEATURE:
<223> OTHER INFORMATION: LHA-5'UTR-coRPK-bGH poly(A)-RHA

<400> SEQUENCE: 21
tgtcaccact gtctcctgtt ccattggaag ccctgtatgc caggggccag agtccaggaa       60
```

-continued

```
ccacgggagt gccccgtggc ttacatgctg tggctctggc ctgcctatag ggcctggaaa    120
agacccaggc cagggtccat aatttaacac acgggaggct ctgaagaacg tacgttcctc    180
tccaaaaccc acctagccag tggctgatgt ggatcattta tgccctccac cctggctcct    240
agttttcacc ctcattttcc tcctatgttc catggcttct gtctcccctt cttacctcct    300
ggagccccaa tcaggatgga ctttgctaag tctctttggg acttagagac ccatgaccga    360
agctgcaggg atgatatgtt ctcctggatc gacatgcttt cagtgtgggc ctggggctgc    420
gggacccata gagcccaccg catccccagc atgcctgcta ttgtcttccc aatcctcccc    480
cttgctgtcc tgccccaccc caccccccag aatagaatga cacctactca gacaatgcga    540
tgcaatttcc tcattttatt aggaaaggac agtgggagtg gcaccttcca gggtcaagga    600
aggcacgggg gaggggcaaa caacagatgg ctggcaacta gaaggcacag tgctttattt    660
gtaactcacg cgttcattta tcgtcatcgt ctttgtagtc gctgatggac agcaccctca    720
tgatgttggt gtagccgctg ccaggccgcc agcctgtcac cacgatcacc aggtcgccca    780
ctctcaggaa gccccgcagc ttgccgctct cgatgccgaa ctgcacccgt ctgtccacgt    840
cgtcggccca gatggcctcg ggaggctccc ggtacagcag ggggaacacg cctctgcaca    900
ggtggacctg tctagcggcc tgggcggatc ttgtcacggc gatcacggcg ctctgggtc     960 tgtatctgga cagcagctgg gcgcttctgc ctgtggtggt cagcacgatg attgcagcgg   1020
cgcagcactt gaaggcggct ccacggctc cgatggcggt cacttcggtg ggatctctgc    1080
tcagaggggc ggctctccgc agttcctcga acagctgccg gtggtacacg gcggcctcgg   1140
cttctctggc aatggcgtgc tgcatcttca cggcctccac ggggaagttg cccttggctg   1200
tctcgccgga cagcatgatg cagtcagcgc catccagcac ggcgttggcc acgtcgcttg   1260
tctcggctct ggtgggtctg ggcttggtga tcatgctttc cagcatctgg gtggcgcaca   1320
ccacaggttt gccggccagg ttgcaccgtc cgatcatcat tttctgggcc aggaacacct   1380
tctcggcggg gatctcgatg cccaggtcgc ctctggccac catgatgccg tcggacactt   1440
ccaggatctc gtcgaaccgc ttcacgccct cgtggttctc gatcttgctg atgatcttga   1500
tgccgtggcc ttcagggccc agagcggctc tcacggcggc cacatcagag gccttccgca   1560
cgaagctggc gaacacgatg tccacgccgt gctccacgcc aaatctcagg tctctcacgt   1620
cctgctcaga caggccaggc aggtccacct gggcgcctgg cagattcacg ccctttctgc   1680
tgcccagcac gccgccattc tcgacctggg tcaccaggcc ctcaggtccg atcttctgca   1740
ccaccaggct gatcaggccg tcgtcgatgt agattctgcc gcccacaggc accacccgca   1800
cgatgttggg gtagtccacc cacactgtgt tggcgttgcc tctggttctg aaggcggggt   1860
ccacggtcac cagcacttgg ctgcccttca ccagctccac ctcgctctca ggccctccct   1920
gcagaattcc tgttctgatc tcggggccct tggtgtccag ggcaatggcc acgggtctgt   1980
agctcagggg gctgccggca aagctctcca cggcctcccg gacgttggca atgctctctg   2040
cgtggtactc gtggctgccg tgggagaagt tcagccgggc gatattcatg ccggccttga   2100
tcatctcttt cagccgctcc acgcttctgc tggcagggcc gatggtggca atgatgctgg   2160
tgcttctggc ggccacgggc tcagagtcga tgtccagcag gcacaggtgt tccagaaagg   2220
tgtcggccat ggcggctggc agctgctgct gctggaaaaa ggcggtgccc agttcctggg   2280
tcagctgggc cacgctagcc cttctcaggt atccggctgg tccgccaggg gctccgatca   2340
ggatgctctt ggccaggtct ctctggctct tggacaccca ggaccgcagc tgcagagagc   2400
tgatattttc ctggatgctc atgctttcag tgtgggcctg gggctgcggg accatggaag   2460
```

-continued

```
agagggagag gatgacaaaa ctgctggtct tatctaaggg agacagagaa gagaaaaggg      2520
gcacacccag taggccaccc tgtccccaca gaatccctcc cccagaacgg cctgctctct      2580
gccctcatct cctggcattt cctctcatcc tttttttcctg ataaattttc aatccattca     2640
tactatctgg tcatccacgt gaatagatat tttttttttg gccagtcata tggccccatt      2700
ttctttgtac tttactgaag ttagctctag tgaatccagg gagcagggggc tgtagggtgg     2760 ggctggagcc tgaagaaaga caaaagggat cactgtgata atatggtggg gggagggtta      2820
cccagttctg accacttttt ttctctgtct caaccaagaa atgcagagtg ccttcaccac      2880
tctg                                                                   2884
```

```
<210> SEQ ID NO 22
<211> LENGTH: 2860
<212> TYPE: DNA
<213> ORGANISM: Artificial Sequence
<220> FEATURE:
<223> OTHER INFORMATION: LHA-5'UTR-coRPK-bGH poly(A)-RHA

<400> SEQUENCE: 22
```

```
tgtcaccact gtctcctgtt ccattggaag ccctgtatgc caggggccag agtccaggaa        60
ccacgggagt gccccgtggc ttacatgctg tggctctggc ctgcctatag ggcctggaaa       120
agacccaggc cagggtccat aatttaacac acgggaggct ctgaagaacg tacgttcctc       180
tccaaaaccc acctagccag tggctgatgt ggatcattta tgccctccac cctggctcct      240
agttttcacc ctcattttcc tcctatgttc catggcttct gtctcccctt cttacctcct      300
ggagccccaa tcaggatgga ctttgctaag tctctttggg acttagagac ccatgaccga      360
agctgcaggg atgatatgtt ctcctggatc gacatgcttt cagtgtgggc ctggggctgc      420
gggacccata gagcccaccg catccccagc atgcctgcta ttgtcttccc aatcctcccc      480
cttgctgtcc tgccccaccc cacccccag aatagaatga cacctactca gacaatgcga       540
tgcaatttcc tcattttatt aggaaaggac agtgggagtg gcaccttcca gggtcaagga      600
aggcacgggg gagggggcaaa caacagatgg ctggcaacta gaaggcacag tgctttattt     660
gtaactcacg cgttcagctg atggacagca ccctcatgat gttggtgtag ccgctgccag      720
gccgccagcc tgtcaccacg atcaccaggt cgcccactct caggaagccc cgcagcttgc      780
cgctctcgat gccgaactgc acccgtctgt ccacgtcgtc ggcccagatg gcctcgggag      840
gctcccggta cagcaggggg aacacgcctc tgcacaggtg gacctgtcta gcggcctggg      900
cggatcttgt cacggcgatc acggcggctc tgggtctgta tctggacagc agctgggcgc      960
ttctgcctgt ggtggtcagc acgatgattg cagcggcgca gcacttgaag gcggcttcca     1020
cggctccgat ggcggtcact tcggtgggat ctctgctcag aggggcggct ctccgcagtt     1080
cctcgaacag ctgccggtgg tacacggcgg cctcggcttc tctggcaatg gcgtgctgca    1140
tcttcacggc ctccacgggg aagttgccct ggctgtctc gccggacagc atgatgcagt      1200
cagcgccatc cagcacggcg ttggccacgt cgcttgtctc ggctctggtg ggtctgggct     1260
tggtgatcat gctttccagc atctgggtgg cgcacaccac aggtttgccg gccaggttgc     1320
accgtccgat catcattttc tgggccagga acaccttctc ggcgggggatc tcgatgccca     1380 ggtcgcctct ggccaccatg atgccgtcgg acacttccag gatctcgtcg aaccgcttca     1440
cgccctcgtg gttctcgatc ttgctgatga tcttgatgcc gtggccttca gggcccagag     1500
cggctctcac ggcggccaca tcagaggcct tccgcacgaa gctggcgaac acgatgtcca     1560
```

-continued

```
cgccgtgctc cacgccaaat ctcaggtctc tcacgtcctg ctcagacagg ccaggcaggt    1620
ccacctgggc gcctggcaga ttcacgccct ttctgctgcc cagcacgccg ccattctcga    1680
cctgggtcac caggccctca ggtccgatct tctgcaccac caggctgatc aggccgtcgt    1740
cgatgtagat tctgccgccc acaggcacca cccgcacgat gttggggtag tccacccaca    1800
ctgtgttggc gttgcctctg gttctgaagg cggggtccac ggtcaccagc acttggctgc    1860
ccttcaccag ctccacctcg ctctcaggcc ctccctgcag aattcctgtt ctgatctcgg    1920
ggcccttggt gtccagggca atggccacgg gtctgtagct caggggctg ccggcaaagc    1980 tctccacggc ctcccggacg ttggcaatgc tctctgcgtg gtactcgtgg ctgccgtggg    2040
agaagttcag ccgggcgata ttcatgccgg ccttgatcat ctctttcagc cgctccacgc    2100
ttctgctggc agggccgatg gtggcaatga tgctggtgct tctggcggcc acgggctcag    2160
agtcgatgtc cagcaggcac aggtgttcca gaaaggtgtc ggccatggcg gctggcagct    2220
gctgctgctg gaaaaaggcg gtgcccagtt cctgggtcag ctgggccacg ctagcccttc    2280
tcaggtatcc ggctggtccg ccaggggctc cgatcaggat gctcttggcc aggtctctct    2340
ggctcttgga cacccaggac cgcagctgca gagagctgat attttcctgg atgctcatgc    2400
tttcagtgtg ggcctggggc tgcgggacca tggaagagag ggagaggatg acaaaactgc    2460
tggtcttatc taagggagac agagaagaga aaaggggcac acccagtagg ccaccctgtc    2520
cccacagaat ccctccccca gaacggcctg ctctctgccc tcatctcctg gcatttcctc    2580
tcatcctttt ttcctgataa attttcaatc cattcatact atctggtcat ccacgtgaat    2640 agatatttt tttttggcca gtcatatggc cccattttct ttgtactta ctgaagttag    2700 ctctagtgaa tccagggagc aggggctgta gggtggggct ggagcctgaa gaaagacaaa    2760
agggatcact gtgataatat ggtgggggga gggttaccca gttctgacca ctttttttct    2820
ctgtctcaac caagaaatgc agagtgcctt caccactctg                         2860
```

<210> SEQ ID NO 23
<211> LENGTH: 2876
<212> TYPE: DNA
<213> ORGANISM: Artificial Sequence
<220> FEATURE:
<223> OTHER INFORMATION: AAV backbone

<400> SEQUENCE: 23

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcag gaacccctag tgatggagtt ggccactccc tctctgcgcg    180
ctcgctcgct cactgaggcc gggcgaccaa aggtcgcccg acgcccgggc tttgcccggg    240
cggcctcagt gagcgagcga gcgcgcagct gcctgcaggg gcgcctgatg cggtattttc    300
tccttacgca tctgtgcggt atttcacacc gcatacgtca aagcaaccat agtacgcgcc    360
ctgtagcggc gcattaagcg cggcgggtgt ggtggttacg cgcagcgtga ccgctacact    420
tgccagcgcc ctagcgcccg ctcctttcgc tttcttccct tcctttctcg ccacgttcgc    480
cggctttccc cgtcaagctc taaatcgggg gctcccttta gggttccgat ttagtgcttt    540
acggcacctc gaccccaaaa aacttgattt gggtgatggt tcacgtagtg gccatcgcc    600 ctgatagacg gtttttcgcc ctttgacgtt ggagtccacg ttctttaata gtggactctt    660
gttccaaact ggaacaacac tcaaccctat ctcgggctat tctttttgatt tataagggat    720 tttgccgatt tcggcctatt ggttaaaaaa tgagctgatt taacaaaaat ttaacgcgaa    780
```

-continued

```
ttttaacaaa atattaacgt ttacaatttt atggtgcact ctcagtacaa tctgctctga      840
tgccgcatag ttaagccagc cccgacaccc gccaacaccc gctgacgcgc cctgacgggc      900
ttgtctgctc ccggcatccg cttacagaca agctgtgacc gtctccggga gctgcatgtg      960
tcagaggttt tcaccgtcat caccgaaacg cgcgagacga aagggcctcg tgatacgcct     1020 attttttatag gttaatgtca tgataataat ggtttcttag acgtcaggtg gcacttttcg     1080
gggaaatgtg cgcggaaccc ctatttgttt atttttctaa atacattcaa atatgtatcc     1140
gctcatgaga caataaccct gataaatgct tcaataatat tgaaaaagga agagtatgag     1200
tattcaacat ttccgtgtcg cccttattcc ctttttttgcg gcattttgcc ttcctgtttt     1260
tgctcaccca gaaacgctgg tgaaagtaaa agatgctgaa gatcagttgg gtgcacgagt     1320
gggttacatc gaactggatc tcaacagcgg taagatcctt gagagttttc gccccgaaga     1380
acgttttcca atgatgagca cttttaaagt tctgctatgt ggcgcggtat tatcccgtat     1440
tgacgccggg caagagcaac tcggtcgccg catacactat tctcagaatg acttggttga     1500
gtactcacca gtcacagaaa agcatcttac ggatggcatg acagtaagag aattatgcag     1560
tgctgccata accatgagtg ataacactgc ggccaactta cttctgacaa cgatcggagg     1620
accgaaggag ctaaccgctt ttttgcacaa catgggggat catgtaactc gccttgatcg     1680
ttgggaaccg gagctgaatg aagccatacc aaacgacgag cgtgacacca cgatgcctgt     1740
agcaatggca acaacgttgc gcaaactatt aactggcgaa ctacttactc tagcttcccg     1800
gcaacaatta atagactgga tggaggcgga taaagttgca ggaccacttc tgcgctcggc     1860
ccttccggct ggctggttta ttgctgataa atctggagcc ggtgagcgtg ggtctcgcgg     1920
tatcattgca gcactggggc cagatggtaa gccctcccgt atcgtagtta tctacacgac     1980
ggggagtcag gcaactatgg atgaacgaaa tagacagatc gctgagatag gtgcctcact     2040
gattaagcat tggtaactgt cagaccaagt ttactcatat atactttaga ttgatttaaa     2100
acttcatttt taatttaaaa ggatctaggt gaagatcctt tttgataatc tcatgaccaa     2160
aatcccttaa cgtgagtttt cgttccactg agcgtcagac cccgtagaaa agatcaaagg     2220
atcttcttga tcctttttt ttctgcgcgt aatctgctgc ttgcaaacaa aaaaaccacc     2280
gctaccagcg gtggtttgtt tgccggatca gagctacca actctttttc cgaaggtaac     2340
tggcttcagc agagcgcaga taccaaatac tgtccttcta gtgtagccgt agttaggcca     2400
ccacttcaag aactctgtag caccgcctac atacctcgct ctgctaatcc tgttaccagt     2460
ggctgctgcc agtggcgata agtcgtgtct taccgggttg gactcaagac gatagttacc     2520
ggataaggcg cagcggtcgg gctgaacggg gggttcgtgc acacagccca gcttggagcg     2580
aacgacctac accgaactga gatacctaca gcgtgagcta tgagaaagcg ccacgcttcc     2640
cgaagggaga aaggcggaca ggtatccggt aagcggcagg gtcggaacag gagagcgcac     2700
gagggagctt ccaggggggaa acgcctggta tctttatagt cctgtcgggt ttcgccacct     2760
ctgacttgag cgtcgatttt tgtgatgctc gtcaggggg cggagcctat ggaaaaacgc     2820
cagcaacgcg gcctttttac ggttcctggc cttttgctgg ccttttgctc acatgt       2876
```

<210> SEQ ID NO 24
<211> LENGTH: 5899
<212> TYPE: DNA
<213> ORGANISM: Artificial Sequence
<220> FEATURE:
<223> OTHER INFORMATION: coRPK AAV used for pre-clinical studies

```
<400> SEQUENCE: 24
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggccgcca gagtggtgaa ggcactctgc atttcttggt tgagacagag     180
aaaaaaagtg gtcagaactg ggtaaccctc cccccaccat attatcacag tgatcccttt     240
tgtctttctt caggctccag ccccacccta cagccctgc tccctggatt cactagagct      300
aacttcagta aagtacaaag aaaatggggc catatgactg gccaaaaaaa aaatatctat     360
tcacgtggat gaccagatag tatgaatgga ttgaaaattt atcaggaaaa aaggatgaga     420
ggaaatgcca ggagatgagg gcagagagca ggccgttctg ggggagggat tctgtgggga     480
cagggtggcc tactgggtgt gccccttttc tcttctctgt ctcccttaga taagaccagc     540
agttttgtca tcctctccct ctcttccatg gtcccgcagc cccaggccca cactgaaagc     600
atgagcatcc aggaaaatat cagctctctg cagctgcggt cctgggtgtc caagagccag     660
agagacctgg ccaagagcat cctgatcgga gccctggcg gaccagccgg atacctgaga      720
agggctagcg tggcccagct gacccaggaa ctgggcaccg ccttttttcca gcagcagcag     780 ctgccagccg ccatggccga caccttttctg gaacacctgt gcctgctgga catcgactct     840
gagcccgtgg ccgccagaag caccagcatc attgccacca tcggccctgc cagcagaagc     900
gtggagcggc tgaaagagat gatcaaggcc ggcatgaata tcgcccggct gaacttctcc     960
cacggcagcc acgagtacca cgcagagagc attgccaacg tccgggaggc cgtggagagc    1020
tttgccggca gcccctgag ctacagaccc gtggccattg ccctggacac caagggcccc     1080
gagatcagaa caggaattct gcagggaggg cctgagagcg aggtggagct ggtgaagggc    1140
agccaagtgc tggtgaccgt ggaccccgcc ttcagaacca gaggcaacgc caacacagtg    1200
tgggtggact accccaacat cgtgcgggtg gtgcctgtgg cggcagaat ctacatcgac      1260 gacgcctga tcagcctggt ggtgcagaag atcggacctg agggcctggt gacccaggtc      1320
gagaatggcg gcgtgctggg cagcagaaag ggcgtgaatc tgccaggcgc ccaggtggac    1380
ctgcctggcc tgtctgagca ggacgtgaga gacctgagat ttggcgtgga gcacggcgtg    1440
gacatcgtgt tcgccagctt cgtgcggaag gcctctgatg tggccgccgt gagagccgct    1500
ctgggccctg aaggccacgg catcaagatc atcagcaaga tcgagaacca cgagggcgtg    1560
aagcggttcg acgagatcct ggaagtgtcc gacggcatca tggtggccag aggcgacctg    1620
ggcatcgaga tccccgccga gaaggtgttc ctggcccaga aaatgatgat cggacggtgc    1680
aacctggccg gcaaacctgt ggtgtgcgcc acccagatgc tggaaagcat gatcaccaag    1740
cccagaccca ccagagccga gacaagcgac gtggccaacg ccgtgctgga tggcgctgac    1800
tgcatcatgc tgtccggcga gacagccaag ggcaacttcc ccgtggaggc cgtgaagatg    1860
cagcacgcca ttgccagaga agccgaggcc gccgtgtacc accggcagct gttcgaggaa    1920
ctgcggagag ccgcccctct gagcagagat cccaccgaag tgaccgccat cggagccgtg    1980
gaagccgcct tcaagtgctg cgccgctgca atcatcgtgc tgaccaccac aggcagaagc    2040
gcccagctgc tgtccagata cagacccaga gccgccgtga tcgccgtgac aagatccgcc    2100
caggccgcta gacaggtcca cctgtgcaga ggcgtgttcc ccctgctgta ccgggagcct    2160
cccgaggcca tctgggccga cgacgtggac agacgggtgc agttcggcat cgagagcggc    2220
aagctgcggg gcttcctgag agtgggcgac ctggtgatcg tggtgacagg ctggcggcct    2280
ggcagcggct acaccaacat catgagggtg ctgtccatca gcgactacaa agacgatgac    2340
```

-continued

```
gataaatgaa cgcgtgagtt acaaataaag cactgtgcct tctagttgcc agccatctgt      2400
tgtttgcccc tcccccgtgc cttccttgac cctggaaggt gccactccca ctgtcctttc      2460
ctaataaaat gaggaaattg catcgcattg tctgagtagg tgtcattcta ttctgggggg      2520
tggggtgggg caggacagca aggggggagga ttgggaagac aatagcaggc atgctgggga     2580
tgcggtgggc tctatgggtc ccgcagcccc aggcccacac tgaaagcatg tcgatccagg      2640
agaacatatc atccctgcag cttcggtcat gggtctctaa gtcccaaaga gacttagcaa      2700
agtccatcct gattggggct ccaggaggta agaaggggag acagaagcca tggaacatag      2760
gaggaaaatg agggtgaaaa ctaggagcca gggtggaggg cataaatgat ccacatcagc      2820
cactggctag gtgggttttg gagaggaacg tacgttcttc agagcctccc gtgtgttaaa      2880
ttatggaccc tggcctgggt cttttccagg ccctataggc aggccagagc cacagcatgt      2940
aagccacggg gcactcccgt ggttcctgga ctctggcccc tggcatacag ggcttccaat      3000
ggaacaggag acagtggtga cagcggccgc aggaacccct agtgatggag ttggccactc      3060
cctctctgcg cgctcgctcg ctcactgagg ccgggcgacc aaaggtcgcc cgacgcccgg      3120
gctttgcccg ggcggcctca gtgagcgagc gagcgcgcag ctgcctgcag gggcgcctga      3180
tgcggtattt tctccttacg catctgtgcg gtatttcaca ccgcatacgt caaagcaacc      3240
atagtacgcg ccctgtagcg gcgcattaag cgcggcgggt gtggtggtta cgcgcagcgt      3300
gaccgctaca cttgccagcg ccctagcgcc cgctcctttc gctttcttcc cttcctttct      3360
cgccacgttc gccggctttc cccgtcaagc tctaaatcgg gggctccctt tagggttccg      3420
atttagtgct ttacggcacc tcgaccccaa aaaacttgat ttgggtgatg gttcacgtag      3480
tgggccatcg ccctgataga cggttttttcg ccctttgacg ttggagtcca cgttctttaa     3540
tagtggactc ttgttccaaa ctggaacaac actcaaccct atctcgggct attctttttga     3600 ttttataaggg attttgccga tttcggccta ttggttaaaa aatgagctga tttaacaaaa     3660
atttaacgcg aattttaaca aaatattaac gtttacaatt ttatggtgca ctctcagtac      3720
aatctgctct gatgccgcat agttaagcca gccccgacac ccgccaacac ccgctgacgc      3780
gccctgacgg gcttgtctgc tcccggcatc cgcttacaga caagctgtga ccgtctccgg      3840
gagctgcatg tgtcagaggt tttcaccgtc atcaccgaaa cgcgcgagac gaaagggcct      3900
cgtgatacgc ctattttat aggttaatgt catgataata atggtttctt agacaaacct       3960
agatattgat agtctgatcg gtcaacgtat aatcgagtcc tagcttttgc aaacatctat      4020
caagagacag gatcagcagg aggctttcgc atgattgaac aagatggatt gcacgcaggt      4080
tctccggcgg cttgggtgga gaggctattc ggctatgact gggcacaaca gacaatcggc      4140
tgctctgatg ccgccgtgtt ccggctgtca gcgcagggggc gtccggttct ttttgtcaag     4200
accgacctgt ccggtgccct gaatgaactg caagacgagg cagcgcggct atcgtggctg      4260
gcgacgacgg gcgttccttg cgcggctgtg ctcgacgttg tcactgaagc gggaagggac      4320
tggctgctat tgggcgaagt gccggggcag gatctcctgt catctcacct tgctcctgcc      4380
gagaaagtat ccatcatggc tgatgcaatg cggcggctgc atacgcttga tccggctacc      4440
tgcccattcg accaccaagc gaaacatcgc atcgagcgag cacgtactcg gatggaagcc      4500
ggtcttgtcg atcaggatga tctggacgaa gagcatcagg ggctcgcgcc agccgaactg      4560
ttcgccaggc tcaaggcgtc tatgcccgac ggcgaggatc tcgtcgtgac ccacggcgat      4620
gcctgcttgc cgaatatcat ggtggaaaat ggccgctttt ctggattcat cgactgtggc      4680
```

-continued

```
cgtctgggtg tggcggaccg ctatcaggac atagcgttgg ctacccgtga tattgctgaa    4740
gagcttggcg gcgaatgggc tgaccgcttc cttgtgcttt acggtatcgc cgcgcccgat    4800
tcgcagcgca tcgccttcta tcgccttctt gacgagttct tctgaccgat tctaggtgca    4860
ttggcgcaga aaaaaatgcc tgatgcgacg ctgcgcgtct tatactccca catatgccag    4920
attcagcaac ggatacggct tccccaactt gcccacttcc atacgtgtcc tccttaccag    4980
aaatttatcc ttaacgatcg gacggggagt caggcaacta tggatgaacg aaatagacag    5040
atcgctgaga taggtgcctc actgattaag cattggtaac tgtcagacca agtttactca    5100
tatatacttt agattgattt aaaacttcat ttttaattta aaaggatcta ggtgaagatc    5160 cttttttgata atctcatgac caaaatccct taacgtgagt tttcgttcca ctgagcgtca    5220 gacccccgtag aaaagatcaa aggatcttct tgagatcctt ttttttctgcg cgtaatctgc    5280 tgcttgcaaa caaaaaaacc accgctacca gcggtggttt gtttgccgga tcaagagcta    5340
ccaactcttt ttccgaaggt aactggcttc agcagagcgc agataccaaa tactgttctt    5400
ctagtgtagc cgtagttagg ccaccacttc aagaactctg tagcaccgcc tacatacctc    5460
gctctgctaa tcctgttacc agtggctgct gccagtggcg ataagtcgtg tcttaccggg    5520
ttggactcaa gacgatagtt accggataag cgcagcggg cgggctgaac ggggggttcg    5580
tgcacacagc ccagcttgga gcgaacgacc tacaccgaac tgagatacct acagcgtgag    5640
ctatgagaaa gcgccacgct tcccgaaggg agaaaggcgg acaggtatcc ggtaagcggc    5700
agggtcggaa caggagagcg cacgagggag cttccagggg gaaacgcctg gtatctttat    5760
agtcctgtcg ggtttcgcca cctctgactt gagcgtcgat ttttgtgatg ctcgtcaggg    5820
gggcggagcc tatggaaaaa cgccagcaac gcggcctttt tacggttcct ggccttttgc    5880
tggccttttg ctcacatgt                                                  5899
```

<210> SEQ ID NO 25
<211> LENGTH: 5875
<212> TYPE: DNA
<213> ORGANISM: Artificial Sequence
<220> FEATURE:
<223> OTHER INFORMATION: coRPK AAV used for pre-clinical studies

<400> SEQUENCE: 25

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccgcca gagtggtgaa ggcactctgc atttcttggt tgagacagag    180
aaaaaaagtg gtcagaactg ggtaaccctc cccccaccat attatcacag tgatccctttt    240 tgtctttctt caggctccag ccccacccta cagcccctgc tccctggatt cactagagct    300
aacttcagta aagtacaaag aaaatggggc catatgactg gccaaaaaaa aaatatctat    360
tcacgtggat gaccagatag tatgaatgga ttgaaaattt atcaggaaaa aaggatgaga    420
ggaaatgcca ggagatgagg gcagagagca ggccgttctg ggggagggat tctgtgggga    480
cagggtggcc tactgggtgt gcccctttc tcttctctgt ctcccttaga taagaccagc    540
agttttgtca tcctctccct ctcttccatg gtcccgcagc cccaggccca cactgaaagc    600
atgagcatcc aggaaaatat cagctctctg cagctgcggt cctgggtgtc caagagccag    660
agagacctgg ccaagagcat cctgatcgga gccctggcg gaccagccgg atacctgaga    720
agggctagcg tggcccagct gacccaggaa ctgggcaccg cctttttcca gcagcagcag    780
ctgccagccg ccatggccga cacctttctg gaacacctgt gcctgctgga catcgactct    840
```

-continued

```
gagcccgtgg ccgccagaag caccagcatc attgccacca tcggccctgc cagcagaagc      900
gtggagcggc tgaaagagat gatcaaggcc ggcatgaata tcgcccggct gaacttctcc      960
cacggcagcc acgagtacca cgcagagagc attgccaacg tccgggaggc cgtggagagc     1020
tttgccggca gcccctgag ctacagaccc gtggccattg ccctggacac caagggcccc     1080
gagatcagaa caggaattct gcagggaggg cctgagagcg aggtggagct ggtgaagggc     1140
agccaagtgc tggtgaccgt ggaccccgcc ttcagaacca gaggcaacgc caacacagtg     1200
tgggtggact accccaacat cgtgcgggtg gtgcctgtgg gcggcagaat ctacatcgac     1260
gacggcctga tcagcctggt ggtgcagaag atcggacctg agggcctggt gacccaggtc     1320
gagaatggcg gcgtgctggg cagcagaaag ggcgtgaatc tgccaggcgc ccaggtggac     1380
ctgcctggcc tgtctgagca ggacgtgaga gacctgagat ttggcgtgga gcacggcgtg     1440
gacatcgtgt cgccagctt cgtgcggaag gcctctgatg tggccgccgt gagagccgct     1500
ctgggccctg aaggccacgg catcaagatc atcagcaaga tcgagaacca cgagggcgtg     1560
aagcggttcg acgagatcct ggaagtgtcc gacggcatca tggtggccag aggcgacctg     1620
ggcatcgaga tccccgccga gaaggtgttc ctggcccaga aaatgatgat cggacggtgc     1680
aacctggccg gcaaacctgt ggtgtgcgcc acccagatgc tggaaagcat gatcaccaag     1740
cccagaccca ccagagccga gacaagcgac gtggccaacg ccgtgctgga tggcgctgac     1800
tgcatcatgc tgtccggcga gacagccaag ggcaacttcc ccgtggaggc cgtgaagatg     1860
cagcacgcca ttgccagaga gccgaggcc gccgtgtacc accggcagct gttcgaggaa     1920
ctgcggagag ccgcccctct gagcagagat cccaccgaag tgaccgccat cggagccgtg     1980
gaagccgcct tcaagtgctg cgccgctgca atcatcgtgc tgaccaccac aggcagaagc     2040
gcccagctgc tgtccagata cagacccaga gccgccgtga tcgccgtgac aagatccgcc     2100
caggccgcta gacaggtcca cctgtgcaga ggcgtgttcc ccctgctgta ccgggagcct     2160
cccgaggcca tctgggccga cgacgtggac agacggggtgc agttcggcat cgagagcggc     2220
aagctgcggg gcttcctgag agtgggcgac ctggtgatcg tggtgacagg ctggcggcct     2280
ggcagcggct acaccaacat catgagggtg ctgtccatca gctgaacgcg tgagttacaa     2340
ataaagcact gtgccttcta gttgccagcc atctgttgtt tgcccctccc ccgtgccttc     2400
cttgaccctg gaaggtgcca ctcccactgt cctttcctaa taaaatgagg aaattgcatc     2460
gcattgtctg agtaggtgtc attctattct ggggggtggg gtggggcagg acagcaaggg     2520
ggaggattgg gaagacaata gcaggcatgc tggggatgcg gtgggctcta tgggtcccgc     2580
agccccaggc ccacactgaa agcatgtcga tccaggagaa catatcatcc ctgcagcttc     2640
ggtcatgggt ctctaagtcc caaagagact tagcaaagtc catcctgatt ggggctccag     2700
gaggtaagaa ggggagacag aagccatgga acataggagg aaaatgaggg tgaaaactag     2760
gagccagggt ggagggcata aatgatccac atcagccact ggctaggtgg gttttggaga     2820
ggaacgtacg ttcttcagag cctcccgtgt gttaaattat ggaccctggc ctgggtcttt     2880
tccaggccct ataggcaggc cagagccaca gcatgtaagc cacggggcac tcccgtggtt     2940
cctggactct ggccctggc atacagggct tccaatggaa caggagacag tggtgacagc     3000
ggccgcagga accctagtg atggagttgg ccactccctc tctgcgcgct cgctcgctca     3060
ctgaggccgg gcgaccaaag gtcgcccgac gcccgggctt gcccgggcg cctcagtga     3120 gcgagcgagc gcgcagctgc ctgcaggggc gcctgatgcg gtattttctc cttacgcatc     3180
```

-continued

```
tgtgcggtat ttcacaccgc atacgtcaaa gcaaccatag tacgcgccct gtagcggcgc   3240
attaagcgcg gcgggtgtgg tggttacgcg cagcgtgacc gctacacttg ccagcgccct   3300
agcgcccgct cctttcgctt tcttcccttc ctttctcgcc acgttcgccg gctttccccg   3360
tcaagctcta aatcgggggc tccctttagg gttccgattt agtgctttac ggcacctcga   3420
ccccaaaaaa cttgatttgg gtgatggttc acgtagtggg ccatcgccct gatagacggt   3480
ttttcgccct ttgacgttgg agtccacgtt ctttaatagt ggactcttgt tccaaactgg   3540
aacaacactc aaccctatct cgggctattc ttttgattta taagggattt tgccgatttc   3600
ggcctattgg ttaaaaaatg agctgattta acaaaaattt aacgcgaatt ttaacaaaat   3660
attaacgttt acaattttat ggtgcactct cagtacaatc tgctctgatg ccgcatagtt   3720
aagccagccc cgacacccgc caacacccgc tgacgcgccc tgacgggctt gtctgctccc   3780
ggcatccgct tacagacaag ctgtgaccgt ctccgggagc tgcatgtgtc agaggttttc   3840
accgtcatca ccgaaacgcg cgagacgaaa gggcctcgtg atacgcctat ttttataggt   3900
taatgtcatg ataataatgg tttcttagac aaacctagat attgatagtc tgatcggtca   3960
acgtataatc gagtcctagc ttttgcaaac atctatcaag agacaggatc agcaggaggc   4020
tttcgcatga ttgaacaaga tggattgcac gcaggttctc cggccggcttg ggtggagagg   4080 ctattcggct atgactgggc acaacagaca atcggctgct ctgatgccgc cgtgttccgg   4140
ctgtcagcgc aggggcgtcc ggttcttttt gtcaagaccg acctgtccgg tgccctgaat   4200
gaactgcaag acgaggcagc gcggctatcg tggctggcga cgacgggcgt tccttgcgcg   4260
gctgtgctcg acgttgtcac tgaagcggga aagggactggc tgctattggg cgaagtgccg   4320
gggcaggatc tcctgtcatc tcaccttgct cctgccgaga aagtatccat catggctgat   4380
gcaatgcggc ggctgcatac gcttgatccg gctacctgcc cattcgacca ccaagcgaaa   4440
catcgcatcg agcgagcacg tactcggatg gaagccggtc ttgtcgatca ggatgatctg   4500
gacgaagagc atcaggggct cgcgccagcc gaactgttcg ccaggctcaa ggcgtctatg   4560
cccgacggcg aggatctcgt cgtgacccac ggcgatgcct gcttgccgaa tatcatggtg   4620
gaaaatggcc gcttttctgg attcatcgac tgtggccgtc tgggtgtggc ggaccgctat   4680
caggacatag cgttggctac ccgtgatatt gctgaagagc ttggcggcga atgggctgac   4740
cgcttccttg tgctttacgg tatcgccgcg cccgattcgc agcgcatcgc cttctatcgc   4800
cttcttgacg agttcttctg accgattcta ggtgcattgg cgcagaaaaa aatgcctgat   4860
gcgacgctgc gcgtcttata ctcccacata tgccagattc agcaacggat acggcttccc   4920
caacttgccc acttccatac gtgtcctcct taccagaaat ttatccttaa cgatcggacg   4980
gggagtcagg caactatgga tgaacgaaat agacagatcg ctgagatagg tgcctcactg   5040
attaagcatt ggtaactgtc agaccaagtt tactcatata tactttagat tgatttaaaa   5100
cttcattttt aatttaaaag gatctaggtg aagatccttt ttgataatct catgaccaaa   5160
atcccttaac gtgagttttc gttccactga gcgtcagacc ccgtagaaaa gatcaaagga   5220
tcttcttgag atcctttttt tctgcgcgta atctgctgct tgcaaacaaa aaaaccaccg   5280
ctaccagcgg tggtttgttt gccggatcaa gagctaccaa ctctttttcc gaaggtaact   5340
ggcttcagca gagcgcagat accaaatact gttcttctag tgtagccgta gttaggccac   5400
cacttcaaga actctgtagc accgcctaca tacctcgctc tgctaatcct gttaccagtg   5460
gctgctgcca gtggcgataa gtcgtgtctt accgggttgg actcaagacg atagttaccg   5520
gataaggcgc agcggtcggg ctgaacgggg ggttcgtgca cacagcccag cttggagcga   5580
```

```
acgacctaca ccgaactgag atacctacag cgtgagctat gagaaagcgc cacgcttccc       5640
gaagggagaa aggcggacag gtatccggta agcggcaggg tcggaacagg agagcgcacg       5700
agggagcttc caggggaaa cgcctggtat ctttatagtc ctgtcgggtt tcgccacctc        5760
tgacttgagc gtcgattttt gtgatgctcg tcagggggc ggagcctatg gaaaaacgcc        5820
agcaacgcgg cctttttacg gttcctggcc ttttgctggc cttttgctca catgt           5875
```

<210> SEQ ID NO 26
<211> LENGTH: 5899
<212> TYPE: DNA
<213> ORGANISM: Artificial Sequence
<220> FEATURE:
<223> OTHER INFORMATION: coRPK AAV used for pre-clinical studies

<400> SEQUENCE: 26

```
cctgcaggca gctgcgcgct cgctcgctca ctgaggccgc ccgggcgtcg ggcgaccttt          60
ggtcgcccgg cctcagtgag cgagcgagcg cgcagagagg gagtggccaa ctccatcact         120
aggggttcct gcggccgctg tcaccactgt ctcctgttcc attggaagcc ctgtatgcca         180
ggggccagag tccaggaacc acgggagtgc cccgtggctt acatgctgtg gctctggcct         240
gcctataggg cctggaaaag acccaggcca gggtccataa tttaacacac gggaggctct         300
gaagaacgta cgttcctctc caaaacccac ctagccagtg gctgatgtgg atcatttatg         360
ccctccaccc tggctcctag ttttcaccct cattttcctc ctatgttcca tggcttctgt         420
ctccccttct tacctcctgg agccccaatc aggatggact ttgctaagtc tctttgggac         480
ttagagaccc atgaccgaag ctgcagggat gatatgttct cctggatcga catgctttca        540
gtgtgggcct ggggctgcgg gacccataga gcccaccgca tccccagcat gcctgctatt        600
gtcttcccaa tcctccccct tgctgtcctg ccccacccca cccccagaa tagaatgaca         660 cctactcaga caatgcgatg caatttcctc attttattag gaaaggacag tgggagtggc        720
accttccagg gtcaaggaag gcacggggga ggggcaaaca acagatggct ggcaactaga        780
aggcacagtg ctttatttgt aactcacgcg ttcatttatc gtcatcgtct ttgtagtcgc        840
tgatggacag caccctcatg atgttggtgt agccgctgcc aggccgccag cctgtcacca        900
cgatcaccag gtcgcccact ctcaggaagc cccgcagctt gccgctctcg atgccgaact        960
gcacccgtct gtccacgtcg tcggcccaga tggcctcggg aggctcccgg tacagcaggg       1020
ggaacacgcc tctgcacagg tggacctgtc tagcggcctg ggcggatctt gtcacggcga       1080
tcacggcggc tctgggtctg tatctggaca gcagctgggc gcttctgcct gtggtggtca       1140
gcacgatgat tgcagcggcg cagcacttga aggcggcttc cacggctccg atggcggtca       1200
cttcggtggg atctctgctc agaggggcgg ctctccgcag ttcctcgaac agctgccggt       1260
ggtacacggc ggcctcggct tctctggcaa tggcgtgctg catcttcacg gcctccacgg       1320
ggaagttgcc cttggctgtc tcgcggaca gcatgatgca gtcagcgcca tccagcacgg        1380
cgttggccac gtcgcttgtc tcggctctgg tgggtctggg cttggtgatc atgctttcca       1440
gcatctgggt ggcgcacacc acaggtttgc cggccaggtt gcaccgtccg atcatcattt       1500
tctgggccag gaacaccttc tcggcgggga tctcgatgcc caggtcgcct ctggccacca       1560
tgatgccgtc ggacacttcc aggatctcgt cgaaccgctt cacgccctcg tggttctcga       1620
tcttgctgat gatcttgatg ccgtggcctt cagggcccag agcggctctc acggcggcca      1680
catcagaggc cttccgcacg aagctggcga acacgatgtc cacgccgtgc tccacgccaa       1740
```

-continued

```
atctcaggtc tctcacgtcc tgctcagaca ggccaggcag gtccacctgg gcgcctggca    1800
gattcacgcc ctttctgctg cccagcacgc cgccattctc gacctgggtc accaggccct    1860
caggtccgat cttctgcacc accaggctga tcaggccgtc gtcgatgtag attctgccgc    1920
ccacaggcac cacccgcacg atgttggggt agtccaccca cactgtgttg gcgttgcctc    1980
tggttctgaa ggcggggtcc acggtcacca gcacttggct gcccttcacc agctccacct    2040
cgctctcagg ccctccctgc agaattcctg ttctgatctc ggggcccttg gtgtccaggg    2100
caatggccac gggtctgtag ctcagggggc tgccggcaaa gctctccacg gcctcccgga    2160
cgttggcaat gctctctgcg tggtactcgt ggctgccgtg ggagaagttc agccgggcga    2220
tattcatgcc ggccttgatc atctctttca gccgctccac gcttctgctg gcagggccga    2280
tggtggcaat gatgctggtg cttctggcgg ccacgggctc agagtcgatg tccagcaggc    2340
acaggtgttc cagaaaggtg tcggccatgg cggctggcag ctgctgctgc tggaaaaagg    2400
cggtgcccag ttcctgggtc agctgggcca cgctagccct tctcaggtat ccggctggtc    2460
cgccaggggc tccgatcagg atgctcttgg ccaggtctct ctggctcttg gacacccagg    2520
accgcagctg cagagagctg atattttcct ggatgctcat gctttcagtg tgggcctggg    2580
gctgcgggac catggaagag agggagagga tgacaaaact gctggtctta tctaagggag    2640
acagagaaga gaaagggggc acacccagta ggccaccctg tccccacaga atccctcccc    2700
cagaacggcc tgctctctgc cctcatctcc tggcatttcc tctcatcctt ttttcctgat    2760
aaattttcaa tccattcata ctatctggtc atccacgtga atagatattt tttttttggc    2820
cagtcatatg gccccatttt ctttgtactt tactgaagtt agctctagtg aatccaggga    2880
gcaggggctg tagggtgggg ctggagcctg aagaaagaca aaagggatca ctgtgataat    2940
atggtggggg gagggttacc cagttctgac cacttttttt ctctgtctca accaagaaat    3000
gcagagtgcc ttcaccactc tggcggccgc aggaaccct  agtgatggag ttggccactc    3060
cctctctgcg cgctcgctcg ctcactgagg ccgggcgacc aaaggtcgcc cgacgcccgg    3120
gctttgcccg ggcggcctca gtgagcgagc gagcgcgcag ctgcctgcag gggcgcctga    3180
tgcggtattt tctccttacg catctgtgcg gtatttcaca ccgcatacgt caaagcaacc    3240
atagtacgcg ccctgtagcg gcgcattaag cgcggcgggt gtggtggtta cgcgcagcgt    3300
gaccgctaca cttgccagcg ccctagcgcc cgctcctttc gctttcttcc cttcctttct    3360
cgccacgttc gccggctttc cccgtcaagc tctaaatcgg gggctccctt tagggttccg    3420
atttagtgct ttacggcacc tcgaccccaa aaaacttgat ttgggtgatg gttcacgtag    3480
tgggccatcg ccctgataga cggttttttcg ccctttgacg ttggagtcca cgttctttaa    3540
tagtggactc ttgttccaaa ctggaacaac actcaaccct atctcgggct attcttttga    3600
tttataaggg attttgccga tttcggccta ttggttaaaa aatgagctga tttaacaaaa    3660
atttaacgcg aattttaaca aaatattaac gtttacaatt ttatggtgca ctctcagtac    3720
aatctgctct gatgccgcat agttaagcca gccccgacac ccgccaacac ccgctgacgc    3780
gccctgacgg gcttgtctgc tcccggcatc cgcttacaga caagctgtga ccgtctccgg    3840
gagctgcatg tgtcagaggt tttcaccgtc atcaccgaaa cgcgcgagac gaaagggcct    3900
cgtgatacgc ctattttttat aggttaatgt catgataata atggtttctt agacaaacct    3960
agatattgat agtctgatcg gtcaacgtat aatcgagtcc tagcttttgc aaacatctat    4020
caagagacag gatcagcagg aggctttcgc atgattgaac aagatggatt gcacgcaggt    4080 tctccggccgg cttgggtgga gaggctattc ggctatgact gggcacaaca gacaatcggc    4140
```

-continued

```
tgctctgatg ccgccgtgtt ccggctgtca gcgcaggggc gtccggttct ttttgtcaag      4200
accgacctgt ccggtgccct gaatgaactg caagacgagg cagcgcggct atcgtggctg      4260
gcgacgacgg gcgttccttg cgcggctgtg ctcgacgttg tcactgaagc gggaagggac      4320
tggctgctat tgggcgaagt gccggggcag gatctcctgt catctcacct tgctcctgcc      4380
gagaaagtat ccatcatggc tgatgcaatg cggcggctgc atacgcttga tccggctacc      4440
tgcccattcg accaccaagc gaaacatcgc atcgagcgag cacgtactcg gatggaagcc      4500
ggtcttgtcg atcaggatga tctggacgaa gagcatcagg ggctcgcgcc agccgaactg      4560
ttcgccaggc tcaaggcgtc tatgcccgac ggcgaggatc tcgtcgtgac ccacggcgat      4620
gcctgcttgc cgaatatcat ggtggaaaat ggccgctttt ctggattcat cgactgtggc      4680
cgtctgggtg tggcggaccg ctatcaggac atagcgttgg ctacccgtga tattgctgaa      4740
gagcttggcg gcgaatgggc tgaccgcttc cttgtgcttt acggtatcgc cgcgcccgat      4800
tcgcagcgca tcgccttcta tcgccttctt gacgagttct tctgaccgat tctaggtgca      4860
ttggcgcaga aaaaaatgcc tgatgcgacg ctgcgcgtct tatactccca catatgccag      4920
attcagcaac ggatacggct tccccaactt gcccacttcc atacgtgtcc tccttaccag      4980
aaatttatcc ttaacgatcg gacggggagt caggcaacta tggatgaacg aaatagacag      5040
atcgctgaga taggtgcctc actgattaag cattggtaac tgtcagacca gtttactca      5100 tatatacttt agattgattt aaaacttcat ttttaattta aaaggatcta ggtgaagatc      5160
ctttttgata atctcatgac caaaatccct taacgtgagt tttcgttcca ctgagcgtca      5220
gaccccgtag aaaagatcaa aggatcttct tgagatcctt ttttctgcg cgtaatctgc      5280 tgcttgcaaa caaaaaaacc accgctacca gcggtggttt gtttgccgga tcaagagcta      5340
ccaactcttt ttccgaaggt aactggcttc agcagagcgc agataccaaa tactgttctt      5400
ctagtgtagc cgtagttagg ccaccacttc aagaactctg tagcaccgcc tacatacctc      5460
gctctgctaa tcctgttacc agtggctgct gccagtggcg ataagtcgtg tcttaccggg      5520
ttggactcaa gacgatagtt accggataag gcgcagcggt cgggctgaac ggggggttcg      5580
tgcacacagc ccagcttgga gcgaacgacc tacaccgaac tgagatacct acagcgtgag      5640
ctatgagaaa gcgccacgct tcccgaaggg agaaaggcgg acaggtatcc ggtaagcggc      5700
agggtcggaa caggagagcg cacgagggag cttccagggg gaaacgcctg gtatctttat      5760
agtcctgtcg ggtttcgcca cctctgactt gagcgtcgat ttttgtgatg ctcgtcaggg      5820
gggcggagcc tatggaaaaa cgccagcaac gcggcctttt tacggttcct ggccttttgc      5880
tggccttttg ctcacatgt                                                   5899
```

```
<210> SEQ ID NO 27
<211> LENGTH: 5875
<212> TYPE: DNA
<213> ORGANISM: Artificial Sequence
<220> FEATURE:
<223> OTHER INFORMATION: coRPK AAV for clinical use

<400> SEQUENCE: 27
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact       120
aggggttcct gcggccgctg tcaccactgt ctcctgttcc attggaagcc ctgtatgcca       180
ggggccagag tccaggaacc acgggagtgc ccgtggcctt acatgctgtg gctctggcct       240
```

-continued

```
gcctataggg cctggaaaag acccaggcca gggtccataa tttaacacac gggaggctct      300
gaagaacgta cgttcctctc caaaacccac ctagccagtg gctgatgtgg atcatttatg      360
ccctccaccc tggctcctag ttttcaccct cattttcctc ctatgttcca tggcttctgt      420 ctcccttct tacctcctgg agccccaatc aggatggact ttgctaagtc tctttgggac       480
ttagagaccc atgaccgaag ctgcagggat gatatgttct cctggatcga catgctttca      540
gtgtgggcct ggggctgcgg gacccataga gcccaccgca tccccagcat gcctgctatt      600
gtcttcccaa tcctcccct tgctgtcctg ccccaccca cccccagaa tagaatgaca         660 cctactcaga caatgcgatg caatttcctc attttattag aaaggacag tgggagtggc       720 accttccagg gtcaaggaag gcacggggga ggggcaaaca acagatggct ggcaactaga      780
aggcacagtg ctttatttgt aactcacgcg ttcagctgat ggacagcacc ctcatgatgt      840
tggtgtagcc gctgccaggc cgccagcctg tcaccacgat caccaggtcg cccactctca      900
ggaagccccg cagcttgccg ctctcgatgc cgaactgcac ccgtctgtcc acgtcgtcgg      960
cccagatggc ctcgggaggc tcccggtaca gcaggggaa cacgcctctg cacaggtgga     1020
cctgtctagc ggcctgggcg gatcttgtca cggcgatcac ggcggctctg ggtctgtatc     1080
tggacagcag ctgggcgctt ctgcctgtgg tggtcagcac gatgattgca gcggcgcagc     1140
acttgaaggc ggcttccacg gctccgatgg cggtcacttc ggtgggatct ctgctcagag     1200
gggcggctct ccgcagttcc tcgaacagct gccggtggta cacggcggcc tcggcttctc     1260
tggcaatggc gtgctgcatc ttcacggcct ccacggggaa gttgcccttg gctgtctcgc     1320
cggacagcat gatgcagtca gcgccatcca gcacggcgtt ggccacgtcg cttgtctcgg     1380
ctctggtggg tctgggcttg gtgatcatgc tttccagcat ctgggtggcg cacaccacag     1440
gtttgccggc caggttgcac cgtccgatca tcattttctg ggccaggaac accttctcgg     1500
cggggatctc gatgcccagg tcgcctctgg ccaccatgat gccgtcggac acttccagga     1560
tctcgtcgaa ccgcttcacg ccctcgtggt tctcgatctt gctgatgatc ttgatgccgt     1620
ggccttcagg gcccagagcg gctctcacgg cggccacatc agaggccttc cgcacgaagc     1680
tggcgaacac gatgtccacg ccgtgctcca cgccaaatct caggtctctc acgtcctgct     1740
cagacaggcc aggcaggtcc acctgggcgc ctggcagatt cacgcccttt ctgctgccca     1800
gcacgccgcc attctcgacc tgggtcacca ggccctcagg tccgatcttc tgcaccacca     1860
ggctgatcag gccgtcgtcg atgtagattc tgccgcccac aggcaccacc cgcacgatgt     1920
tggggtagtc cacccacact gtgttggcgt tgcctctggt tctgaaggcg gggtccacgg     1980
tcaccagcac ttggctgccc ttcaccagct ccacctcgct ctcaggccct ccctgcagaa     2040
ttcctgttct gatctcgggg cccttggtgt ccagggcaat ggccacgggt ctgtagctca     2100
gggggctgcc ggcaaagctc tccacggcct cccggacgtt ggcaatgctc tctgcgtggt     2160
actcgtggct gccgtgggag aagttcagcc gggcgatatt catgccggcc ttgatcatct     2220
ctttcagccg ctccacgctt ctgctggcag ggccgatggt ggcaatgatg ctggtgcttc     2280
tggcggccac gggctcagag tcgatgtcca gcaggcacag gtgttccaga aaggtgtcgg     2340
ccatggcggc tggcagctgc tgctgctgga aaaaggcggt gcccagttcc tgggtcagct     2400
gggccacgct agcccttctc aggtatccgg ctggtccgcc aggggctccg atcaggatgc     2460
tcttggccag gtctctctgg ctcttggaca cccaggaccg cagctgcaga gagctgatat     2520
tttcctggat gctcatgctt tcagtgtggg cctggggctg cggggaccatg gaagagaggg    2580 agaggatgac aaaactgctg gtcttatcta agggagacag agaagagaaa aggggcacac     2640
```

-continued

```
ccagtaggcc accctgtccc cacagaatcc ctcccccaga acggcctgct ctctgccctc    2700
atctcctggc atttcctctc atcctttttt cctgataaat tttcaatcca ttcatactat    2760
ctggtcatcc acgtgaatag atattttttt tttggccagt catatggccc cattttcttt    2820
gtactttact gaagttagct ctagtgaatc cagggagcag gggctgtagg gtggggctgg    2880
agcctgaaga aagacaaaag ggatcactgt gataatatgg tggggggagg gttacccagt    2940
tctgaccact ttttttctct gtctcaacca agaaatgcag agtgccttca ccactctggc    3000
ggccgcagga acccctagtg atggagttgg ccactccctc tctgcgcgct cgctcgctca    3060
ctgaggccgg gcgaccaaag gtcgcccgac gcccgggctt tgcccgggcg gcctcagtga    3120
gcgagcgagc gcgcagctgc ctgcaggggc gcctgatgcg gtattttctc cttacgcatc    3180
tgtgcggtat ttcacaccgc atacgtcaaa gcaaccatag tacgcgccct gtagcggcgc    3240
attaagcgcg gcgggtgtgg tggttacgcg cagcgtgacc gctacacttg ccagcgccct    3300
agcgcccgct cctttcgctt tcttcccttc ctttctcgcc acgttcgccg gctttccccg    3360
tcaagctcta aatcggggggc tccctttagg gttccgattt agtgctttac ggcacctcga    3420
ccccaaaaaa cttgatttgg gtgatggttc acgtagtggg ccatcgccct gatagacggt    3480
ttttcgccct ttgacgttgg agtccacgtt ctttaatagt ggactcttgt tccaaactgg    3540
aacaacactc aaccctatct cgggctattc ttttgattta taagggattt tgccgatttc    3600
ggcctattgg ttaaaaaatg agctgattta acaaaaattt aacgcgaatt ttaacaaaat    3660
attaacgttt acaattttat ggtgcactct cagtacaatc tgctctgatg ccgcatagtt    3720
aagccagccc cgacacccgc caacacccgc tgacgcgccc tgacgggctt gtctgctccc    3780
ggcatccgct tacagacaag ctgtgaccgt ctccgggagc tgcatgtgtc agaggttttc    3840
accgtcatca ccgaaacgcg cgagacgaaa gggcctcgtg atacgcctat ttttataggt    3900
taatgtcatg ataataatgg tttcttagac aaacctagat attgatagtc tgatcggtca    3960
acgtataatc gagtcctagc ttttgcaaac atctatcaag agacaggatc agcaggaggc    4020
tttcgcatga ttgaacaaga tggattgcac gcaggttctc cggccggcttg ggtggagagg    4080 ctattcggct atgactgggc acaacagaca atcggctgct ctgatgccgc cgtgttccgg    4140
ctgtcagcgc aggggcgtcc ggttcttttt gtcaagaccg acctgtccgg tgccctgaat    4200
gaactgcaag acgaggcagc gcggctatcg tggctggcga cgacgggcgt tccttgcgcg    4260
gctgtgctcg acgttgtcac tgaagcggga aagggactggc tgctattggg cgaagtgccg    4320
gggcaggatc tcctgtcatc tcaccttgct cctgccgaga aagtatccat catggctgat    4380
gcaatgcggc ggctgcatac gcttgatccg gctacctgcc cattcgacca ccaagcgaaa    4440
catcgcatcg agcgagcacg tactcggatg gaagccggtc ttgtcgatca ggatgatctg    4500
gacgaagagc atcaggggct cgcgccagcc gaactgttcg ccaggctcaa ggcgtctatg    4560
cccgacggcg aggatctcgt cgtgacccac ggcgatgcct gcttgccgaa tatcatggtg    4620
gaaaatggcc gcttttctgg attcatcgac tgtggccgtc tgggtgtggc ggaccgctat    4680
caggacatag cgttggctac ccgtgatatt gctgaagagc ttggcggcga atgggctgac    4740
cgcttccttg tgctttacgg tatcgccgcg cccgattcgc agcgcatcgc cttctatcgc    4800
cttcttgacg agttcttctg accgattcta ggtgcattgg cgcagaaaaa aatgcctgat    4860
gcgacgctgc gcgtcttata ctcccacata tgccagattc agcaacggat acggcttccc    4920
caacttgccc acttccatac gtgtcctcct taccagaaat ttatccttaa cgatcggacg    4980
```

-continued

```
gggagtcagg caactatgga tgaacgaaat agacagatcg ctgagatagg tgcctcactg      5040
attaagcatt ggtaactgtc agaccaagtt tactcatata tactttagat tgatttaaaa      5100
cttcattttt aatttaaaag gatctaggtg aagatccttt ttgataatct catgaccaaa      5160
atcccttaac gtgagttttc gttccactga gcgtcagacc ccgtagaaaa gatcaaagga      5220
tcttcttgag atcctttttt tctgcgcgta atctgctgct tgcaaacaaa aaaaccaccg      5280
ctaccagcgg tggtttgttt gccggatcaa gagctaccaa ctcttttcc gaaggtaact       5340 ggcttcagca gagcgcagat accaaatact gttcttctag tgtagccgta gttaggccac      5400
cacttcaaga actctgtagc accgcctaca tacctcgctc tgctaatcct gttaccagtg      5460
gctgctgcca gtggcgataa gtcgtgtctt accgggttgg actcaagacg atagttaccg      5520
gataaggcgc agcggtcggg ctgaacgggg ggttcgtgca cacagcccag cttggagcga      5580
acgacctaca ccgaactgag atacctacag cgtgagctat gagaaagcgc cacgcttccc      5640
gaagggagaa aggcggacag gtatccggta agcggcaggg tcggaacagg agagcgcacg      5700
agggagcttc caggggggaaa cgcctggtat ctttatagtc ctgtcgggtt cgccacctc      5760 tgacttgagc gtcgattttt gtgatgctcg tcagggggc ggagcctatg gaaaaacgcc        5820
agcaacgcgg ccttttttacg gttcctggcc ttttgctggc cttttgctca catgt          5875
```

```
<210> SEQ ID NO 28
<211> LENGTH: 218
<212> TYPE: DNA
<213> ORGANISM: Homo sapiens
<220> FEATURE:
<221> NAME/KEY: misc_feature
<222> LOCATION: (1)..(218)
<223> OTHER INFORMATION: RPK CDS (Fig 1)

<400> SEQUENCE: 28
gttctggggg agggattctg tggggacagg gtggcctact gggtgtgccc cttttctctt         60
ctctgtctcc cttagataag accagcagtt ttgtcatcct ctccctctca ttccatggtc       120
ccgcagcccc aggcccacac tgaaagcatg tcgatccagg agaacatatc atccctgcag       180
cttcggtcat gggtctctaa gtcccaaaga gacttagc                              218
```

```
<210> SEQ ID NO 29
<211> LENGTH: 107
<212> TYPE: DNA
<213> ORGANISM: Artificial Sequence
<220> FEATURE:
<223> OTHER INFORMATION: PKLR locus (Fig 7)

<400> SEQUENCE: 29
tctgtctccc ttagataaga ccagcagttt tgtcatcctc tccctctcat tccatggtcc          60
cgcagcccca ggcccacact gaaagcatgt cgatccagga gaacata                     107
```

```
<210> SEQ ID NO 30
<211> LENGTH: 88
<212> TYPE: DNA
<213> ORGANISM: Artificial Sequence
<220> FEATURE:
<223> OTHER INFORMATION: Genomic region of the starting site of the RPK
      transcript variant (Fig 8, 9, 10, 11)

<400> SEQUENCE: 30
aagaccagca gttttgtcat cctctccctc tcattccatg gtcccgcagc cccaggccca          60
cactgaaagc atgtcgatcc aggagaac                                          88
```

-continued

Figure 12:
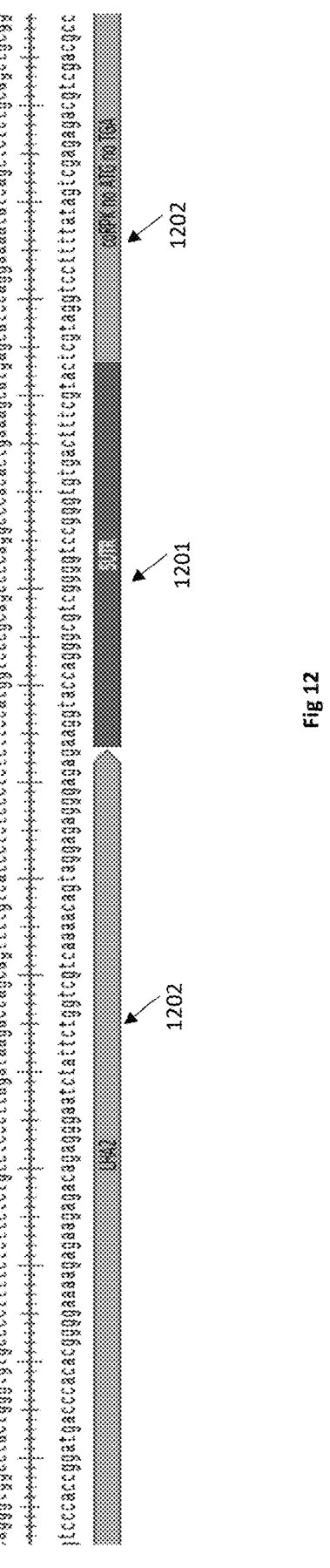
FIG. 12: Diagram showing 5'UTR position with respect to LHA and coRPK without start condon in coRPK-AAV vector. The sequence of part of 5'UTR, mentioned in FIG. 11, is cloned between the Left Homologous Arm and the cDNA of coRPK, to keep the endogenous regulation of the RPK transcript variant. The transcription start site is provided by the cloned 5'UTR. 1201, 5'UTR localization; 1202, LHA and coRPK sequences. SEQ ID NOS: 31, 43.

```
<210> SEQ ID NO 31
<211> LENGTH: 158
<212> TYPE: DNA
<213> ORGANISM: Artificial Sequence
<220> FEATURE:
<223> OTHER INFORMATION: 5UTR position with respect to LHA and coRPK
      without start condon in coRPK- AAV vector (Fig 12)

<400> SEQUENCE: 31
agggtggcct actgggtgtg ccccttttct cttctctgtc tcccttagat aagaccagca      60
gttttgtcat cctctccctc tcttccatgg tcccgcagcc ccaggcccac actgaaagca     120
tgagcatcca ggaaaatatc agctctctgc agctgcgg                             158

Figure 13:
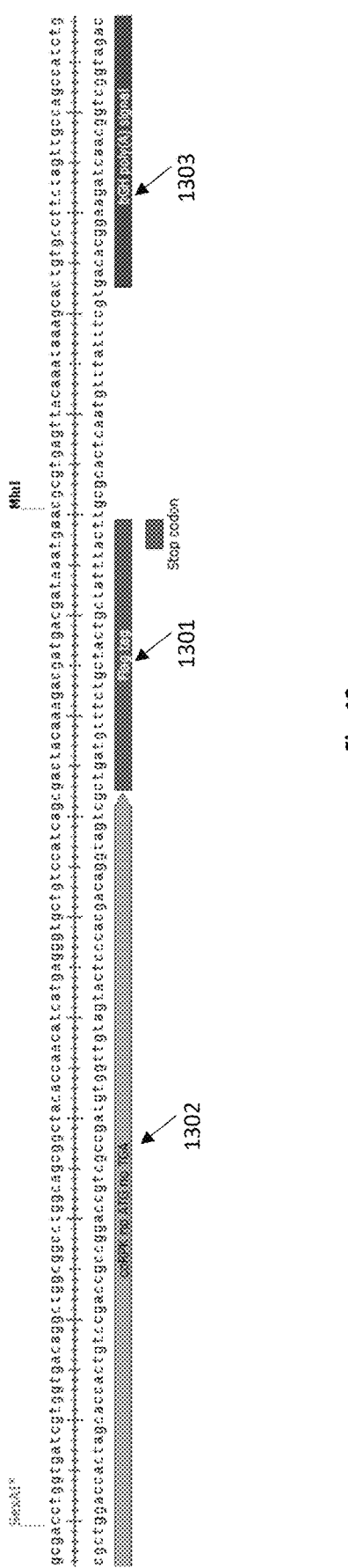
FIG. 13: Diagram showing FLAG-Tag position with respect to coRPK without STOP condon and bGH poly(A) signal in coRPK-AAV vector. A fusion protein between coRPK and FLAG-Tag is made after removing coRPK STOP codon and cloning FLAG-Tag sequence in the same open reading frame (ORF). Stop codon is provided by in the 3' FLAG Tag sequence. 1301, FLAG-Tag sequence; 1302, coRPK sequences; 1303, bGH polyadenylation signal. SEQ ID NOS: 32, 44.

<210> SEQ ID NO 32
<211> LENGTH: 154
<212> TYPE: DNA
<213> ORGANISM: Artificial Sequence
<220> FEATURE:
<223> OTHER INFORMATION: FLAG-Tag position with respect to coRPK without
      STOP condon and bGH poly(A) signal in coRPK-AAV vector (Fig 13)

<400> SEQUENCE: 32
gcgacctggt gatcgtggtg acaggctggc ggcctggcag cggctacacc aacatcatga      60
gggtgctgtc catcagcgac tacaaagacg atgacgataa atgaacgcgt gagttacaaa     120
taaagcactg tgccttctag ttgccagcca tctg                                 154

Figure 14:
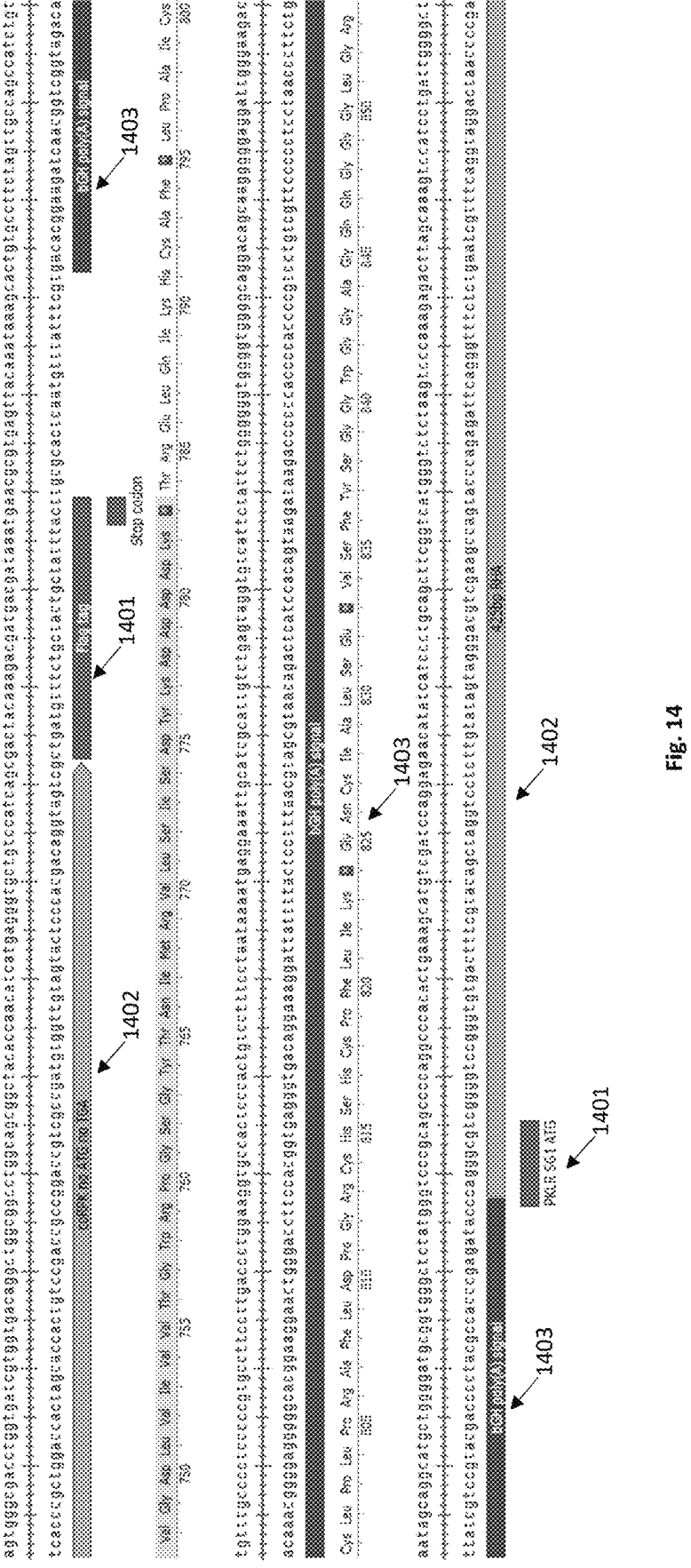
FIG. 14: Diagram showing bGH poly(A) signal with respect to coRPK-FLAG and RHA in coRPK-AAV vector. Upstream of coRPK-FLAG tag cDNA, bovine growth hormone polyadenylation (bGH poly(A)) signal is cloned to transcribe efficiently the therapeutic cassette. The right homologous arm (RHA) is cloned after this polyadenylation signal. 1401, FLAG-Tag and partial SG1 guide sequence, located in the RHA, sequences; 1402, coRPK and RHA sequences; 1403, bGH polyadenylation signal. SEQ ID NOS: 33, 36-40, 45.

<210> SEQ ID NO 33
<211> LENGTH: 480
<212> TYPE: DNA
<213> ORGANISM: Artificial Sequence
<220> FEATURE:
<223> OTHER INFORMATION: bGH poly(A) signal with respect to coRPK-FLAG
      and RHA in coRPK-AAV vector (Fig 14)

<400> SEQUENCE: 33
agtgggcgac ctggtgatcg tggtgacagg ctggcggcct ggcagcggct acaccaacat      60
catgagggtg ctgtccatca gcgactacaa agacgatgac gataaatgaa cgcgtgagtt     120
acaaataaag cactgtgcct tctagttgcc agccatctgt tgtttgcccc tccccgtgc      180 cttccttgac cctggaaggt gccactccca ctgtcctttc ctaataaaat gaggaaattg     240
catcgcattg tctgagtagg tgtcattcta ttctggggggg tggggtgggg caggacagca     300 aggggggagga ttgggaagac aatagcaggc atgctgggga tgcggtgggc tctatgggtc     360
ccgcagcccc aggcccacac tgaaagcatg tcgatccagg agaacatatc atccctgcag     420
cttcggtcat gggtctctaa gtcccaaaga gacttagcaa agtccatcct gattggggct     480

<210> SEQ ID NO 34
<211> LENGTH: 23
<212> TYPE: PRT
<213> ORGANISM: Artificial Sequence
<220> FEATURE:
<223> OTHER INFORMATION: Aminoacid seq. RPK (Fig 1)

<400> SEQUENCE: 34

Met Ser Ile Gln Glu Asn Ile Ser Ser Leu Gln Leu Arg Ser Trp Val
1               5                   10                  15

Ser Lys Ser Gln Arg Asp Leu
            20

<210> SEQ ID NO 35
```

```
<211> LENGTH: 6
<212> TYPE: PRT
<213> ORGANISM: Artificial Sequence
<220> FEATURE:
<223> OTHER INFORMATION: Aminoacid seq. RPK (Figs 8-11)

<400> SEQUENCE: 35

Met Ser Ile Gln Glu Asn
1               5

<210> SEQ ID NO 36
<211> LENGTH: 35
<212> TYPE: PRT
<213> ORGANISM: Artificial Sequence
<220> FEATURE:
<223> OTHER INFORMATION: Aminoacid seq. from aminoacids 748 to 782 (Fig
      14)

<400> SEQUENCE: 36

Val Gly Asp Leu Val Ile Val Val Thr Gly Trp Arg Pro Gly Ser Gly
1               5                   10                  15

Tyr Thr Asn Ile Met Arg Val Leu Ser Ile Ser Asp Tyr Lys Asp Asp
            20                  25                  30

Asp Asp Lys
        35

<210> SEQ ID NO 37
<211> LENGTH: 11
<212> TYPE: PRT
<213> ORGANISM: Artificial Sequence
<220> FEATURE:
<223> OTHER INFORMATION: Aminoacid seq. from aminoacids 784 to 794 (Fig
      14)

<400> SEQUENCE: 37

Thr Arg Glu Leu Gln Ile Lys His Cys Ala Phe
1               5                   10

<210> SEQ ID NO 38
<211> LENGTH: 28
<212> TYPE: PRT
<213> ORGANISM: Artificial Sequence
<220> FEATURE:
<223> OTHER INFORMATION: Aminoacid seq. from aminoacids 796 to 823 (Fig
      14)

<400> SEQUENCE: 38

Leu Pro Ala Ile Cys Cys Leu Pro Leu Pro Arg Ala Phe Leu Asp Pro
1               5                   10                  15

Gly Arg Cys His Ser His Cys Pro Phe Leu Ile Lys
            20                  25

<210> SEQ ID NO 39
<211> LENGTH: 8
<212> TYPE: PRT
<213> ORGANISM: Artificial Sequence
<220> FEATURE:
<223> OTHER INFORMATION: Aminoacid seq. from aminoacids 825 to 832 (Fig
      14)

<400> SEQUENCE: 39

Gly Asn Cys Ile Ala Leu Ser Glu
1               5

<210> SEQ ID NO 40
<211> LENGTH: 20
```

<212> TYPE: PRT
<213> ORGANISM: Artificial Sequence
<220> FEATURE:
<223> OTHER INFORMATION: Aminoacid seq. from aminoacids 834 to 853 (Fig
      14)

<400> SEQUENCE: 40

Val Ser Phe Tyr Ser Gly Gly Trp Gly Gly Ala Gly Gln Gln Gly Gly
1               5                   10                  15

Gly Leu Gly Arg
            20

<210> SEQ ID NO 41
<211> LENGTH: 218
<212> TYPE: DNA
<213> ORGANISM: Homo sapiens

<400> SEQUENCE: 41
caagaccccc tccctaagac acccctgtcc caccggatga cccacacggg gaaaagagaa        60
gagacagagg gaatctattc tggtcgtcaa aacagtagga gagggagagt aaggtaccag       120
ggcgtcgggg tccgggtgtg actttcgtac agctaggtcc tcttgtatag tagggacgtc       180
gaagccagta cccagagatt cagggtttct ctgaatcg                               218

<210> SEQ ID NO 42
<211> LENGTH: 88
<212> TYPE: DNA
<213> ORGANISM: Artificial Sequence
<220> FEATURE:
<223> OTHER INFORMATION: synthetic

<400> SEQUENCE: 42
ttctggtcgt caaaacagta ggagagggag agtaaggtac cagggcgtcg gggtccgggt        60
gtgactttcg tacagctagg tcctcttg                                          88

<210> SEQ ID NO 43
<211> LENGTH: 158
<212> TYPE: DNA
<213> ORGANISM: Artificial Sequence
<220> FEATURE:
<223> OTHER INFORMATION: synthetic

<400> SEQUENCE: 43
tcccaccgga tgacccacac ggggaaaaga gaagagacag agggaatcta ttctggtcgt        60
caaaacagta ggagagggag agaaggtacc agggcgtcgg ggtccgggtg tgactttcgt       120
actcgtaggt cctttttatag tcgagagacg tcgacgcc                              158

<210> SEQ ID NO 44
<211> LENGTH: 154
<212> TYPE: DNA
<213> ORGANISM: Artificial Sequence
<220> FEATURE:
<223> OTHER INFORMATION: synthetic

<400> SEQUENCE: 44
cgctggacca ctagcaccac tgtccgaccg ccggaccgtc gccgatgtgg ttgtagtact        60
cccacgacag gtagtcgctg atgtttctgc tactgctatt tacttgcgca ctcaatgttt       120
atttcgtgac acggaagatc aacggtcggt agac                                  154

<210> SEQ ID NO 45
<211> LENGTH: 481

-continued

```
<212> TYPE: DNA
<213> ORGANISM: Artificial Sequence
<220> FEATURE:
<223> OTHER INFORMATION: synthetic

<400> SEQUENCE: 45
acaaacgggg aggggggcacg gaaggaactg ggaccttcca cggtgagggt gacaggaaag       60 gattattta  ctcctttaac gtagcgtaac agactcatcc acagtaagat aagaccccccc      120 accccacccc gtcctgtcgt tccccctcct aaccccttctg aatagcaggc atgctgggga     180
tgcggtgggc tctatgggtc ccgcagcccc aggcccacac tgaaagcatg tcgatccagg      240
agaacatatc atccctgcag cttcggtcat gggtctctaa gtcccaaaga gacttagcaa      300
agtccatcct gattggggct ttatcgtccg tacgacccct acgccacccg agatacccag      360
ggcgtcgggg tccgggtgtg actttcgtac agctaggtcc tcttgtatag tagggacgtc      420
gaagccagta cccagagatt cagggtttct ctgaatcgtt tcaggtagga actaaccccg      480
a                                                                       481
```

The invention claimed is:

1. A single guide sgRNA comprising a crRNA sequence chemically bound to a tracrRNA nucleotide sequence that interacts with a CRISPR-associated protein (Cas) polypeptide, wherein the sgRNA comprises SEQ ID NO 12.

2. A ribonucleoprotein (RNP) complex comprising the gRNA of claim 1 and a CRISPR-associated protein (Cas) polypeptide.

3. The RNP complex of claim 2, wherein the Cas polypeptide is a Cas9 polypeptide.

4. The RNP complex of claim 2, wherein the Cas polypeptide is a high-fidelity or enhanced specificity Cas9 polypeptide variant.

5. A system comprising the RNP complex of claim 2 and an adeno-associated viral particle or donor AAV vector that can deliver a recombinant donor template for CRISPR-based gene editing via homology-directed repair in a target cell.

6. The system of claim 5, wherein the adeno-associated viral particle or donor AAV vector comprises a DNA sequence which in turn comprises a left homologous arm (LHA) and a right homologous arm (RHA), a correction donor template coding for the PKLR gene and a specialized termination sequence for protein expression in eukaryotic cells.

7. The system of claim 6, wherein the LHA is SEQ ID NO 13, RHA is SEQ ID NO 14, the correction donor template coding for the PKLR gene is SEQ ID NO 16 and the bGH poly(A) sequence is SEQ ID NO 18, or a variant of any of these sequences having at least 95% sequence identity to any of these sequences.

8. The system of claim 6, wherein the adeno-associated viral particle or donor AAV vector further comprises a 5'UTR sequence.

9. A method for inducing a stable gene modification in a primary cell via homologous recombination, wherein the primary cell is characterized by comprising a target nucleic acid comprising a PKLR gene which in turn comprises one or more mutations in the PKLR gene and a nucleotide sequence that is complementary to SEQ ID NO 1 or 11, and the method comprises:

a. introducing into the primary cell the RNP complex of claim 2; and simultaneously or sequentially b. introducing into the primary cell an adeno-associated viral particle or donor AAV vector that can deliver a recombinant donor template for CRISPR-based gene editing via homology-directed repair in the primary cell;

wherein, the stable gene modification of the target nucleic acid comprises the compensation of disease-causing mutations of the PKLR gene, by introducing the donor AAV vector comprising the recombinant donor template.

10. A CRISPR system comprising an mRNA encoding a Cas polypeptide and the sgRNA of claim 1.

11. The CRISPR system of claim 10, wherein the Cas polypeptide is a Cas9 polypeptide.

12. The CRISPR system of claim 10, wherein the Cas polypeptide is a high-fidelity or enhanced specificity Cas9 polypeptide variant.

13. A system comprising the CRISPR system of claim 10 and an adeno-associated viral particle or donor AAV vector that can deliver a recombinant donor template for CRISPR-based gene editing via homology-directed repair in a target cell.

14. The system of claim 13, wherein the adeno-associated viral particle or donor AAV vector comprises a DNA sequence which in turn comprises a left homologous arms (LHA) and right homologous arm (RHA), a correction donor template coding for the PKLR gene and a specialized termination sequence for protein expression in eukaryotic cells.

15. The system of claim 14, wherein the LHA is SEQ ID NO 13, RHA is SEQ ID NO 14, the correction donor template coding for the PKLR gene is SEQ ID NO 16 and the bGH poly(A) sequence is SEQ ID NO 18, or a variant of any of these sequences having at least 95% sequence identity to any of these sequences.

16. The system of claim 14, wherein the adeno-associated viral particle or donor AAV vector further comprises a 5'UTR sequence.

17. The system of claim 7, wherein the adeno-associated viral particle or donor AAV vector further comprises a 5'UTR sequence, wherein such sequence is SEQ ID NO 15 or a variant of SEQ ID NO 15 having at least 95% sequence identity to SEQ ID NO 15.

18. The system of claim 15, wherein the adeno-associated viral particle or donor AAV vector further comprises a 5'UTR sequence, wherein such sequence is SEQ ID NO 15 or a variant of SEQ ID NO 15 having at least 95% sequence identity to SEQ ID NO 15.

19. A method for inducing a stable gene modification in a primary cell via homologous recombination, wherein the primary cell is characterized by comprising a target nucleic acid comprising a PKLR gene which in turn comprises one or more mutations in the PKLR gene and a nucleotide sequence that is complementary to SEQ ID NO 1 or 11, and the method comprises:

a. introducing into the primary cell the CRISPR system of claim 10; and simultaneously or sequentially b. introducing into the primary cell an adeno-associated viral particle or donor AAV vector that can deliver a recombinant donor template for CRISPR-based gene editing via homology-directed repair in the primary cell;

wherein, the stable gene modification of the target nucleic acid comprises the compensation of disease-causing mutations of the PKLR gene, by introducing the donor AAV vector comprising the recombinant donor template.

20. The system of claim 7, wherein the specialized termination sequence for protein expression in eukaryotic cells is the bGH poly(A) sequence.

21. The system of claim 14, wherein the specialized termination sequence for protein expression in eukaryotic cells is the bGH poly(A) sequence.

\* \* \* \* \*